(12) United States Patent
Zhu et al.

(10) Patent No.: US 8,524,744 B2
(45) Date of Patent: Sep. 3, 2013

(54) ARYLAMINE KETONES, THEIR PREPARATION METHODS, THE PHARMACEUTICAL COMPOSITION CONTAINING THEM AND THEIR USE

(75) Inventors: Liya Zhu, Beijing (CN); Wenjie Wang, Beijing (CN); Halhong Huang, Beijing (CN); Ziyun Lin, Beijing (CN); Liyuan Mou, Beijing (CN); Zhengui Nie, Beijing (CN); Yu He, Beijing (CN); Xueyu Ouyang, Beijing (CN); Shanying Peng, Beijing (CN); Dongfong Zhang, Beijing (CN); Jun Wei, Beijing (CN)

(73) Assignee: Institute of Mataria Medica, Chinese Academy of Medical Sciences, Beijing (CN)

( * ) Notice: Subject to any disclaimer, the term of this patent is extended or adjusted under 35 U.S.C. 154(b) by 1208 days.

(21) Appl. No.: 11/659,636

(22) PCT Filed: Aug. 5, 2005

(86) PCT No.: PCT/CN2005/001201
§ 371 (c)(1),
(2), (4) Date: Nov. 16, 2007

(87) PCT Pub. No.: WO2006/024217
PCT Pub. Date: Mar. 9, 2006

(65) Prior Publication Data
US 2008/0221106 A1    Sep. 11, 2008

(30) Foreign Application Priority Data
Aug. 6, 2004  (CN) .......................... 2004 1 0070528

(51) Int. Cl.
*A61K 31/445*  (2006.01)
*C07D 211/60*  (2006.01)

(52) U.S. Cl.
USPC .......................................... 514/330; 546/227

(58) Field of Classification Search
USPC .......................................... 546/227; 514/330
See application file for complete search history.

(56) References Cited

PUBLICATIONS

Levvy et al., Journal of teh Chemical Society (1928) 1572-4.*
Byrn et al., Solid-Sate Chemistry of Drugs, Second Edition, 1999, pp. 233-247.*
Levvy et al., Journal of the Chemical Society (1938) 1572-4.*
Britton et al., Journal of the American Pharmaceutical Association, Nov. 1954; 43(11): 641-3.*

\* cited by examiner

*Primary Examiner* — Rebecca Anderson
(74) *Attorney, Agent, or Firm* — Fay Sharpe LLP

(57) ABSTRACT

Disclosed Arylamine ketones of formula (I), their preparation methods, the pharmaceutical compositions containing them and their use in preventing and/or treating the diseases related to the plaque-activating factors, especially in anti-inflammation and immunization, more especially in the treatment of the acute or chronic inflammation, such as, osteoarthritis, oarthritis deformans, etc.

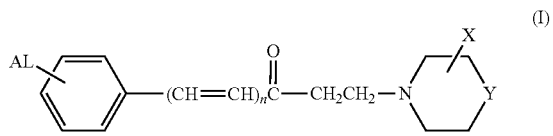

9 Claims, No Drawings

ARYLAMINE KETONES, THEIR PREPARATION METHODS, THE PHARMACEUTICAL COMPOSITION CONTAINING THEM AND THEIR USE

This application is a 371 of PCT Application Ser. No. PCT/CN2005/001201, filed Aug. 5, 2005, which claimed priority to Chinese Patent Application No. 200410070528.2, filed Aug. 6, 2004.

TECHNICAL FIELD

The present invention is concerned with araminone compounds of the general formula (I), their preparations and pharmaceutical compositions containing them a compound of formula (I). and these compounds's use in the preventing from and/or treatingment of various diseases relating to platelet activating factor (PAF), especially for the therapy of acute, chronic and immune inflammation.

BACKGROUND ART

Rheumatoid arthritis (RA) is a systemic autoimmune disease with high incidence rate and long course. The patients suffer from distress and even lose the ability for work and life. It is difficult to be cured and easy to relapse.

So far there are no satisfactory drugs to therapy rheumatoid arthritis. In the present available drugs for therapy of this disease include steroid anti-inflammatory drugs (SAIDs) and non-steroid anti-inflammatory drugs (NSAIDs). Although many drugs were supplied, all of them have serious side-effects. For example, SAIDs can make the body produce hormone-dependence, influence the metabolism and inhibit the immune system. Since NSAIDs inhibit cyclooxygenase and reduce production of prostaglands, they can damage the gastrointestinal mucosa.

The pathological process of rheumatoid arthritis involves many inflammatory mediators. Platelet activating factor (PAF) is the important ones which belongs to phospholipids and is produced by several inflammatory cells. It can induce various responses after binding to its receptor and coupling through G-protein. PAF receptor antagonists compete with PAF for their receptors, so they can effectively inhibit inflammation. The previous investigation also shows PAF can enhance the production of other inflammatory mediators, the expression of cytokines, activate nuclear factor and influence many pathological process related to inflammation. PAF receptor has became an important target for developing new anti-inflammatory and immuno-regulatory drugs. Moreover, PAF receptor antagonists can protect the gastrointestinal mucosa which is the protrusive advantage comparing with the launched anti-inflammatory drugs.

In the recent years some natural and synthesized compounds which have PAF receptor antagonistic effect were found. More than 60 pharmaceutical companies and institutes study on this field. About 550 compounds were synthesized and examined in biological experiments. Among them 18 enter the phase I clinic trail, 17 enter the phase II clinic trail, 2(BN52021 and Y-24180) enter the phase III clinic trail. Especially, rheumatoid arthritis is one of the indications for those compounds. Among them, 2 compounds are researched at the stage of biological examination. Those compounds, such as CV-6209 can inhibit rat paw swelling induced by several inflamed agents (for instance PAF, carrageenan, histamine, 5-serotonin). BN50730 significantly improves the symptom of patients with rheumatoid arthritis after administration for 4 weeks. WEB2170 can inhibit the increase of new vessels in mouse angiogenesis model induced by synovial fluid of patient with rheumatoid arthritis. WEB2170 can inhibit the increase of TNF-αlevel in synovial fluid of rat ankle joint induced by immune complex. A-85783 can significantly inhibit the rat ear edema induced by PAF or PMA. BN50730 can significantly inhibit the joint swelling of mouse with arthritis induced by type III collagen, decrease the precipitation of fibronectin and the consumption of proteoglycan in cartilage. BN50730 can reduce the early activity of NF-κB and the expression of TNF-αmRNA in the infected mice. LDP-392 can significantly inhibit the mouse ear edema induced by arachidonic acid.

SUMMARY OF THE INVENTION

One object of this invention is to provide a series of compounds expressed by the general formula (I), their stereoisomers, pharmaceutically acceptable salts, solvates, esters and pro-drugs.

An other aim of this invention also relates to the methods for the preparation of the compounds of formula (I), their stereoisomers and pharmaceutically acceptable salts.

A further aim of this invention is to provide one kind of pharmaceutical composition, which includes a compound at least expressed by the general formula (I), stereoisomers and pharmaceutically acceptable salts, carriers and/or excipients.

A still further aim of this invention is to provide applications for preventing from and/or treatment of inflammation by the compounds expressed by the general formula (I), their stereoisomers and pharmaceutically acceptable salts.

According to the invention, the araminone compounds are A compound represented by the following general formula (I)

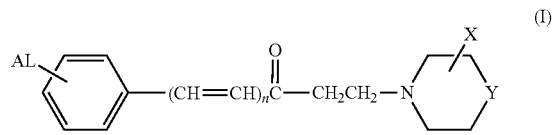

(I)

Wherein AL is selected from the group consisting of hydrogen, hydroxy, halogen (F, Cl, Br, I), $CF_3$, CN, $NO_2$, $NR_1R_2$ ($R_1$, $R_2=C_{1-6}$ alkyl), $C_{1-6}$ alkyl, $C_{1-6}$ alkoxy, methylenedioxy, 3,4-di-$C_{1-6}$ alkoxy, 3,4,5-tri-$C_{1-6}$ alkoxy, 3-methoxy-4-hydroxy, 3,4-methylenedioxy-5-methoxy, 3-hydroxy-4-methoxy;

n=0, 1, 2;

Y of general formula (I) is selected from the group consisting of C, N, O;

X of general formula (I) is selected from the group consisting of hydrogen, $C_{1-6}$ alkyl, COOR (R=hydrogen, $C_{1-6}$ alkyl, $C(CH_3)_3$, substituted or unsubstituted aryl, CO-Ph, $CH_2$Ph, $CH_2CH_2$OH, $CONR_1R_2$ ($R_1$, $R_2=C_{1-6}$ alkyl).

In order to complete the object of the present invention, preferable compounds include, but are not limited to the compounds represented by following general formula (Ia)

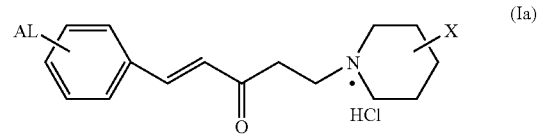

(Ia)

Wherein, AL is selected from the group consisting of hydrogen, hydroxy, halogen (F, Cl, Br, I), $CF_3$, CN, $NO_2$, $NR_1R_2$ ($R_1$, $R_2=C_{1-6}$ alkyl), $C_{1-6}$ alkyl, $C_{1-6}$ alkoxy, methylenedioxy, 3,4-di-$C_{1-6}$ alkoxy, 3,4,5-tri-$C_{1-6}$ alkoxy, 3-methoxy-4-hydroxy, 3,4-methylenedioxy-5-methoxy, 3-hydroxy-4-methoxy;

Wherein, X is selected from the group consisting of $C_{1-6}$ alkyl, $COOCH_2CH_3$, $C_{1-6}$ alkoxy, benzyl, 2,3,4-trimethoxy-benzyl, 3,4-methylenedioxy-benzyl, benzoyl, COOH.

1 Preferable compounds represented by following general formula (Ia) include, but are not limited to the compounds represented by following general formula (Iaa)

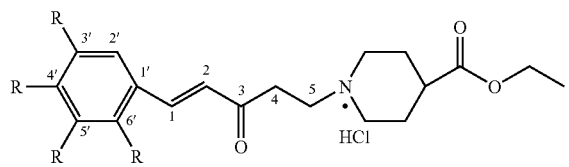

(Iaa)

Wherein, $R'_3$, $R'_4$, $R'_5$ and $R'_6$ are independently selected from the group consisting of hydrogen, $C_{1-6}$ alkyl methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy.

2. Preferable compounds represented by following general formula (Ia) include, but are not limited to the compounds represented by following general formula (Iab)

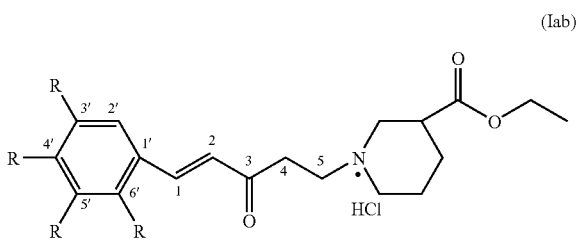

(Iab)

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy.

3. Preferable compounds represented by following general formula (Ia) include, but are not limited to the compounds represented by following general formula (Iac)

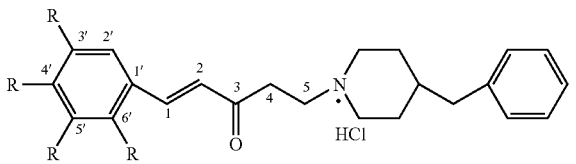

(Iac)

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy.

4. Preferable compounds represented by following general formula (Ia) include, but are not limited to the compounds represented by following general formula (Iad)

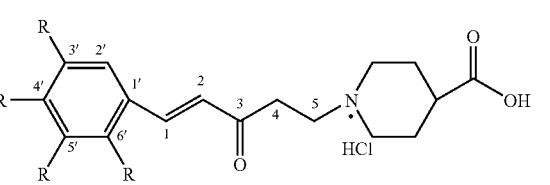

(Iad)

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy.

In order to complete the object of the present invention, preferable compounds include, but are not limited to the compounds represented by following general formula (Ib)

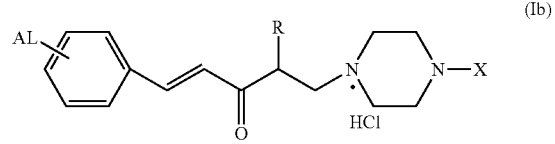

(Ib)

Wherein, AL is selected from the group consisting of hydrogen, hydroxy, halogen (F, Cl, Br, I), $CF_3$, CN, $NO_2$, $NR_1R_2$ ($R_1$, $R_2=C_{1-6}$ alkyl), $C_{1-6}$ alkyl, $C_{1-6}$ alkoxy, methylenedioxy, 3,4-di-$C_{1-6}$ alkoxy, 3,4,5-tri-$C_{1-6}$ alkoxy, 3-methoxy-4-hydroxy, 3,4-methylenedioxy-5-methoxy, 3-hydroxy-4-methoxy;

Wherein, X is selected from the group consisting of $C_{1-6}$ alkyl, $COOCH_2CH_3$, $C_{1-6}$ alkoxy, substituted or unsubstituted aryl, benzyl, 2,3,4-trimethoxy-benzyl, 3,4-methylenedioxy-benzyl, benzoyl, COOH, Wherein, R is independently selected from the group consisting of $C_{1-3}$ alkyl 1. Preferable compounds represented by following general formula (Ib) include, but are not limited to the compounds represented by following general formula (Iba)

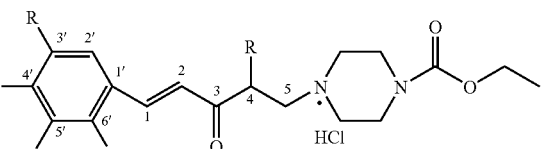

(Iba)

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy, Wherein, $R_4$ is independently selected from the group consisting of $C_{1-3}$ alkyl.

2. Preferable compounds represented by following general formula (Ib) include, but are not limited to the compounds represented by following general formula (Ibb)

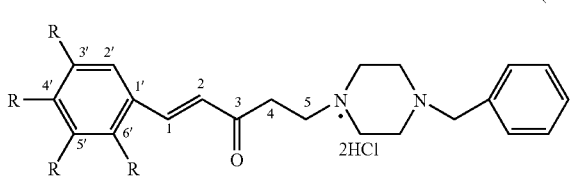

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy.

3. Preferable compounds represented by following general formula (Ib) include, but are not limited to the compounds represented by following general formula (Ibc)

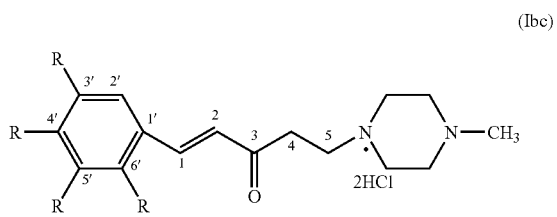

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy.

4. Preferable compounds represented by following general formula (Ib) include, but are not limited to the compounds represented by following general formula (Ibd)

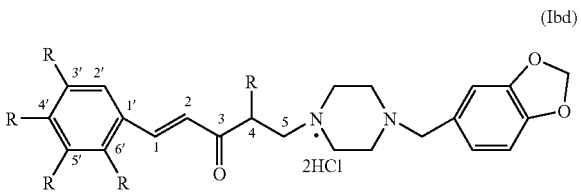

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy, Wherein, $R_4$ is independently selected from the group consisting of $C_{1-3}$ alkyl.

5. Preferable compounds represented by following general formula (Ib) include, but are not limited to the compounds represented by following general formula (Ibe)

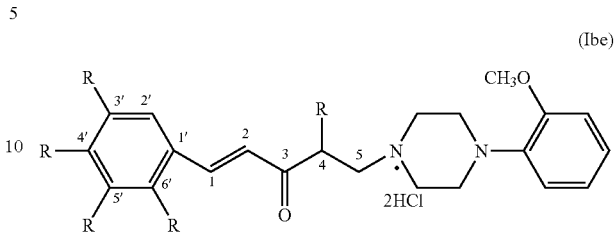

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy, Wherein, $R_4$ is independently selected from the group consisting of $C_{1-3}$ alkyl.

In order to complete the object of the present invention, preferable compounds include, but are not limited to the compounds represented by following general formula (Ic)

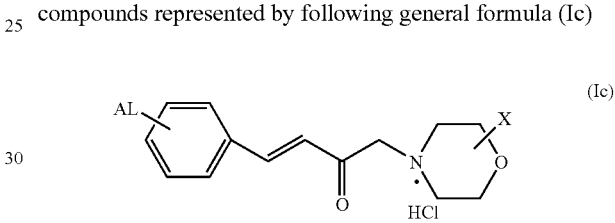

Wherein, AL is selected from the group consisting of hydrogen, hydroxy, halogen (F, Cl, Br, I), $CF_3$, CN, $NO_2$, $NR_1R_2$ ($R_1$, $R_2$=$C_{1-6}$ alkyl), $C_{1-6}$ alkyl, $C_{1-6}$ alkoxy, methylenedioxy, 3,4-di-$C_{1-6}$ alkoxy, 3,4,5-tri-$C_{1-6}$ alkoxy, 3-methoxy-4-hydroxy, 3,4-methylenedioxy-5-methoxy, 3-hydroxy-4-methoxy;

Wherein, X is selected from the group consisting of $C_{1-6}$ alkyl, X can be at any positions which can be substituted on six membered hetero cycle, preferred in the 2,6-positions of morpholine cycle;

1. Preferable compounds represented by following general formula (Ib) include, but are not limited to the compounds represented by following general formula (Ica)

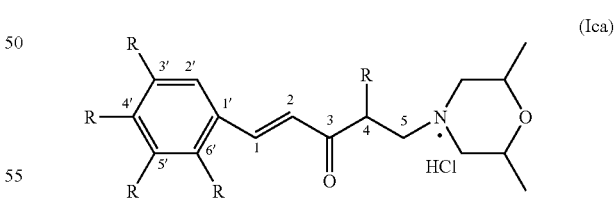

Wherein, $R'_3$, $R'_4$, $R'_5$ and $R'_6$ are independently selected from the group consisting of hydrogen, $C_{1-6}$ alkyl, methylenedioxy, $C_{1-6}$ alkoxy, halogen (F, Cl, Br, I), hydroxy, $NO_2$, $CF_3$, CN, 3,4,5-tri-$C_{1-6}$ alkoxy, 3-methoxy-4-hydroxy, 3,4-methylenedioxy-5-methoxy, Wherein, $R_4$ is independently selected from the group consisting of $C_{1-3}$ alkyl.

In order to complete the object of the present invention, preferable compounds include, but are not limited to the compounds represented by following general formula (Id)

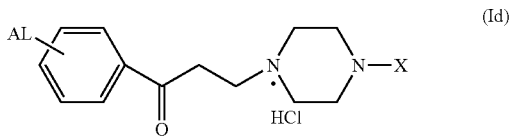

(Id)

Wherein, AL is selected from the group consisting of hydrogen, hydroxy, halogen (F, Cl, Br, I), $CF_3$, CN, $NO_2$, $NR_1R_2$ ($R_1$, $R_2=C_{1-6}$ alkyl), $C_{1-6}$ alkyl, $C_{1-6}$ alkoxy, methylenedioxy, 3,4-di-$C_{1-6}$ alkoxy, 3,4,5-tri-$C_{1-6}$ alkoxy, 3-methoxy-4-hydroxy, 3,4-methylenedioxy-5-methoxy, 3-hydroxy-4-methoxy;

Wherein, X is selected from the group consisting of $C_{1-6}$ alkyl, $COOCH_2CH_3$, $C_{1-6}$ alkoxy, benzyl, 2,3,4-trimethoxybenzyl, 3,4-methylenedioxy-benzyl, benzoyl, COOH.

As defined above, when the compound of present invention is basic, its salts may be prepared from pharmaceutically acceptable acids. Particularly the preferred are hydrochloric salts, hydrobromic salts, sulphuric salts or hydrosulfuric salts, succinic salts, maleic salts and the like;

According to the invention, the methods of preparation of the compounds are also provided.

The compounds of the invention or their hydrochloric salts can be prepared by the following reaction route:

1. Preparation of substituted or unsubstituted 4-phenyl-3-buten-2-one

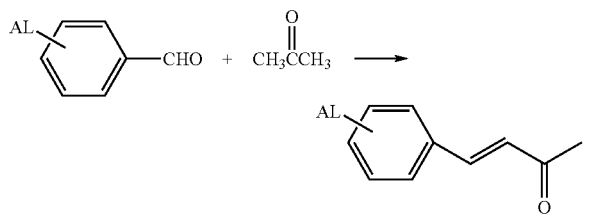

Starting materials: substituted or unsubstituted benzaldehyde and acetone. meanwhile, excess of acetone is used as the solvent of this reaction.

Reaction condition: The reaction is carried out in the presence of a base, the preferred base is the hydroxide of alkali metals, or aluminum oxide, especially, potassium hydroxide, sodium hydroxide.

Reaction Solvent: Excessive acetone is used as the solvent. The other solvent, such as ethanol and/or water may be added, according to the solubility of various benzaldehyde derivatives and the selected base. The amount of solvent is adjusted according to the solubility of the reactants.

Temperature: The reaction temperature is preferably 5-40° C., the preferred is 10-30° C., the most preferred is 15-25° C.

Time: The reaction time is 1-40 hours, the preferred is 5-30 hours, the most preferred is 14-25 hours.

The process of the reaction may be monitored by TLC or HPLC. The reaction mixture is neutralized by an acid when the reaction completed. The preferred acid is inorganic acid, the most preferred acid is HCl. The reaction product may be obtained by filtration or extraction with organic solvent. The product may be further washed, dried and purified to fulfill the requirements of the reaction of the next step.

2. Preparation of Substituted or unsubstituted acetophenone

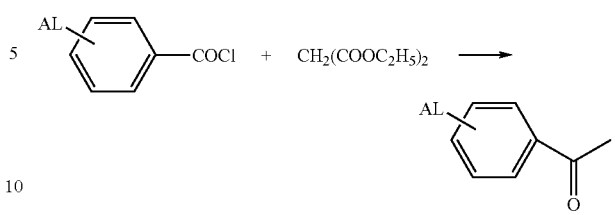

Starting materials: Substituted or unsubstituted benzoyl chloride with diethyl malonate;

Reaction Conditions: The reaction is conducted under anhydrous condition in a suitable solvent with refluxing;

Solvent: Anhydrous ether and ethanol are used as the solvent;

Temperature: The temperature of the reaction is 20~60° C., the more preferred is 25~55° C., the most preferred is 30~50° C.;

Time: The time of the reaction is 1-15 hours, the preferred time is 3-13 hours, the most preferred time is 5-10 hours.

The process of the reaction may be monitored by TLC or HPLC. The reaction product may be obtained by filtration or extraction with organic solvent. The product may be further washed, dried and purified to fulfill the requirements of the reaction of the next step.

3. Preparation of 5-[disubstitutedamino]-1-substitutedphenyl-1-penten-3-one hydrochloride

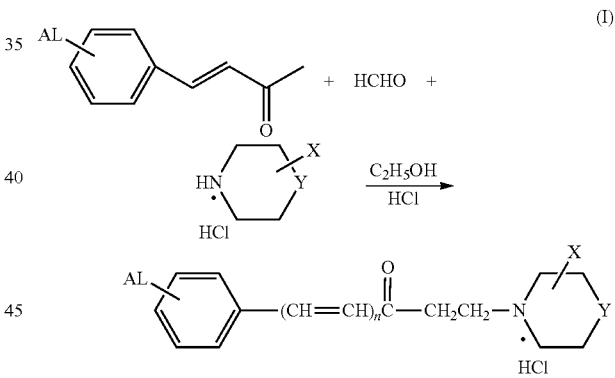

(I)

Starting materials: Substituted or unsubstituted 4-phenyl-3-buten-2-one, paraformaldehyde and hydrochloride salts of substituted or unsubstituted piperazine, piperidine or morpholine.

Reaction condition: The reaction is conducted under acidic conditions, adjusting the pH value of the reaction solution to pH 3-4 with acid, preferably by hydrochloric acid.

Solvent: Anhydrous ethanol is used as the solvent, the required amount of the solvent is adjusted according to the solubility of the reactants.

Temperature: The reaction is carried out under reflux, the preferred temperature is about 90° C.

Time: The time of the reaction is 5-25 hours, the preferred time is 10-20 hours, the most preferred time is about 15 hours.

The process of the reaction may be monitored by TLC or HPLC. After the completion of reaction, the mixture is concentrated under reduced pressure, separated solid is filtrated, dried and purified by recrystallization.

The substituted group AL in the compounds of the invention can be introduced via start materials, that is, refluxing appropriate substituted or unsubstituted 4-phenyl-3-buten-2-one with AL group on the phenyl ring with the appropriate secondary amine or its hydrochloride and paraformaldehyde in acidic anhydrous ethanol.

Furthermore, the present invention relates to the pharmaceutical compositions, which it generally contains the compounds of the present invention as the active ingredient from 0.1 to 95% by weight and conventionally pharmaceutically excipients and/or auxiliaries.

The pharmaceutical compositions in the present invention can be prepared by the known art in the relating fields. In order to achieve the administrating purpose, the compounds of the present invention may be made into dosage forms for the use of drugs to people or animals, by mixed with one or more solids or liquids excipients and/or auxiliaries, if needed.

The compounds and their complex in this invention can be administrated at unit dose by gastrointestinal tract or parenteral pathways, such as oral, intramuscular injection, subcutaneous injection, nasal mucosa, mucous membrane of mouth, cutis, abdominal injection or rectum.

The compounds and their complex can be administrated by injection which includes intravenous injection, intramuscular injection, subcutaneous injection, intradermal injection or acupuncture point injection.

The formulation of the present invention may be in the solid, semi-solid or liquid dosage forms. For example, the liquids include the solutions, colloids, emulsion, suspension and the like. The other dosage forms include tablets, capsules, sprays, aerosols, pills, drop pills, powder, granules, fine subtly systems, suppositorys, freeze-dried powder injections and the like.

The compounds of the present invention may be prepared into specific formulations, such as implantation of slow-releases, sustained-released systems, time-release capsules or tablets, directing-targets and various fine subtly systems.

In order to prepare tablets with administration of the unit form of drugs, it may extensively use the various known carrier(s) in the related fields. For example, diluents and absorbents, such as starch, dextrin, calcium sulfate, lactose, mannitol, sucrose, sodium chloride, glucose, urea, calcium carbonate, kaolin, microcrystalcelluloses and aluminum silicate and the like; moist and bonding agents, such as water, glycerol, polyethyleneglycol, ethanol, propanol, starch thick liquid, dextrin, syrups, honey, glucose solution, Arabic gum, gelatin, sodium carboxymethyl celluloses, lacta, methylcellulose, potassium phosphate, polyvinylpyrrolidone and the like; disintegrants, such as dried starch, marine alginates, agar-powders, brown-algae starch, sodium hydrogencarbonate citric acid, calcium carbonate, polyoxyethylene sorbitol fatty acid ester, sodium lauryl sulfonate, methylcellulose, ethylcellulose and the like; disintegrant inhibitors, such as sucrose, glycerol tristearate, cocoa butter, hydrogen-oil and the like; absorbent-promotors, such as quaternary ammonium salt, sodium lauryl sulfate and the like; lubricants, such as talc, silicon oxide, corn-starch, stearates, boric acid, paraffin oil, polyethyleneglycol and the like. Further tablets also may be coated, for example sugarcoating tablets, film-coating tablets, solvable-coating-tablets in intestines and double or more layers tablets.

In order to prepare pills in unit of administration, the known various carriers in the related fields can be applied. For example, diluents and absorbents, such as glucose, lactose, starch, cocoa butter, hydro-vegetable oils, polyvinylpyrrolidone, Gelucire, kaolin, talc and the like; bonding agents such as arabic gum, tragacanth, gelatin, ethanol, honey, liquid-sugars, rice pastes or flour pastes and the like; disintegrants such as agar powder, dried starch, marine alginates, sodium lauryl sulfonate, methylcellulose, ethylcellulose and the like.

In order to prepare capsules in the unit of administration, the compounds of the present invention may be mixed with above various carrier(s). The mixtures obtained were packed into hard or soft capsules and also may be prepared into microcapsules which further are used as suspended in hydra-media and packed into hard capsules or to be prepared injections.

The compounds of the present invention may be prepared as the injection dosage forms, such as solutions, suspensions, emulsions, freeze-dried powder suitable for injections, which these preparations may be contained water or no water, one and/or more pharmaceutically acceptable carrier(s), diluents, preservatives, surfactants or dispersing agents. For example, diluents are selected from water, ethanol, polyethylene glycol, 1,3-propylene glycol, ethyloxyisostearates, polyoxyisostearates, polyoxyethylene sorbitol fatty acid ester and the like. In addition, for preparing the isotonic injections, the assistants conventionally used in the related fields can be added to the injection forms, such as the suitable sodium chloride, aqueous dextrose, glucose or glycerol, also can be added auxiliary dissolving agents, buffering agents, pH-modulators and the like.

Besides, colorable agents, preservatives, perfumes, correctives, sweetening agents (such as sodium saccharin) and the like may be added to the preparation, if needed.

For achieving administrating purpose and enhancing treating effect, the compounds or pharmaceutical compositions of the present invention may be administrated by any known methods. The administrating dosage of the present invention may be extensively varied by depending on a lot of factors, for example, the serious degree of the prevented from or treated of diseases, sex, age, body weights, disposition and individual differences of the patients or animals, administrating routes or number of times and treating purposes. In general, the effective dosages of pharmaceutically active ingredients of the present invention is known for technical person in the related fields. In order to achieve the requirement of treating effective dosages and complete the purpose of preventing from or treatment of diseases, the quantity of drugs contained in the final preparation may be properly modulated according to the practical content of the compounds in the pharmaceutical compositions.

The daily suitable ranges of dosages contained the compounds of the present invention are within 0.001-150 mg/Kg body weights, preferably are within 0.1-100 mg/Kg body weights, more preferably are within 1-60 mg/Kg body weights, the most preferred are within 2-30 mg/Kg body weights. The doses above described may be used in one portion or several portions, for example two, three or four portions, which is depended on the experiences of clinicians and the other different schemes of administration or treating methods.

The total dosages can be administrated in multiple or single dose. The compounds or compositions of the present invention may be alone administrated or combined with the other treating drugs or cooperating agents, and the quantity of the compounds can be modulated according to the actual situation.

It was proved that the araminone compounds in the present invention exhibit powerful anti-inflammatory effects in several animal models as the evaluating methods for anti-arthritis drugs, such as the cutaneous vascular permeability in mice, carrageenan-induced paw swelling in rats, adjuvant arthritis in rats and type II collagen-induced arthritis in rats and so on.

The radioligand receptor binding experiment and biochemical or molecular biological experiments show that they have definite mechanisms and low acute toxicity.

The arminone compounds in the present invention have significant competitive effect on the binding between [$^3$H]and its receptor of rat polymorphonuclear leucocytes, mice macrophages and rabbit platelet. They can inhibit the release of lysosomal enzyme from polymophornuclear leucocytes (PMN) and the chemotaxis of PMN and macrophages. They can also decrease the raise of intracellular calcium level in PMN and prevent the production of NO and expression of TNFαin macrophages. In animal models, they can inhibit the ear edema induced by croton oil in mice and the carrageenan-induced paw swelling in mice and rats, block the irritant-induced increase of cutaneous vascular permeability in mice, prevent the granuloma induced by cotton ball, adjuvant arthritis and type II collagen-induced arthritis in rats, inhibit the angiogenesis in chronic granulomatous air pouch in mice. In clinic, they should be used to therapy the acute or chronic inflammatory diseases, for instance, rheumatoid arthritis.

The indications for the complex containing one of the compounds in the invention mainly include all acute and chronic inflammatory diseases and immune diseases, such as acute and chronic rheumatic arthritis and ankylosing spondylitis, osteoarthritis, scapulohumeral periarthritis, bursitis, tendonitis, peritendonitis, sprain, strain and other soft tissues injury. For serious infected inflammation, such as tonsillitis, otitis and sinusitis, antibiotic drugs should be used simultaneously. Moreover, the complex containing one of the compounds in the invention also can be used to therapy the thrombosis in blood vessel caused by platelet aggregation, such as myocardial infarction and cerebral vessel infarction.

PREPARATION EXAMPLES

The starting materials in the preparation examples of the present invention may be prepared by the conventional procedures and/or well-known methods in the related fields. All the secondary amines in the examples are commercially available, such as substituted or unsubstantiated piperazine, piperidine, morpholine and can also be prepared by the conventional procedures and/or well-known methods in the related fields. The secondary amine salts, such as HCl salts, can also be prepared by the conventional procedures and/or well-known methods in the related fields.

Preparation 1

4-(4-Chlorophenyl)-3-buten-2-one

To the solution of 4-chlorobenzaldehyde (8.43 g, 60 mmol) in acetone(60 ml) and ethanol (6 ml) was added under stirring 10% NaOH aqueous solution(48 ml) and water(240 ml), the reaction solution was stirred at 25° C. for 8 hr. The precipitated solid was collected by filtration and washed with water, dried to give the title compound 10.5 g as a white solid, mp 56-57° C., yield: 96.9%.

Preparation 2

4-(4-Hydroxyphenyl)-3-buten-2-one

4-Hydroxybenzaldehyde (10 g, 82 mmol) was dissolved in 28 ml of 10% sodium hydroxide aqueous solution, then acetone (20 ml) and 10% sodium hydroxide aqueous solution (40 ml) was added under stirring, and the reaction mixture was stirred for 6 hr at room temperature. separated solid diluted with water until all separated solid dissolved. The reaction mixture was neutralized with hydrochloric acid to pH=7.0. The precipitated solid was collected by filtration and washed with water and ethanol successively. The crude product was recrystallized from ethanol to give 9.3 g of a pale yellow solid, mp: 104-105° C., yield: 70.4%.

Preparation 3

4-(4-Methylphenyl)-3-buten-2-one

Water (20 ml) and 10% NaOH aqueous solution (4 ml) were added under stirring to the solution of 4-methylbenzaldehyde (10.2 g, 10 mmol) in acetone (10 ml). The reaction mixture was stirred for 14 hr at room temperature, then the pH value was adjusted to pH=7.0 with 10% hydrochloric acid, extracted with methylene chloride. The combined methylene chloride extract was washed with water, dried over anhydrous sodium sulfate, filtered and concentrated to give 0.73 g of a yellow viscous oil, yield: 45.6%.

Preparation 4

4-(4-Methoxy-3-ethoxyphenyl)-3-buten-2-one

Anhydrous sodium carbonate (3.98 g) and dimethyl sulfate (3.78 g, 30 mmol) were added to a solution of 4-(4-hydroxy-3-ethoxyphenyl)-3-buten-2-one (6.2 g, 30 mmol) in acetone (40 ml). The reaction mixture was stirred under refluxing for 8 hr. The precipitated yellow solid was filtered, washed with acetone, and then recrystallized from anhydrous ethanol to give 4.3 g of a yellow crystal, mp 95-96° C., yield 65.3%.

Preparation 5

4-(3-Ethoxy-4-hydroxyphenyl)-3-buten-2-one

10% sodium hydroxide aqueous solution (80 ml) was added under stirring to a solution of 3-ethoxy-4-hydroxybenzaldehyde (16.6 g, 100 mmol) in acetone (50 ml), 95% ethanol (50 ml) and water (400 ml). The reaction mixture was stirred for 24 hr at room temperature, after the reaction completed, the reaction mixture was neutralized with 6N hydrochloric acid to adjust pH=7.0, the precipitated yellow solid was collected by filtration, washed with water and ethanol successively, dried, and then recrystallized from 95% ethanol to give 14.5 g of a yellow crystal, mp: 98-100° C., yield 70.4%.

Preparation 6

4-(3-Methoxy-4-ethoxyphenyl)-3-buten-2-one

10% sodium hydroxide aqueous (40 ml) was added under stirring to a solution of 3-methoxy-4-ethoxybenzaldehyde (9.09 g, 50 mmol) in acetone (25 ml), 95% ethanol (25 ml) and water (200 ml). The reaction mixture was stirred for 24 hr at room temperature, after the reaction completed, the reaction mixture was neutralized with 6N hydrochloric acid to adjust pH=7.0. The precipitated solid was collected by filtrating and washed with water and ethanol successively, dried, and then recrystallized from 95% ethanol to give 7.38 g of a pale yellow solid, mp: 95-97° C., yield: 66.5%.

Preparation 7

3,4,5-Trimethoxybenzaldehyde (6.62 g, 33.7 mmol) was dissolved in acetone (105 ml), then aluminum oxide(11.65 g, 114.7 mmol) was added to the solution and the reaction mixture was heated under stirring for 24 hr, after the reaction completed, the reaction mixture was neutralized with 6N hydrochloric acid to adjust pH=7.0. The pracipitated solid was collected by filtration and washed with water and ethanol successively, and then recrystallized from 95% ethanol to give 3.33 g of a pale yellow solid, mp: 90-91.5° C., yield: 21.9%.

Preparation 8

4-(4-Cyanophenyl)-3-buten-2-one

Water (150 ml) and 10% NaOH aqueous solution (4.5 ml) were added under vigorous stirring to a solution of 4-cyanobenzaldehyde (7.0 g, 80.6 mmol) in acetone (40 ml) and water(25 ml). The reaction mixture was stirred at 14° C. for 8 hr, after the reaction completed, the reaction mixture was neutralized with 6N hydrochloric acid to adjust pH=7-8.The precipitated separated solid was collected by filtration and dried, then recrystallized from anhydrous ethanol to give 4.8 g of crystals in needles, mp: 102-103° C., yield: 49.25%.

Preparation 9

4-(3,4-Dimethoxyphenyl)-3-buten-2-one

To a solution of 3, 4-dimethoxybenzaldehyde (8.31 g, 50 mmol) in acetone (25 ml) and 95% ethanol (25 ml) was added water (200 ml) under stirring. During this time white precipitated solid was formed, and 10% sodium hydroxide aqueous solution (40 ml) was added dropwise under stirring below 10° C. Then the reaction mixture was stirred for 24 hr at room temperature, after the reaction completed, the reaction mixture was neutralized with 6N hydrochloric acid to adjust pH=7.0, the prepicitated yellow solid was collected by filtration and washed with ethanol, dried, then recrystallized from 95% ethanol to give 4.16 g of a pale yellow crystal, mp: 78-80° C., yield: 17.75%.

Preparation 10

4-(3-Methoxy-4-hydroxyphenyl)-3-buten-2-one

The title compound was prepared according to the method described in preparation 5, using 3-methoxy-4-hydroxybenzaldehyde as the starting material, mp: 126-128° C., yield: 48.9%.

Preparation 11

4-(2,4-Dichlorophenyl)-3-buten-2-one

The title compound was prepared according to the method described in preparation 1, using 2,4-dichlorobenzaldehyde as the starting material, yield: 60.84%.

Preparation 12

4-(4-Bromophenyl)-3-buten-2-one

The title compound was prepared according to the method described in preparation 1, using 4-bromobenzaldehyde as the starting material, mp 82-84° C., yield: 49.0%.

Preparation 13

4-(4-Methoxyphenyl)-3-buten-2-one

The title compound was prepared according to the method described in preparation 6, using 4-methoxybenzaldehyde as the starting material, mp: 93-95° C., yield: 95%.

Preparation 14

3,4-Methylenedioxy-5-methoxy-acetophenone 3,4-Methylenedioxy-5-methoxybenzoic acid (39.23 g, 0.2 mol) was dissolved in dry benzene, thionyl chloride 47.6 g (28.8 ml, 0.4 mol) was added under stirring, the resulting solution was refluxed for 15 hr, then the solvent and excessive thionyl chloride were removed by distillation under reduced pressure to give pure 3,4-methylenedioxy-5-methoxy-benzoyl chloride.

To the magnesium scraps (5.35 g, 0.22 mol) were added $CCl_4$ (2 ml) and anhydrous ethanol (6 ml). When the reaction started, anhydrous ether (170 ml) was added, then a solution of diethyl malonate (35.24 g, 0.22 mol) in anhydrous ether (28 ml) and anhydrous ethanol (28 ml) was added dropwise to the above reaction mixture under stirring, and the reaction solution was refluxing until no magnesium scraps left. The anhydrous ether solution of acyl chloride obtained above was added dropwise to the above reaction mixture under stirring, the reaction solution was continued under refluxing for 3 hr. After staying overnight, water (120 ml) and 20% $H_2SO_4$ were added until all solid redissolved. TLC showed no starting material was left. The ether layer was separated, water layer extracted with methylene chloride, the combined organic layers were washed with saturated sodium carbonate solution and saturated sodium chloride solution successively, dried over anhydrous sodium sulfate and the extract was evaporated under reduced pressure to give the crude product, which was recrystallized from 95% ethanol to give 20.12 g of a white crystal, mp: 81-82° C., yield: 50.8%.

Preparation 15

4-(3,4-Methylenedioxyphenyl)-3-buten-2-one

The title compound was prepared according to the method described in preparation 9, using 3,4-methylenedioxy benzaldehyde as the starting material, the title compound was obtained as a pale yellow sheet crystal, mp: 108-109° C., yield: 76.4%.

Preparation 16

4-(4-Trifluoromethylphenyl)-3-buten-2-one

The title compound was prepared according to the method described in preparation 1, using 4-trifluoromethylbenzaldehyde as the starting material.

Preparation 17

4-(4-Chlorophenyl)-3-penten-2-one

The title compound was prepared according to the method described in preparation 1, using 4-chlorobenzaldehyde as starting material to react with 2-butanone.

Preparation 18

4-(4-Fluorophenyl)-3-buten-2-one

The title compound was prepared according to the method described in preparation 1, using 4-fluorobenzaldehyde as the starting material.

Preparation 19

4-(4-Propoxyphenyl)-3-buten-2-one

The title compound was prepared according to the method described in preparation 1, using 4-propoxybenzaldehyde as the starting material.

Preparation 20

4-(3-Hydroxy-4-methoxyphenyl)-3-buten-2-one

The title compound was prepared according to the method described in preparation 1, using 3-hydroxy-4-methoxybenzaldehyde as the starting material.

Preparation 21

4-(4-n-Butoxyphenyl)-3-buten-2-one

The title compound was prepared according to the method described in preparation 1, using 4-n-butoxybenzaldehyde as the starting material.

Preparation 22

4-(4-Nitrophenyl)-3-buten-2-one

The title compound was prepared according to the method described in preparation 1, using 4-nitrobenzaldehyde as the starting material.

Preparation 23

4-(2,4-Dinitrophenyl)-3-buten-2-one

The title compound was prepared according to the method described in preparation 1, using 2,4-dinitrobenzaldehyde as the starting material.

Preparation 24

4-(3-Chlorophenyl)-3-buten-2-one

The title compound was prepared according to the method described in preparation 1, using 3-chlorobenzaldehyde as the starting material.

Preparation 25

3,4-Methylenedioxy-acetophenone

The title compound was prepared according to the method described in preparation 14, using 3,4-methylenedioxybenzoic acid as the starting material.

Preparation 26

4-Chloro-acetophenone

The title compound was prepared according to the method described in preparation 14, using 4-chlorobenzoic acid as the starting material.

Preparation 27

4-Phenyl-3-buten-2-one

The title compound was prepared according to the method described in preparation 1, using benzaldehyde as the starting material.

Preparation 28

4-(3-Methoxy-4-ethoxyphenyl)-3-penten-2-one

The title compound was prepared according to the method described in preparation 1, using 3-methoxy-4-ethoxybenzaldehyde as starting material to react with 2-butanone.

EXAMPLE

Example 1

5-[(4-Ethoxycarbonyl)piperidyl]-1-(4-hydroxyphenyl)-1-penten-3-one hydrochloride compound No. 1

0.426 g (2.2 mmol) of 4-ethoxycarbonylpiperidine hydrochloride and 0.6 g (20 mmol) of paraformaldehyde were dissolved in a mixture of anhydrous ethanol (10 ml) and concentrated hydrochloric acid (0.24 ml). The reaction mixture was refluxed and stirred for 30 min. After the solid was dissolved, 0.324 g (2.0 mmol) of 4-(4-hydroxyphenyl)-3-buten-2-one (prepared as described in preparation 2) was added to the above reaction mixture. The solution was further refluxed and stirred for 19 hr. TLC showed no starting material was left. After cooling by cold water bath to room temperature, the precipitated white solid was collected by filtration and then recrystallized from anhydrous ethanol and dried to give 0.267 g of white crystals, yield: 36.3%, mp: 190-193° C., $R_f$=0.69 ($CH_2Cl_2$: $CH_3OH$: HCOOH=3 ml: 10 d: 1 d).
$^1$HNMR δppm (DMSO-$d_6$): 1.20(t, 3H, J=7.0, $OCH_2CH_3$), 3.19-3.61 (m, 6H, $3NCH_2$), 3.98-4.22 (q, 2H, J=7.0, $\overline{COO}$ $CH_2CH_3$), 6.67(d, J=16.2 Hz, 1H, =CHCO), 6.83(d, J=8.5 $\overline{Hz}$, 2H, ArH), 7.60(d, J=8.5 Hz, 2H, ArH); 7.56(s, 1H, OH, $D_2O$ exchange); 7.62(d, J=16.2 Hz, 1H, CH=). MS (m/z): 331($M^+$, 6), 286($M^+$−45, 3), 175(90).

Example 2

5-[(4-Ethoxycarbonyl)piperidyl]-1-(4-cyanophenyl)-1-penten-3-one hydrochloride compound No. 2

0.426 g (2.2 mmol) of 4-ethoxycarbonylpiperidine hydrochloride and 0.6 g (20 mmol) of paraformaldehyde were dissolved in a mixture of anhydrous ethanol (10 ml) and concentrated hydrochloric acid (0.24 ml). The reaction mixture was refluxed and stirred for 20 min. After the solid was dissolved, 0.472 g (2.2 mmol) of 4-(4-cyanophenyl)-3-buten-2-one (prepared as described in preparation 8) was added to the above reaction mixture. The solution was further refluxed and stirred for 24 hr, after staying overnight at room temperature, the precipitated solid was collected by filtration and then recrystallized from anhydrous ethanol and dried to give 0.339 g of the title compound as needle crystals, yield: 46.7%, mp: 193-195° C. $R_f$=0.44 ($CH_2Cl_2$: $CH_3OH$: HCOOH=3ml: 10 d: 1 d);

$^1$HNMR δppm (DMSO-$d_6$): 1.20(t, 3H, J=7.0 Hz, $OCH_2$ $CH_3$), 3.20-3.60(m, 6H, $3NCH_2$), 3.98-4.22(q, 2H, J=7.0 Hz, $COOCH_2CH_3$), 6.69(d, J=16.2 Hz, 1H, =CHCO), 6.82(d, J=8.5 Hz, 2H, ArH), 7.59(d, J=8.5 Hz, 2H, ArH); 7.62(d, J=16.2 Hz, 1H, CH=). MS (m/z): 340($M^+$, 8), 295($M^+$–45, 4), 184(85).

Example 3

5-[(4-Ethoxycarbonyl)piperidyl]-1-(4-chlorophenyl)-1-penten-3-one hydrochloride compound No. 3

0.38 g (2.0 mmol) of 4-ethoxycarbonylpiperidine hydrochloride and 0.4 g (14 mmol) of paraformaldehyde were dissolved in a mixture of anhydrous ethanol (5 ml) and concentrated hydrochloric acid (0.2 ml). The reaction mixture was refluxed and stirred for 3 hr. After the solid was dissolved, 0.36 g (2.5 mmol) of 4-(4-chlorophenyl)-3-buten-2-one (prepared as described in preparation 1) was added to the above reaction mixture. The solution was further refluxed and stirred for 12 hr, after staying overnight at room temperature. TLC showed the reaction was completed, the precipitated solid was collected by filtration and then recrystallized from anhydrous ethanol and dried to give 0.45 g of the title compound as crystals, yield: 58%, mp 172-174° C.

$^1$HNMR δppm (DMSO-$d_6$): 1.153(t, 3H, J=7.0 Hz, $OCH_2$ $CH_3$), 1.83(br, 2H, $CH_2$), 2.01(m, 3H, $COCH_2$, CHCO), 2.57 (m, 2H, $CH_2$), 2.944(m, 2H, $NCH_2$), 3.298(m, 2H, $NCH_2$), 3.47(m, 2H, $CH_2N$), 4.05(q, 2H, J=7.0 Hz, $OCH_2CH_3$), 6.9(d, 1H, J=16.2 Hz, =CHCO), 7.49(d, 2H, J=8.5 Hz, ArH), 7.67 (d, 1H, J=16.2 Hz, CH=), 7.74(d, 2H, J=8.5 Hz, ArH); MS (m/z): 349.3($M^+$, 15), 304.2($M^+$–45, 9), 194.1($M^+$–156, 5), 192(17), 170.2(100), 169.2(59), 165(50), 157(40).

Example 4

5-[(4-Ethoxycarbonyl)piperidyl]-1-(3,4-dimethoxyphenyl)-1-penten-3-one hydrochloride compound No. 4

0.639 g (3.3 mmol) of 4-ethoxycarbonylpiperidine hydrochloride and 0.9 g (30 mmol) of paraformaldehyde were dissolved in a mixture of anhydrous ethanol (15 ml) and concentrated hydrochloric acid (0.34 ml). The reaction mixture was refluxed and stirred for 0.5 hr, after the solid was dissolved, 0.619 g (3 mmol) of 4-(3,4-dimethoxyphenyl)-3-buten-2-one (prepared as described in preparation 9) was added to the above reaction mixture. The solution was further refluxed and stirred for 5.5 hr, after staying overnight at room temperature, the reaction mixture was evaporated under reduced pressure to give a light yellow solid, filtered and then recrystallized from 95% ethanol to give 0.42 g of pale yellow crystals, yield: 33.9%, mp: 159-162° C.

$^1$HNMR δppm (DMSO-$d_6$): 1.19(t, 3H, J=7.2 Hz, $OCH_2$ $CH_3$), 3.20-3.60(m, 6H, $3NCH_2$), 3.78(s, 6H, $2OCH_3$), 3.98-4.22(q, 2H, J=7.2 Hz, $COOCH_2CH_3$), 6.65(d, J=16.2 Hz, 1H, =CHCO), 6.80(d, J=8.5 Hz, 1H, ArH), 7.57(d, J=8.5 Hz, 2H, ArH), 7.60(d, J=16.2 Hz, 1H, CH=). MS (m/z): 359($M^+$, 7), 314($M^+$–45, 3), 286($M^+$–73, 3), 202($M^+$–156, 100).

Example 5

5-[(4-Ethoxycarbonyl)piperidyl]-1-(3-methoxy-4-ethoxyphenyl)-1-penten-3-one hydrochloride Compound No. 5

0.639 g (3.3 mmol) of 4-ethoxycarbonylpiperidine hydrochloride and 0.9 g (30 mmol) of paraformaldehyde were dissolved in a mixture of anhydrous ethanol (15 ml) and concentrated hydrochloric acid (0.34 ml). The reaction mixture was refluxed and stirred for 0.5 hr, after the solid was dissolved, 0.661 g (3 mmol) of 4-(3-methoxy-4-ethoxyphenyl)-3-buten-2-one (prepared as described in preparation 6) was added to the above reaction mixture. The solution was further refluxed and stirred for 7 hr, after staying overnight at room temperature, the precipitated solid was collected by filtration and then recrystallized from 95% ethanol and dried to give 0.47 g of crystals, yield: 38.3%, mp: 175-177° C.

$^1$HNMR δppm (DMSO-$d_6$): 1.28(t, 3H, J=7.2 Hz, $OCH_2$ $CH_3$), 1.41(t, 3H, J=7.2 Hz, $COOCH_2CH_3$), 1.9-2.2(brs, 5H, $(CH_2)_2CH$), 3.20-3.60(m, 8H, $3NCH_2+COCH_2$), 3.9(s, 3H, $OCH_3$), 4.13(d, d, 4H, J=7.2 Hz, J=7.2 Hz, $COOCH_2CH_3$, $OCH_2CH_3$), 6.89(d, 1H, J=16.2 Hz =CHCO), 7.05(d, 1H, J=7.2 Hz, ArH), 7.22-7.48(m, 2H, ArH), 7.71(d, 1H, J=16.2 Hz, CH=). MS (m/z): 389($M^+$, 30), 360($M^+$–29, 3), 344 ($M^+$–45, 12), 316($M^+$–73, 4), 232(90).

Example 6

5-[(4-Ethoxycarbonyl)piperidyl]-1-(3,4,5-trimethoxyphenyl)-1-penten-3-one hydrochloride Compound No. 6

0.426 g (2.2 mmol) of 4-ethoxycarbonylpiperidine hydrochloride and 0.6 g (20 mmol) of paraformaldehyde were dissolved in anhydrous ethanol (10 ml). The pH value of the solution was adjusted to pH=2-3 with concentrated hydrochloric acid and the reaction mixture was refluxed and stirred for 20 min. After the solid was dissolved, 0.472 g (2.2 mmol) of 4-(3,4,5-Trimethoxyphenyl)-3-buten-2-one (prepared as described in preparation 7) was added to the above reaction mixture. The solution was further refluxed and stirred for 24 hr, after staying overnight at room temperature, the precipitated solid was collected by filtration and then recrystallized from anhydrous ethanol and dried to give 0.347 g of needle crystals, yield: 39.3%, mp: 176-178° C.

$^1$HNMR δppm (DMSO-$d_6$): 1.21(t, J=7.2 Hz, 3H, $COOCH_2CH_3$), 1.9-2.2(brs, 5H, $(CH_2)_2CH$), 3.20-3.61(m, 6H, $3NCH_2$), 3.72(s, 3H, $OCH_3$), 3.82(s, 6H, $2OCH_3$), 3.98-4.22(q, 2H, $COOCH_2CH_3$), 6.82(d, J=16.2 Hz, 1H, =CHCO), 7.08(s, 2H, ArH), 7.64(d, J=16.2 Hz, 1H, CH=). MS (m/z): 405($M^+$, 6), 360(2), 248(100), 217(60).

Example 7

5-[(4-Ethoxycarbonyl)piperidyl]-1-(3-ethoxy-4-hydroxyphenyl)-1-penten-3-one hydrochloride Compound No. 7

0.426 g (2.2 mmol) of 4-ethoxycarbonylpiperidine hydrochloride and 0.6 g (20 mmol) of paraformaldehyde were dissolved in anhydrous ethanol (15 ml). The pH value of the solution was adjusted to pH=2-3 with concentrated hydrochloric acid and the reaction mixture was refluxed and stirred for 2 hr. After the solid was dissolved, 0.412 g (2.0 mmol) of 4-(3-ethoxy-4-hydroxyphenyl)- 3-buten-2-one (prepared as described in preparation 5) was added to the above reaction mixture. The solution was further refluxed and stirred for 12 hr, after staying overnight at room temperature, the precipitated solid was collected by filtration and then recrystallized from 95% ethanol and dried to give 0.15 g of crystals, yield: 18.2%, mp: 155-157° C.

$^1$HNMR δppm (DMSO-d$_6$): 1.16(t, 3H, J=7.2 Hz, OCH$_2$CH$_3$), 1.22(t, 3H, J=7.2 Hz, COOCH$_2$CH$_3$), 1.9-2.2(brs, 5H, (CH$_2$)$_2$CH), 3.20-3.58(m, 6H, 3NCH$_2$), 4.04-4.13(q, 4H, J=7.2 Hz, COOCH$_2$CH$_3$, OCH$_2$CH$_3$), 6.76(d, J=16.0 Hz, 1H, =CHCO), 6.84(d, J=8.1 Hz, 1H, ArH), 7.16(d, J=8.1 Hz, 1H, ArH), 7.30(d, J=8.1 Hz 1H, ArH), 7.58(d, J=16.0 Hz, 1H, CH=).

FAB-MS (m/z): 376.5(M$^+$+1), 348.5(M$^+$−29+1).

Example 8

5-[(4-Ethoxycarbonyl)piperidyl]-1-(3-methoxy-4-hydroxyphenyl)-1-penten-3-one hydrochloride Compound No. 8

0.485 g (2.5 mmol) of 4-ethoxycarbonylpiperidine hydrochloride and 0.6 g (20 mmol) of paraformaldehyde were dissolved in anhydrous ethanol (5 ml ). The pH value of the solution was adjusted to pH=2-3 with concentrated hydrochloric acid and the reaction mixture was refluxed and stirred for 2 hr. After the solid was dissolved, 0.48 g (2.5 mmol) of 4-(3-methoxy-4-hydroxy phenyl)-3-buten-2-one (prepared as described in preparation 10) was added to the above reaction mixture. The solution was further refluxed and stirred for 12 hr. TLC showed the reaction was completed, after staying overnight at room temperature, the precipitated solid was collected by filtration and then recrystallized from 95% ethanol and dried to give 0.42 g of crystals, yield: 42%, mp: 194-197° C.

$^1$HNMR δppm (DMSO-d$_6$): 1.20(t, 3H, J=7.2 Hz, COOCH$_2$CH$_3$), 1.9-2.2(brs, 5H, (CH$_2$)$_2$CH), 3.20-3.58(m, 6H, 3NCH$_2$), 3.80(s, 3H, OCH$_3$), 4.06-4.12(q, 2H, J=7.2 Hz, COOCH$_2$CH$_3$), 6.76(d, J=16.0 Hz, 1H, =CHCO), 6.82(d, J=8.5 Hz 1H, ArH), 7.16(d, J=8.5 Hz, 1H, ArH), 7.31(d, J=1.5 Hz, 1H, ArH), 7.60(d, J=16.0 Hz, 1H, CH=). MS (m/z): 361(M$^+$, 20), 316(M$^+$−45, 10), 288 (M$^+$−73, 5), 204(M$^+$−157, 100).

Example 9

5-[(4-Ethoxycarbonyl)piperidyl]-1-(3-hydroxy-4-methoxyphenyl)-1-penten-3-one hydrochloride Compound No. 9

0.485 g (2.5 mmol) of 4-ethoxycarbonylpiperidine hydrochloride and 0.6 g (20 mmol) of paraformaldehyde were dissolved in anhydrous ethanol (5 ml). The pH value of the solution was adjusted to pH=2-3 with concentrated hydrochloric acid and the reaction mixture was refluxed and stirred for 2 hr. After the solid was dissolved, 0.48 g (2.5 mmol) of 4-(3-hydroxy-4-methoxyphenyl)-3-buten-2-one (prepared as described in preparation 20) was added to the above reaction mixture. The solution was further refluxed and stirred for 12 h. TLC showed the reaction was completed, after staying overnight at room temperature, the precipitated solid was collected by filtration and then recrystallized from 95% ethanol and dried to give 0.3 g of crystals, yield: 30%, mp: 187-190° C.

$^1$HNMR δppm (DMSO-d$_6$): 1.19(t, 3H, J=7.2 Hz, COOCH$_2$CH$_3$), 1.9-2.2(brs, 5H, (CH$_2$)$_2$CH), 3.21-3.57(m, 6H, 3NCH$_2$), 3.8(s, 3H, OCH$_3$), 4.07-4.14(q, 2H, J=7.2 Hz, COOCH$_2$CH$_3$), 6.62(d, J=16.0 Hz, 1H, =CHCO), 6.97(d, J=8.5 Hz, 1H, ArH), 7.15(d, J=8.5 Hz, 2H, ArH), 7.57(d, J=16.0 Hz, 1H, CH=). MS (m/z): 361(M$^+$, 15), 316(M$^+$−45, 3), 204(M$^+$−157, 100).

Example 10

5-[(4-Ethoxycarbonyl)piperidyl]-1-(2,4-dichlorophenyl)-1-penten-3-one hydrochloride Compound No. 10

0.426 g (2.2 mmol) of 4-ethoxycarbonylpiperidine hydrochloride and 0.6 g (20 mmol) of paraformaldehyde were dissolved in anhydrous ethanol (10 ml). The pH value of the solution was adjusted to pH=2-3 with concentrated hydrochloric acid and the reaction mixture was refluxed and stirred for 2 hr. After the solid was dissolved, 0.43 g (2.0 mmol) of 4-(2,4-dichlorophenyl)-3-buten-2-one (prepared as described in preparation 11) was added to the above reaction mixture. The solution was further refluxed and stirred for 17 hr, after staying overnight at room temperature, the precipitated solid was collected by filtration and then recrystallized from 95% ethanol and dried to give 0.461 g of crystals, yield: 54.8%, mp: 161-163° C.

$^1$HNMR δppm (DMSO-d$_6$): 1.2(t, 3H, J=7.2 Hz, COOCH$_2$CH$_3$), 1.90(m, 4H, 2CH$_2$), 3.0(m, 4H, 2NCH$_2$), 3.32-3.38(q, 4H, COCH$_2$CH$_2$N—), 3.52(br, 1H, HC—CO), 4.10(q, 2H, J=7.2 Hz, COOCH$_2$CH$_3$), 7.0(d, 1H, J=16.2 Hz, =CHCO), 7.48(d, d, 1H, J=9.0 Hz, 1.8 Hz, Ar—H), 7.73(d, 1H, J=1.8 Hz, ArH), 7.82(d, 1H, J=16.2 Hz, CH=), 7.95(d, 1H, J=9.0 Hz, Ar—H). MS (m/z): 383(M$^+$, 4), 338(M$^+$−45, 3), 227 (M$^+$−157, 5), 191(100).

Example 11

5-[(4-Ethoxycarbonyl)piperidyl]-1-(3,4-methylenedioxyphenyl)-1-penten-3-one hydrochloride Compound No. 11

1.08 g (6 mmol) of 4-ethoxycarbonylpiperidine hydrochloride and 0.9 g (30 mmol) of paraformaldehyde were dissolved in anhydrous ethanol (50 ml). The pH value of the solution was adjusted to pH=2-3 with concentrated hydrochloric acid and the reaction mixture was refluxed and stirred for 2 hr. After the solid was dissolved, 0.95 g (5 mmol) of 4-(3,4-methylenedioxyphenyl)-3-buten-2-one (prepared as described in preparation 15) was added to the above reaction mixture. The solution was further refluxed and stirred for 15 hr, after staying overnight at room temperature, the precipitated light yellow solid was collected by filtration and then recrystallized from anhydrous ethanol and dried to give 1.4 g of light yellow crystals, yield: 68%, mp: 192-194° C.

$^1$HNMR δppm (DMSO-d$_6$): 1.19(t, 3H, J=7.2 Hz, COOCH$_2$CH$_3$), 1.8-2.2(brm, 5H, (CH$_2$)$_2$CHCO—), 3.0-3.5 (brm, 8H, 3NCH$_2$+COCH$_2$), 4.05(q, 2H, COOCH$_2$CH$_3$), 6.0 (s, 2H, —OCH$_2$O—), 6.75(d, 1H, J=16.2 Hz, =CHCO), 7.0-7.35(m, 3H, ArH), 7.61(d, 1H, J=16.2 Hz, CH=).

MS (m/z): 359(M$^+$, 7), 314(M$^+$−45, 3), 286(M$^+$−73, 3), 202(M$^+$−156, 100).

Example 12

5-[(3-Ethoxycarbonyl)piperidyl]-1-(3-ethoxy-4-methoxyphenyl)-1-penten-3-one hydrochloride Compound No. 12

0.387 g (2.0 mmol) of 3-ethoxycarbonylpiperidine hydrochloride and 0.4 g (14 mmol) of paraformaldehyde were dissolved in anhydrous ethanol (5 ml). The pH value of the solution was adjusted to pH=2-3 with concentrated hydrochloric acid and the reaction mixture was refluxed and stirred for 2 hr. After the solid was dissolved, 0.44 g (2.0 mmol) of 4-(3-ethoxy-4-methoxyphenyl)-3-buten-2-one (prepared as described in preparation 4) was added to the above reaction mixture. The solution was further refluxed and stirred for 11 hr. TLC showed the reaction was completed, after staying overnight at room temperature, the precipitated solid was collected by filtration and then recrystallized from 95% ethanol and dried to give 0.26 g of crystals, yield: 30.1%, mp: 158-160° C.

$^1$HNMR δppm (DMSO-d$_6$): 1.21(t, 3H, J=7.2 Hz, OCH$_2$CH$_3$), 1.33(t, 3H, J=7.2 Hz, COOCH$_2$CH$_3$), 2.26-2.71(brs, 5H, (CH$_2$)$_2$CH), 3.30-3.40(m, 8H, 3NCH$_2$+COCH$_2$), 3.80(s, 3H, OCH$_3$), 4.10(d, d, 4H, J=7.2 Hz, J=7.2 Hz, COOCH$_2$CH$_3$, OCH$_2$CH$_3$), 6.82(d, 1H, J=16.2 Hz=CHCO), 7.02 (d, 1H, J=9.0 Hz, ArH), 7.27(d, J=8.1 Hz, 1H, ArH), 7.32(s, 1H, ArH), 7.63(d, 1H, J=16.2 Hz, CH=). MS (m/z): 389(M$^+$, 15), 344(M$^+$−45, 12), 232(M$^+$−156+H, 45), 316(M$^+$−73, 3).

Example 13

5-[(3-Ethoxycarbonyl)piperidyl]-1-(4-chloro)phenyl-1-penten-3-one hydrochloride Compound No. 13

0.387 g (2.0 mmol) of 3-ethoxycarbonylpiperidine hydrochloride and 0.4 g (14 mmol) of paraformaldehyde were dissolved in anhydrous ethanol (5 ml). The pH value of the solution was adjusted to pH=2-3 with concentrated hydrochloric acid and the reaction mixture was refluxed and stirred for 2 hr. After the solid was dissolved, 0.36 g (2.0 mmol) of 4-(4-chlorophenyl)-3-buten-2-one (prepared as described in preparation 1) was added to the above reaction mixture. The solution was further refluxed and stirred for 12 hr. TLC showed the reaction was completed. After staying overnight at room temperature, the precipitated solid was collected by filtration and then recrystallized from 95% ethanol and dried to give 0.42 g of crystals, yield: 54.4%, mp: 165-168° C.

$^1$HNMR δppm (DMSO-d$_6$): 1.18(t, 3H, J=7.2 Hz, COOCH$_2$CH$_3$), 1.90(m, 4H, 2CH$_2$), 3.0(m, 4H, 2NCH$_2$), 3.32-3.38(q, 4H, COCH$_2$CH$_2$N—), 3.52(br, 1H, HCCO), 4.095(q, 2H, J=7.2 Hz, COOCH$_2$CH$_3$), 6.87(d, 1H, J=16.2 Hz, =CHCO), 7.50(d, 2H, J=8.5 Hz, Ar—H), 7.75(d, 2H, J=8.5 Hz, ArH), 7.69(d, 1H, J=16.2 Hz, CH=). MS (m/z): 349(M$^+$, 12), 304(M$^+$−45, 6), 276(M$^+$−73, 4), 192(M$^+$−156, 5), 170(100).

Example 14

5-[(3-Ethoxycarbonyl)piperidyl]-1-(3-hydroxy-4-methoxyphenyl)-1-penten-3-one hydrochloride Compound No. 14

0.387 g (2.0 mmol) of 3-ethoxycarbonylpiperidine hydrochloride and 0.4 g (14 mmol) of paraformaldehyde were dissolved in anhydrous ethanol (5 ml). The pH value of the solution was adjusted to pH=2-3 with concentrated hydrochloric acid and the reaction mixture was refluxed and stirred for 2 hr. After the solid was dissolved, 0.384 g (2.0 mmol) of 4-(3-hydroxy-4-methoxyphenyl)-3-buten-2-one (prepared as described in preparation 20) was added to the above reaction mixture. The solution was further refluxed and stirred for 10 hr. TLC showed the reaction was completed. After staying overnight at room temperature, the precipitated solid was collected by filtration and then recrystallized from 95% ethanol and dried to give 0.35 g of crystals, yield: 35%, mp: 163-165° C.

$^1$HNMR δppm (DMSO-d$_6$): 1.18(t, 3H, J=7.2 Hz, COOCH$_2$CH$_3$), 1.91(m, 4H, 2CH$_2$), 3.2(m, 4H, 2NCH$_2$), 3.33-3.39(q, 4H, COCH$_2$CH$_2$N—), 3.51(br, 1H, HCCO), 3.63(s, 3H, OCH$_3$), 4.10(q, 2H, J=7.2 Hz, COOCH$_2$CH$_3$), 6.62(d, 1H, J=16.2 Hz, =CHCO), 6.97(d, 1H, J=8.1 Hz, Ar—H), 7.14(d, 2H, J=8.1 Hz, ArH), 7.56(d, 1H, J=16.2 Hz, CH=). MS (m/z): 361(M$^+$, 20), 316(M$^+$−45, 5), 204(M$^+$−157, 100).

Example 15

5-[(3-Ethoxycarbonyl)piperidyl]-1-(3,4-methylenedioxyphenyl)-1-penten-3-one hydrochloride Compound No. 15

0.387 g (2.0 mmol) of 3-ethoxycarbonylpiperidine hydrochloride and 0.4 g (14 mmol) of paraformaldehyde were dissolved in anhydrous ethanol (5 ml). The pH value of the solution was adjusted to pH=2-3 with concentrated hydrochloric acid and the reaction mixture was refluxed and stirred for 2 hr. After the solid was dissolved, 0.384 g (2.0 mmol) of 4-(3,4-methylenedioxy-phenyl)-3-buten-2-one (prepared as described in preparation 15) was added to the above reaction mixture. The solution was further refluxed and stirred for 11 hr. TLC showed the reaction was completed. After staying overnight at room temperature, the precipitated solid was collected by filtration and then recrystallized from 95% ethanol and dried to give 0.22 g of crystals, yield: 27.7%, mp: 165-167° C.

$^1$HNMR δppm (DMSO-d$_6$): 1.18(t, 3H, J=7.2 Hz, COOCH$_2$CH$_3$), 2.26-2.72(m, 4H, 2CH$_2$), 3.23-3.41(m, 6H, 3NCH$_2$), 4.12(q, 2H, J=7.2 Hz, COOCH$_2$CH$_3$), 6.09(s, 2H, OCH$_2$O), 6.79(d, 1H, J=16.2 Hz, =CHCO), 7.22(d, 2H, J=8.1 Hz, ArH), 7.41(s, 1H, ArH), 7.61(d, 1H, J=16.2 Hz, CH=). MS (m/z): 359(M$^+$, 25), 314((M$^+$−45, 5), 286(M$^+$−73, 4), 202(M$^+$−157, 65), 170(100).

Example 16

5-[(3-Ethoxycarbonyl)piperidyl]-1-(2,4-dichlorophenyl)-1-penten-3-one hydrochloride Compound No. 16

0.426 g (2.2 mmol) of 3-ethoxycarbonylpiperidine hydrochloride and 0.6 g (20 mmol) of paraformaldehyde were dissolved in anhydrous ethanol (10 ml). The pH value of the solution was adjusted to pH=2-3 with concentrated hydrochloric acid and the reaction mixture was refluxed and stirred until the solid was dissolved, 0.43 g (2.0 mmol) of 4-(2,4-dichlorophenyl)-3-buten-2-one (prepared as described in preparation 11) was added to the above reaction mixture. The solution was further refluxed and stirred for 16 hr. TLC showed the reaction was completed. After staying overnight at room temperature, the precipitated solid was collected by filtration and then recrystallized from anhydrous ethanol and dried to give 0.314 g of crystals, yield: 37.4%, mp: 174-176° C.

$^1$HNMR δppm (DMSO-d$_6$): 1.2(t, 3H, J=7.2 Hz, COOCH$_2$CH$_3$), 1.90(m, 4H, 2CH$_2$), 3.0(m, 4H, 2NCH$_2$), 3.32-3.38(q, 4H, COCH$_2$CH$_2$N—), 3.52(br, 1H, HCCO), 4.10(q, 2H, J=7.2 Hz, COOCH$_2$CH$_3$), 7.0(d, 1H, J=16.2 Hz, =CHCO), 7.48(d, d, 1H, J=9.0 Hz, J=1.8 Hz, Ar—H), 7.73(d, 1H, J=1.8

Hz, ArH), 7.82(d, 1H, J=16.2 Hz, CH=), 7.95(d, 1H, J=9.0 Hz, Ar—H). MS (m/z): 383(M$^+$, 16), 338(M$^+$−45, 10), 226 (M$^+$−156, 5).

Example 17

5-[(4-Benzyl)piperidyl]-1-(4-fluorophenyl)-1-penten-3-one hydrochloride Compound No. 17

0.635 g (3.0 mmol) of 4-benzylpiperidine hydrochloride and 0.9 g (30 mmol) of paraformaldehyde were dissolved in anhydrous ethanol (6 ml). The pH value of the solution was adjusted to pH=1.5-2.0 with concentrated hydrochloric acid and the reaction mixture was refluxed and stirred for 2 hr. After the solid was dissolved, 0.494 g (3.0 mmol) of 4-(4-fluorophenyl)-3-buten-2-one (prepared as described in preparation 18) was added to the above reaction mixture. The solution was further refluxed and stirred for 9 hr. After cooling with ice-water bath, the precipitated solid was collected by filtration and then recrystallized from anhydrous ethanol and dried to give 0.206 g of white crystals, yield: 17.7%, mp: 168-171° C.
$^1$HNMR δppm (DMSO-d$_6$): 1.68(m, 5H, (CH$_2$)$_2$CH—), 2.86(m, 6H, 2NCH$_2$, —CH$_2$-Ph), 3.2-3.4(m, 4H, CO(CH$_2$)$_2$N), 6.81(d, 1H, J=16.2 Hz, =CHCO), 7.21(m, 5H, ArH), 7.36(d, 2H, J=8.5 Hz, ArH), 7.65(d, 2H, J=8.5 Hz, ArH), 7.71(d, 1H, J=16.2 Hz, CH=). MS (m/z): 351(M$^+$, 4), 177(M$^+$−174, 28).

Example 18

5-[(4-Benzyl)piperidyl]-1-(4-bromophenyl)-1-penten-3-one hydrochloride Compound No. 18

0.25 g (1.18 mmol) of 4-benzylpiperidine hydrochloride and 0.3 g (10 mmol) of paraformaldehyde were dissolved in anhydrous ethanol (4 ml). The pH value of the solution was adjusted to pH=1.5-2.0 with concentrated hydrochloric acid and the reaction mixture was refluxed and stirred for 2 hr. After the solid was dissolved, 0.264 g (1.18 mmol) of 4-(4-bromophenyl)-3-buten-2-one (prepared as described in preparation 12) was added to the above reaction mixture. The solution was further refluxed and stirred for 16 hr. After cooling with ice-water bath, the precipitated white solid was collected by filtration and then recrystallized from anhydrous ethanol and dried to give 0.157 g of white crystals, yield: 29.7%, mp: 173-176° C.
$^1$HNMR δppm (DMSO-d$_6$): 1.68(m, 5H, (CH$_2$)$_2$CH—), 2.86 (m, 6H, 2NCH$_2$, —CH$_2$-Ph), 3.2-3.38(m, 4H, CO(CH$_2$)$_2$N), 6.81(d, 1H, J=16.2 Hz, =CHCO), 7.21(m, 5H, ArH), 7.36(d, 2H, J=8.5 Hz, ArH), 7.65(d, 2H, J=8.5 Hz, ArH), 7.71(d, 1H, J=16.2 Hz, CH=). MS (m/z): 401(M$^+$, 4), 226(M$^+$−175, 3), 191(M$^+$−175−35, 100).

Example 19

5-[(4-benzyl)piperidyl]-1-(4-methylphenyl)-1-penten-3-one hydrochloride Compound No. 19

0.66 g (3.17 mmol) of 4-benzylpiperidine hydrochloride and 0.95 g (31.6 mmol) of paraformaldehyde were dissolved in anhydrous ethanol (8 ml). The pH value of the solution was adjusted to pH=2-3 with concentrated hydrochloric acid and the reaction solution was refluxed and stirred for 2 hr. After the solid was dissolved, 0.507 g (3.17 mmol) of 4-(4-Methylphenyl)-3-buten-2-one (prepared as described in preparation 3) was added to the above reaction mixture. The solution was further refluxed and stirred for 16 hr. TLC showed the reaction was completed. The reaction solution was evaporated to dryness under reduced pressure, the precipitated light yellow solid was collected by filtration and then recrystallized from anhydrous ethanol and dried to give 0.453 g of white crystal, yield: 37.3%, mp: 187-190° C.
$^1$HNMR δppm (DMSO-d$_6$): 1.5(s, 3H, CH$_3$—), 2.3-2.5(m, 5H, (CH(CH$_2$)$_2$), 2.87(m, 6H, 2NCH$_2$, —CH$_2$-Ph), 3.2-3.34 (m, 4H, CO(CH$_2$)$_2$N), 6.83(d, 1H, J=16.2 Hz, =CHCO), 7.17(d, 2H, J=8.5 Hz, Ar—H), 7.29(m, 5H, ArH), 7.61(d, 2H, J=8.5 Hz, ArH), 7.68(d, 1H, J=16.2 Hz, CH=). FAB-MS m/z: 348.3(M+1).

Example 19a

5-[(4-Benzyl)piperidyl]-1-phenyl-1-penten-3-one Hydrochloride Compound No. 19a

The title compound was prepared according to the method described in Example 19, using 4-phenyl-3-buten-2-one (prepared as described in preparation 27) as the starting material. Mp 164-168° C.

Example 20

5-[(4-Benzyl)piperidyl]-1-(4-trifluoromethylphenyl)-1-penten-3-one hydrochloride Compound No. 20

0.635 g (3.0 mmol) of 4-benzylpiperidine hydrochloride and 0.9 g (30 mmol) of paraformaldehyde were dissolved in anhydrous ethanol (7 ml). The pH value of the solution was adjusted to pH=1.5-2.0 with concentrated hydrochloric acid and the reaction solution was refluxed and stirred for 2 hr. After the solid was dissolved, 0.644 g (3.0 mmol) of 4-(4-trifluoromethylphenyl)-3-buten-2-one (prepared as described in preparation 16) was added to the above reaction mixture. The solution was further refluxed and stirred for 13 hr. After cooling with ice-water bath, the precipitated white solid was collected by filtration and then recrystallized from anhydrous ethanol and dried to give 0.164 g of white crystals, yield: 12%, mp: 175-179° C.
$^1$HNMR δppm (DMSO-d$_6$): 1.68(m, 5H, (CH$_2$)$_2$CH—), 2.87(m, 6H, 2NCH$_2$, —CH$_2$-Ph), 3.2-3.4(m, 4H, CO(CH$_2$)$_2$N), 6.99(d, 1H, J=16.2 Hz, =CHCO), 7.20(m, 5H, ArH), 7.65(d, 2H, J=8.5 Hz, ArH), 7.86(d, 2H, J=8.5 Hz, ArH), 7.89(d, 1H, J=16.2 Hz, CH=). MS (m/z): 401(M$^+$, 6), 227(M$^+$−174, 32).

Example 21

5-[(4-Benzyl)piperidyl]-1-(3,4-methylenedioxyphenyl)-1-penten-3-one hydrochloride Compound No. 21

1.08 g (5.0 mmol) of 4-benzylpiperidine hydrochloride and 1.5 g (50 mmol) of paraformaldehyde were dissolved in anhydrous ethanol (50 ml). The pH value of the solution was adjusted to pH=1.5- 2.0 with concentrated hydrochloric acid and the reaction mixture was refluxed and stirred for 1 hr. After the solid was dissolved, 1.9 g (10.0 mmol) of 4-(3, 4-methylenedioxyphenyl)-3-buten-2-one (prepared as described in preparation 15) was added to the above reaction mixture. The solution was further refluxed and stirred for 15 hr. After cooling with ice-water bath, the precipitated pale yellow solid was collected by filtration and then recrystallized from anhydrous ethanol and dried to give 1.40 g of pale yellow crystals, yield: 68.0%, mp: 175-178° C.

¹HNMR δppm (DMSO-d₆): 2.88(m, 2H, CH₂Ph), 3.25-3.60(m, 8H, 3NCH₂+COCH₂), 6.04(s, 2H, OCH₂O), 6.71(d, J=16.2 Hz, 1H, =CHCO), 6.92(d, J=7.2 Hz, 1H, ArH), 7.17-7.20(m, 6H, Ar(b)5H+Ar(a)H), 7.31(d, J=1.8 Hz, 1H, ArH), 7.57(d, J=16.2 Hz, 1H, CH=). MS (m/z): 377(M⁺, 12), 286 (2), 202(23).

Anal. Cald. for C₂₂H₃₁N₂O₅Cl: C, 69.64%; H, 6.82%; N, 3.38%. Found: C, 69.35%; H, 6.79%; N, 3.40%.

Example 22

5-[(4-Benzyl)piperidyl]-1-(4-butoxyphenyl)-1-penten-3-one hydrochloride Compound No. 22

0.423 g (2.0 mmol) of 4-benzylpiperidine hydrochloride and 0.6 g (20 mmol) of paraformaldehyde were dissolved in anhydrous ethanol (8 ml ). The pH value of the solution was adjusted to pH=1.5-2.0 with concentrated hydrochloric acid and the reaction mixture was refluxed and stirred for 0.5 hr. After the solid was dissolved, 0.436 g (2.0 mmol) of 4-(4-butoxyphenyl)-3-buten-2-one (prepared as described in preparation 21) was added to the above reaction mixture. The solution was further refluxed and stirred for 20 hr. TLC showed the reaction was completed. After cooling with ice-water bath, the precipitated white solid was collected by filtration and then recrystallized from anhydrous ethanol and dried to give 0.18 g of white crystals, yield: 20%, mp: 182-184° C.

¹HNMR δppm (DMSO-d₆): 0.96(t, J=7.2 Hz, 3H, CH₃CH₂—), 1.4-1.8(m, 4H, —(CH₂)₂), 2.87(m, 6H, 2NCH₂, =CH₂-Ph), 3.2-3.4(m, 4H, CO(CH₂)₂N), 4.03(t, J=7.2 Hz, 2H, —CH₂O), 6.73(d, 1H, J=16.2 Hz, =CHCO), 7.02(d, 2H, J=8.5 Hz, Ar—H), 7.21(m, 5H, ArH), 7.63(d, 2H, J=8.5 Hz, ArH), 7.68(d, 1H, J=16.2 Hz, CH=). MS (m/z): 405(M⁺, 4), 230(M⁺−175, 100).

Example 22a

5-[(4-Benzyl)piperidyl]-1-(4-methoxyphenyl)-1-penten-3-one hydrochloride Compound No. 22a The title compound was prepared according to the method described in Example 22, using 4-(4-methoxyphenyl)-3-buten-2-one (prepared as described in preparation 13) as the starting material. Mp: 180-184° C.

¹HNMR δppm (DMSO-d₆): 2.87(m, 6H, 2NCH₂, —CH₂-Ph), 3.2-3.4(m, 4H, CO(CH₂)₂N), 3.80(s, 3H, OCH₃), 6.88(d, 1H, J=15.9 Hz, =CHCO), 7.02(d, 2H, J=8.5 Hz, Ar—H), 7.22(m, 5H, ArH), 7.62(d, 2H, J=8.5 Hz, ArH), 7.69(d, 1H, J=15.9 Hz, CH=).

MS (m/z): 363.4(M⁺, 17), 188.2(M⁺−175, 100), 175.2 (M⁺−188, 56).

Example 22b

5-[(4-Benzyl)piperidyl]-1-(4-propoxyphenyl)-1-penten-3-one hydrochloride Compound No. 22b The title compound was prepared according to the method described in Example 22, using 4-(4-propoxyphenyl)-3-buten-2-one (prepared as described in preparation 19) as starting material. Mp: 187-189° C.

Example 22c

5-[(4-Benzyl)piperidyl]-1-phenyl-1-penten-3-one hydrochloride Compound No. 22c

The title compound was prepared according to the method described in Example 22, using 4-phenyl-3-buten-2-one (prepared as described in preparation 27) as the starting material. Mp: 164-168° C. 3.4(m, 4H, CO(CH₂)₂N), 6.88(d, 1H, J=6.9 Hz, ArH), 6.93(d, 1H, J=16.5 Hz, =CHCO), 7.18(d, 2H, J=7.8 Hz, Ar—H), 7.26(m, 5H, ArH), 7.66(d, 2H, J=8.5 Hz, ArH), 7.69(d, 1H, J=16.5 Hz, CH=).

MS (m/z): 333.4(M⁺, 42), 188.3(M⁺−175, 100), 175.3 (M⁺−188, 36).

Example 23

5-[(4-Benzyl)piperidyl]-1-(2,4-dichlorophenyl)-1-penten-3-one hydrochloride Compound No. 23

0.466 g (2.2 mmol) of 4-benzylpiperidine hydrochloride and 0.6 g (20 mmol) of paraformaldehyde were dissolved in anhydrous ethanol (8 ml ). The pH value of the solution was adjusted to pH=1.5-2.0 with concentrated hydrochloric acid and the reaction mixture was refluxed and stirred for 0.5 hr. After the solid was dissolved, 0.43 g (2.0 mmol) of 4-(2,4-dicholorophenyl)-3-buten-2-one (prepared as described in preparation 11) was added to the above reaction mixture. The solution was further refluxed and stirred for 20 hr. After cooling with ice-water bath, the precipitated white solid was collected by filtration and then recrystallized from anhydrous ethanol and dried to give 0.22 g of white crystals, yield: 25%, mp: 174-176° C.

¹HNMR δppm (DMSO-d₆): 2.87(m, 6H, 2NCH₂, —CH₂-Ph), 3.2-3.35(m, 4H, CO(CH₂)₂N), 6.97(d, 1H, J=16.2 Hz, =CHCO), 7.21(m, 5H, ArH), 7.48(q, 1H, J=9.0 Hz, ArH), 7.73(d, 1H, J=3.0 Hz, ArH), 7.79(d, 1H, J=16.2 Hz, CH=), 7.95 (d, 1H, J=9.0 Hz, ArH). MS (m/z): 401(M⁺, 4), 226(M⁺−175, 3), 191(M⁺−175-35, 100).

Example 24

5-[(N₄-Ethoxycarbonyl)piperazyl]-1-(4-hydroxyphenyl)-1-penten-3-one hydrochloride Compound No. 24

0.59 g (3.0 mmol) of N₄-ethoxycarbonylpiperizine hydrochloride and 0.9 g (30 mmol) of paraformaldehyde were dissolved in anhydrous ethanol (30 ml ). The pH value of the solution was adjusted to pH=1.5-2.0 with concentrated hydrochloric acid and the reaction mixture was refluxed and stirred for 2 hr. After the solid was dissolved, 0.49 g (3.0 mmol) of 4-(4-hydroxyphenyl)-3-buten-2-one (prepared as described in preparation 2) was added to the above reaction mixture. The solution was further refluxed and stirred for 20 hr. After cooling with ice-water bath, the precipitated pale yellow solid was collected by filtration and then recrystallized from anhydrous ethanol and dried to give 0.52 g of white crystals, yield: 47.3%, mp: 207-209° C.

¹HNMR δppm (DMSO-d₆): 1.20(t, 3H, J=7.2 Hz, COOCH₂CH₃), 3.22-3.47(m, 10H, 5NCH₂), 3.96-4.24(m, 4H, COOCH₂CH₃+COCH₂), 6.68(d, 1H, J=16.2 Hz, =CHCO), 6.84(d, 2H, J=8.1 Hz, ArH$_{AA'}$), 7.59(d, 2H, J=8.1 Hz, ArH$_{BB'}$), 7.61(d, 1H, J=16.2 Hz, CH=). MS (m/z): 332 (M⁺, 9), 287(2), 174(65), 147(85).

Example 24a

5-[(N₄-Ethoxycarbonyl)piperazyl]-1-(4-n-butoxyphenyl)-1-penten-3-one hydrochloride Compound No. 24a The title compound was prepared according to the method described in Example 24, using 4-(4-n-butoxyphenyl)-3- buten-2-one (prepared as described in preparation 21) as the starting material. Mp: 163-165° C.

Example 25

5-[(N$_4$-Ethoxycarbonyl)piperazyl]-1-(3-methoxy-4-ethoxyphenyl)-1-penten-3-one hydrochloride Compound No. 25

0.59 g (3.0 mmol) of N$_4$-ethoxycarbonylpiperizine hydrochloride and 0.9 g (30 mmol) of paraformaldehyde were dissolved in anhydrous ethanol (30 ml). The pH value of the solution was adjusted to pH=1.5-2.0 with concentrated hydrochloric acid and the reaction mixture was refluxed and stirred for 2 hr. After the solid was dissolved, 0.66 g (3.0 mmol) of 4-(3-methoxy-4-ethoxyphenyl)-3-buten-2-one (prepared as described in preparation 4) was added to the above reaction mixture. The solution was further refluxed and stirred for 20 hr. After cooling by ice-water bath, the precipitated pale yellow solid was collected by filtration and then recrystallized from anhydrous ethanol and dried to give 0.74 g of white crystals, yield: 57.8%, mp: 169-171° C.
$^1$HNMR δppm (DMSO-d$_6$): 1.22(t, 3H, J=7.2 Hz, COOCH$_2$CH$_3$), 1.36(t, J=7.2 Hz, 3H, OCH$_2$CH$_3$), 3.20-3.60 (m, 10H, 5NCH$_2$), 3.81(s, 3H, OCH$_3$), 4.08(m, 6H, COO CH$_2$CH$_3$+OCH$_2$CH$_3$+COCH$_2$), 6.78(d, 1H, J=16.2 Hz, =CHCO), 6.97(d, 1H, J=8.1 Hz, ArH), 7.26(d, 1H, J=8.1 Hz, ArH), 7.32(s, 1H, ArH), 7.64(d, 1H, J=16.2 Hz, CH=). MS (m/z): 390(M$^+$, 32), 345(4), 288 (8), 232(52), 203(38).

Example 26

5-[(N$_4$-Ethoxycarbonyl)piperazyl]-1-(3-ethoxy-4-hydroxyphenyl)-1-penten-3-one hydrochloride Compound No. 26

0.59 g (3.0 mmol) of N$_4$-ethoxycarbonylpiperizine hydrochloride and 0.9 g (30 mmol) of paraformaldehyde were dissolved in anhydrous ethanol (30 ml). The pH value of the solution was adjusted to pH=1.5-2.0 with concentrated hydrochloric acid and the reaction mixture was refluxed and stirred for 2.0 hr. After the solid was dissolved, 0.43 g (2.0 mmol) of 4-(3-ethoxy-4-hydroxyphenyl)-3-buten-2-one (prepared as described in preparation 5) was added to the above reaction mixture. The solution was further refluxed and stirred for 20 hr. TLC showed the reaction was completed, the reaction solution was evaporated to 5 ml under reduced pressure, the precipitated pale yellow solid was collected by filtration and then recrystallized from anhydrous ethanol and dried to give 0.75 g of pale yellow crystals, yield: 60.5%, mp: 175-178° C.
$^1$HNMR δppm (DMSO-d$_6$): 1.22(t, 3H, J=7.2 Hz, COOCH$_2$CH$_3$), 1.36(t, 3H, J=7.2 Hz, OCH$_2$CH$_3$), 3.00-3.60 (m, 10H, 5NCH$_2$), 3.88-4.24(m, 6H, COOCH$_2$CH$_3$+O CH$_2$CH$_3$+COCH$_2$), 6.71(d, 1H, J=16.2 Hz, =CHCO), 6.85 (d, 1H, J=8.1 Hz, ArH), 7.14(dd, 1H, J=8.1 Hz, J=1.8 Hz, ArH), 7.28(d, 1H, J=1.8 Hz, ArH), 7.59(d, 1H, J=16.2 Hz, CH=). MS (m/z): 376(M$^+$, 15), 331(1), 218(83).

Example 26a

5-[(N$_4$-Ethoxycarbonyl)piperazyl]-1-(3,4-dimethoxyphenyl)-1-penten-3-one hydrochloride Compound No. 26a The title compound was prepared according to the method described in Example 26, using 4-(3,4-dimethoxyphenyl)-3-buten-2-one (prepared as described in preparation 9) as the starting material. Mp: 206-209° C.

Example 26 b

5-[(N$_4$-Ethoxycarbonyl)piperazyl]-1-(3-methoxy-4-ethoxyphenyl)-1-penten-3-one hydrochloride Compound No. 26 b The title compound was prepared according to the method described in Example 26, using 4-(3-methoxy-4-ethoxyphenyl)-3-buten-2-one (prepared as described in preparation 6) as the starting material. Mp: 169-171° C.

Example 27

5-[(N$_4$-Ethoxycarbonyl)piperazyl]-1-(4-chlorophenyl)-1-penten-3-one hydrochloride Compound No. 27

0.428 g (2.2 mmol) of N$_4$-ethoxycarbonylpiperizine hydrochloride and 0.6 g (20 mmol) of paraformaldehyde were dissolved in anhydrous ethanol (10 ml). The pH value of the solution was adjusted to pH=1.5-2.0 with concentrated hydrochloric acid and the reaction mixture was refluxed and stirred for 1 hr. After the solid was dissolved, 0.36 g (2.0 mmol) of 4-(4-chlorophenyl)-3-buten-2-one (prepared as described in preparation 1) was added to the above reaction mixture. The solution was further refluxed and stirred for 36 hr. After cooling with water bath to room temperature, the precipitated white solid was collected by filtration and then recrystallized from anhydrous ethanol and dried to give 0.32 g of white crystals, yield: 41.4%, mp: 173-176° C.
$^1$HNMR δppm (DMSO-d$_6$): 1.20(t, 3H, J=7.2 Hz, COOCH$_2$CH$_3$), 2.80-3.60(m, 10H, 5CH$_2$N), 3.92-4.24(m, 4H, COCH$_2$+COOCH$_2$CH$_3$), 6.90(d, 1H, J=16.2 Hz, =CHCO), 7.48(d, 2H, J=8.1 Hz, ArH$_{AA'}$), 7.64(d, 1H, J=16.2 Hz, CH=), 7.76(d, 2H, J=8.1 Hz, ArH$_{BB'}$). MS (m/z): 350 (M$^+$, 40), 305(M$^+$−45, 5), 192(M$^+$−157, 10), 171(100).

Example 27a

5-[(N$_4$-Ethoxycarbonyl)piperazyl]-1-(4-fluorophenyl)-1-penten-3-one hydrochloride Compound No. 27a The title compound was prepared according to the method described in Example 27, using 4-(4-fluorophenyl)-3-buten-2-one (prepared as described in preparation 18) as the starting material. Mp: 177-180° C.
$^1$HNMR δppm (DMSO-d$_6$): 1.20(t, 3H, J=7.2 Hz, COOCH$_2$CH$_3$), 2.80-3. 60(m, 10H, 5CH$_2$N), 3.91-4.243(m, 4H, COCH$_2$+COOCH$_2$CH$_3$), 6.89(d, 1H, J=16.5 Hz, =CHCO), 7.31(d, 2H, J=8.7 Hz, ArH$_{AA'}$), 7.70(d, 1H, J=16.5 Hz, CH=), 7.84(d, J=8.7 Hz, 2H, ArH$_{BB'}$).

Example 27b

5-[(N$_4$-Ethoxycarbonyl)piperazyl]-1-(4-cyanophenyl)-1-penten-3-one hydrochloride Compound No. 27b The title compound was prepared according to the method described in Example 27, using 4-(4-cyanophenyl)-3-buten-2-one (prepared as described in preparation 8) as the starting material. Mp: 198-200° C.
MS (m/z): 333.4 (M$^+$, 46), 289.3 (M$^+$−45, 7), 171.2 (100).

Example 28

5-[(N$_4$-Ethoxycarbonyl)piperazyl]-1-(3,4,5-trimethoxy)phenyl-1-penten-3-one hydrochloride Compound No. 28

0.29 g (1.5 mmol) of N$_4$-ethoxycarbonylpiperizine hydrochloride and 0.6 g (20 mmol) of paraformaldehyde were dissolved in anhydrous ethanol (15 ml). The pH value of the solution was adjusted to pH=1.5-2.0 with concentrated hydrochloric acid and the reaction mixture was refluxed and stirred for 2 hr. After the solid was dissolved, 0.35 g (3.0 mmol) of 4-(3,4,5-trimethoxyphenyl)-3-buten-2-one (prepared as described in preparation 7) was added to the above reaction mixture. The solution was further refluxed and stirred for 15 hr. TLC showed the reaction was completed, the reaction solution was evaporated to 5 ml under reduced pressure, the precipitated pale yellow solid was collected by filtration and then recrystallized from anhydrous ethanol and dried to give 0.25 g of white crystals, yield: 37.9%, mp: 170-172° C.

$^1$HNMR δppm (DMSO-d$_6$): 1.22(t, 3H, J=7.2 Hz, COOCH$_2$CH$_3$), 3.00-3.60(m, 10H, 5NCH$_2$), 3.72(s, 3H, OCH$_3$), 3.84(s, 6H, 2OCH$_3$), 4.08(m, 4H, COOCH$_2$CH$_3$+COCH$_2$), 6.89(d, J=16.2 Hz, 1H, =CHCO), 7.05 (s, 2H, ArH), 7.65(d, J=16.2 Hz, 1H, CH=). MS (m/z): 406(M$^+$, 41), 361(4), 304(5), 248(100).

Example 29

5-[(N$_4$-Ethoxycarbonyl)piperazyl]-1-(4-trifluoromethylphenyl)-1-penten-3-one hydrochloride Compound No. 29

0.195 g (1.0 mmol) of N$_4$-ethoxycarbonylpiperizine hydrochloride and 0.3 g (10 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 2 hr. After the solid was dissolved, 0.214 g (1.0 mmol) of 4-(4-trifluoromethylphenyl)-3-buten-2-one (prepared as described in preparation 16) was added to the above reaction mixture. The solution was further refluxed and stirred for 12h. TLC showed the reaction was completed, the precipitated pale yellow solid was collected by filtration and then recrystallized from anhydrous ethanol and dried to give 0.115 g of white crystals, yield: 35.5%, mp: 197-198° C.

$^1$HNMR δppm (DMSO-d$_6$): 1.191(t, 3H, J=7.2 Hz, COOCH$_2$CH$_3$), 3.27-3.49(m, 10H, 5NCH$_2$), 4.08(q, 4H, COOCH$_2$CH$_3$+COCH$_2$—), 7.044(d, 1H, J=16.2 Hz, =CHCO), 7.79(d, 1H, J=16.2 Hz, CH=), 7.81(d, 2H, J=8.1 Hz, ArH$_{AA'}$), 7.95(d, 2H, J=8.1 Hz, ArH$_{BB'}$). FAB-MS (m/z): 386.3(M$^+$+1), 342.4(M$^+$−45+1), 171.4(M$^+$−213).

Example 30

5-[(N$_4$-Ethoxycarbonyl)piperazyl]-1-(4-bromophenyl)-1-penten-3-one hydrochloride Compound No. 30

0.215 g (1.1mmol) of N$_4$-ethoxycarbonylpiperizine hydrochloride and 0.3 g (10 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 2.0 hr. After the solid was dissolved, 0.225 g (1.0 mmol) of 4-(4-bromphenyl)-3-buten-2-one (prepared as described in preparation 12) was added to the above reaction mixture. The solution was further refluxed and stirred for 12 hr, the precipitated pale yellow solid was collected by filtration and then recrystallized from anhydrous ethanol and dried to give 0.152 g of white crystals, yield: 30.0%, mp: 163-165° C.

$^1$HNMR δppm (DMSO-d$_6$): 1.23(t, 3H, J=7.2 Hz, COOCH$_2$CH$_3$), 3.08-3.63(m, 10H, 5NCH$_2$), 3.96-4.22(m, 4H, COOCH$_2$CH$_3$++COCH$_2$), 6.71(d, 1H, J=16.2 Hz, =CHCO), 6.89(d, 2H, J=7.2 Hz, ArH), 7.62(d, 2H, J=7.2 Hz, ArH), 7.65(d, 1H, J=16.2 Hz, CH=). MS (m/z): 395(M$^+$, 12), 350(M$^+$−45, 6), 227(M$^+$−157, 35).

Example 31

5-[(N$_4$-Ethoxycarbonyl)piperazyl]-1-(2,4-dichlorophenyl)-1-penten-3-one hydrochloride Compound No. 31

0.428 g (2.2 mmol) of N4-ethoxycarbonylpiperizine hydrochloride and 0.6 g (20 mmol) of paraformaldehyde were dissolved in anhydrous ethanol (15 ml). The pH value of the solution was adjusted to pH=4.5-5.0 with concentrated hydrochloric acid and the reaction mixture was refluxed and stirred for 2.0 hr. After the solid was dissolved, 0.43 g (2.0 mmol) of 4-(2,4-dichlorophenyl)-3-buten-2-one (prepared as described in preparation 11) was added to the above reaction mixture. The solution was further refluxed and stirred for 18 hr. After cooling with cold water bath, the precipitated pale yellow solid was collected by filtration and then recrystallized from anhydrous ethanol and dried to give 0.219 g of white crystals, yield: 25.9%, mp: 169-171° C.

$^1$HNMR δppm (DMSO-d$_6$): 1.2(t, 3H, J=7.2, COOCH$_2$CH$_3$), 3.0(m, 10H, 5NCH$_2$), 3.32-3.38(q, 2H, COCH$_2$), 4.10 (q, 2H, J=7.2 Hz, COOCH$_2$CH$_3$), 6.96(d, 1H, J=16.2 Hz, =CHCO), 7.48(dd, 1H, J=9.0 Hz, J=1.8 Hz, Ar—H), 7.68(d, 1H, J=1.8 Hz, ArH), 7.82(d, 1H, J=16.2 Hz, CH=), 7.95(d, 1H, J=9.0 Hz, Ar—H). MS (m/z): 384(M$^+$, 6), 339(M$^+$−45, 3), 311(M$^+$−73, 3), 226(M$^+$−158, 3), 191(M$^+$−158, 70).

Example 32

5-[(N$_4$-Ethoxycarbonyl)piperazyl]-1-(3,4-methylenedioxyphenyl)-1-penten-3-one hydrochloride Compound No. 32

0.59 g (3.0 mmol) of N$_4$-ethoxycarbonylpiperizine hydrochloride and 0.9 g (30 mmol) of paraformaldehyde were dissolved in anhydrous ethanol (30 ml). The pH value of the solution was adjusted to pH=4.5-5.0 with concentrated hydrochloric acid and the reaction mixture was refluxed and stirred for 2 hr. After the solid was dissolved, 0.57 g (3.0 mmol) of 4-(3,4-methylenedioxyphenyl)-3-buten-2-one (prepared as described in preparation 15) was added to the above reaction mixture. The solution was further refluxed and stirred for 20 hr. TLC showed the reaction was completed, the reaction solution was evaporated to 5 ml under reduced pressure, the precipitated pale yellow solid was collected by filtration and then recrystallized from anhydrous ethanol and dried to give 0.81 g of pale yellow crystals, yield: 66.2%, mp: 191-194° C.

$^1$HNMR δppm (DMSO-d$_6$): 1.21(t, J=7.2 Hz, 3H, COOCH$_2$CH$_3$), 3.24-3.37(m, 10H, 5NCH$_2$), 4.09(q, J=7.2 Hz, 2H, COOCH$_2$CH$_3$), 4.10(s, 2H, COCH$_2$), 6.08(s, 2H, OCH$_2$O), 6.76(d, J=16.2 Hz, 1H, =CHCO), 6.96(d, J=8.1 Hz, 1H, ArH), 7.21(dd, J=7.2 Hz, J=1.8 Hz, 1H, ArH), 7.34(d, J=1.8 Hz, 1H, ArH), 7.60(d, J=16.2 Hz, 1H, CH=).

MS (m/z): 360(M$^+$, 22), 315(2), 202(68).

Example 33

5-[($N_4$-Ethoxycarbonyl)piperazyl]-1-(2,4-dinitrophenyl)-1-penten-3-one hydrochloride Compound No. 33

0.195 g (1.0 mmol) of $N_4$-ethoxycarbonylpiperizine hydrochloride and 0.3 g (10 mmol) of paraformaldehyde were dissolved in anhydrous ethanol (15 ml). The pH value of the solution was adjusted to pH=1.5-2.0 with concentrated hydrochloric acid and the reaction mixture was refluxed and stirred for 2 hr. After the solid was dissolved, 0.24 g (1.0 mmol) of 4-(2,4-dinitrophenyl)-3-buten-2-one (prepared as described in preparation 23) was added to the above reaction mixture. The solution was further refluxed and stirred for 11 hr, the reaction solution was evaporated to 5 ml under reduced pressure, the precipitated pale yellow solid was collected by filtration and then recrystallized from anhydrous ethanol and dried to give 0.06 g of white crystals, yield: 13.6%, mp: 146-147° C.

$^1$HNMR δppm (DMSO-$d_6$): 1.20(t, 3H, J=7.2 Hz, COOCH$_2$CH$_3$), 3.22-3.80(m, 10H, 5NCH$_2$), 3.92-4.20(m, 4H, COOCH$_2$CH$_3$+COCH$_2$), 7.04(d, 1H, J=16.2 Hz, =CHCO), 7.88(d, 1H, J=16.2 Hz, CH=), 8.16(d, 1H, J=8.1 Hz, ArH), 8.52(d, 1H, J=8.1 Hz, J=1.8 Hz, ArH), 8.76(d, 1H, J=1.8 Hz, ArH). MS (m/z): 332(M$^+$, 9), 287(2), 174(65), 147(85).

Example 34

5-[($N_4$-ethoxycarbonyl)piperazyl]-1-(3-methoxy-4-ethoxyphenyl)-1-penten-3-one hydrochloride Compound No. 34

0.59 g (3.0 mmol) of $N_4$-ethoxycarbonylpiperizine hydrochloride and 0.9 g (30 mmol) of paraformaldehyde were dissolved in anhydrous ethanol (30 ml). The pH value of the solution was adjusted to pH=1.5-2.0 with concentrated hydrochloric acid and the reaction mixture was refluxed and stirred for 2 hr. After the solid was dissolved, 0.66 g (3.0 mmol) of 4-(3-methoxy-4-ethoxyphenyl)-3-buten-2-one (prepared as described in preparation 6) was added to the above reaction mixture. The solution was further refluxed and stirred for 20 hr. The reaction solution was evaporated to 5 ml under reduced pressure, the precipitated pale yellow solid was collected by filtration and then recrystallized from anhydrous ethanol and dried to give 0.78 g of white crystals, yield: 61.0%, mp: 120-123° C.

$^1$HNMR δppm (DMSO-$d_6$): 1.20(t, 3H, J=7.2 Hz, COOCH$_2$CH$_3$), 1.36(t, 3H, J=7.2 Hz, OCH$_2$CH$_3$), 3.08-3.68 (m, 10H, 5NCH$_2$), 3.81(s, 3H, OCH$_3$), 3.96-4.24(m, 6H, COOCH$_2$CH$_3$+OCH$_2$CH$_3$+COCH$_2$), 6.82(d, 1H, J=16.2 Hz, =CHCO), 7.00(d, 1H, J=8.1 Hz, ArH), 7.29(d, 1H, J=8.1 Hz, ArH), 7.31(s, 1H, ArH), 7.62(d, 1H, J=16.2 Hz, CH=). MS (m/z): 390(M$^+$, 9), 345(1), 232(36), 203(13).

Anal. Cald. for $C_{21}H_{31}N_2O_5Cl\cdot\frac{1}{4}H_2O$: C, 58.46%; H, 7.36%; N, 6.49%. Found: C, 58.33%; H, 7.14%; N, 6.36%.

Example 34a

5-[($N_4$-Ethoxycarbonyl)piperazyl]-1-(4-cyanophenyl)-1-penten-3-one hydrochloride Compound No. 34a The title compound was prepared according to the method described in Example 34, using 4-(4-cyanophenyl)-3-buten-2-one (prepared as described in preparation 8) as the starting material. mp: 199-201° C.

$^1$HNMR δppm (DMSO-$d_6$): 1.20(t, 3H, J=7.2 Hz, COOCH$_2$CH$_3$), 2.80-3.60(m, 10H, 5NCH$_2$), 4.04-4.11(m, 4H, COCH$_2$+COOCH$_2$CH$_3$), 7.08(d, 1H, J=16.5 Hz, =CHCO), 7.73(d, 1H, J=16.5 Hz, CH=), 7.96(s, 4H, ArH). MS (m/z): 341.4(M$^+$, 20), 296.3(M$^+$−45, 4), 184.2(M$^+$−157, 14), 171(60), 156.1(100).

Example 34b

5-[($N_4$-Ethoxycarbonyl)piperazyl]-1-(4-methoxy-3-hydroxyphenyl)-1-penten-3-one hydrochloride Compound No. 34b The title compound was prepared according to the method described in Example 34, using 4-(4-methoxy-3-hydroxyphenyl)-3-buten-2-one (prepared as described in preparation 20) as the starting material. Mp: 197-199° C.

Example 34c

5-[($N_4$-Ethoxycarbonyl)piperazyl]-1-(3-methoxy-4-ethoxyphenyl)-1-penten-4-methyl-3-one hydrochloride Compound No. 34c The title compound was prepared according to the method described in Example 34, using 4-(3-methoxy-4-ethoxyphenyl)-3-penten-2-one (prepared as described in preparation 28) as the starting material. Mp: 128-130° C.

$^1$HNMR δppm (DMSO-$d_6$): 1.08(d, 3H, J=6.9 Hz, —CHCH$_3$), 1.18(t, 3H, J=7.2 Hz, COOCH$_2$CH$_3$), 1.33(t, 3H, J=7.2 Hz, OCH$_2$CH$_3$), 2.49(q, 1H, J=6.9 Hz, =CHCH$_3$), 3.20-3.60 (m, 10H, 5NCH$_2$), 3.82(s, 3H, OCH$_3$), 4.08(m, 6H, COOCH$_2$CH$_3$+OCH$_2$CH$_3$+COCH$_2$), 6.97(d, 1H, J=7.2 Hz, ArH), 6.99(d, 1H, J=15.9 Hz, =CHCO), 6.97(d, 1H, J=8.4 Hz, ArH), 7.37(s, 1H, ArH), 7.65(d, 1H, J=15.9 Hz, CH=). MS (m/z): 404.3(M$^+$, 9), 246.2(M$^+$−157, 12), 171.2(100).

Example 34d

5-[($N_4$-Ethoxycarbonyl)piperazyl]-1-(4-methoxyphenyl)-1-penten-3-one hydrochloride Compound No. 34d The title compound was prepared according to the method described in Example 34, using 4-(4-methoxyphenyl)-3-buten-2-one (prepared as described in preparation 13) as the starting material. Mp: 175-177° C.

$^1$HNMR δppm (DMSO-$d_6$): 1.193(t, 3H, J=7.2 Hz, COOCH$_2$CH$_3$), 3.27-3.49(m, 10H, 5NCH$_2$), 3.79(s, 3H, OCH$_3$), 4.08(q, 4H, COOCH$_2$CH$_3$, COCH$_2$), 6.78(d, 1H, J=15.9 Hz, =CHCO), 7.02(d, 2H, J=8.7 Hz, ArH AA'), 7.66 (d, 1H, J=15.9 Hz, CH=), 7.71(d, 2H, J=8.7 Hz, ArH BB').

MS (m/z): 346.4(M$^+$, 34), 188.2(M$^+$−158, 100), 171.2(45).

Example 34e

5-[($N_4$-Ethoxycarbonyl)piperazyl]-1-(4-fluorophenyl)-1-penten-3-one hydrochloride Compound No. 34e The title compound was prepared according to the method described in Example 34, using 4-(4-fluorophenyl)-3-buten-2-one (prepared as described in preparation 18) as the starting material. Mp: 178-180° C.

Example 35

5-(2,6-Dimethylmorpholinyl)-1-(4-chlorophenyl)-1-penten-3-one hydrochloride Compound No. 35

0.303 g (2.0 mmol) of 2,6-dimethylmorpholine hydrochloride and 0.4 g (13 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 2 hr. After the solid was dissolved, 0.36 g (2.0 mmol) of 4-(4-chlorophenyl)-3-buten-2-one (prepared as described in preparation 1) was added to the above reaction mixture. The solution was further refluxed and stirred for 13 hr. TLC showed the reaction was completed. After cooling with ice-water bath, the precipitated pale yellow solid was collected by filtration and then recrystallized from anhydrous ethanol and dried to give 0.37 g of white crystals, yield: 53.8%, mp: 218-220° C.

$^1$HNMR δppm (DMSO-$d_6$): 1.09(d, 6H, J=6.6 Hz, 2×CH$CH_3$), 2.47-2.68(m, 6H, 3N$CH_2$), 3.24-3.46(t, 2H, CO$CH_2$), 3.95(q, 2H, J=6.6 Hz, 2×$CH$CH_3$), 6.92(d, 1H, J=16.2 Hz, =CHCO), 7.49(d, 2H, J=8.4 Hz, ArHAA'), 7.69(d, 1H, J=16.2 Hz, CH=), 7.79(d, 2H, J=8.4 Hz, ArHBB'). MS (m/z): 307 (M$^+$, 20), 192(M$^+$–114–H, 24), 165(M$^+$–142, 60).

Example 35a

5-(2,6-Dimethylmorpholinyl)-1-(4-bromophenyl)-1-penten-3-one hydrochloride Compound No. 35a The title compound was prepared according to the method described in Example 35, using 4-(4-bromophenyl)-3-buten-2-one (prepared as described in preparation 12) as the starting material. Mp: 205-207° C.

Example 35b

5-(2,6-Dimethylmorpholinyl)-1-(4-fluorophenyl)-1-penten-3-one hydrochloride Compound No. 35b The title compound was prepared according to the method described in Example 35, using 4-(4-fluorophenyl)-3-buten-2-one (prepared as described in preparation 18) as the starting material. Mp: 211-213° C.

Example 36

5-(2,6-Dimethylmorpholinyl)-1-(3-hydroxy-4-methoxyphenyl)-1-penten-3-one hydrochloride Compound No. 36

0.303 g (2.0 mmol) of 2,6-dimethylmorpholine hydrochloride and 0.4 g (13 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 2.0 hr. After the solid was dissolved, 0.384 g (2.0 mmol) of 4-(3-hydroxy-4-methoxyphenyl)-3-buten-2-one (prepared as described in preparation 20) was added to the above reaction mixture. The solution was further refluxed and stirred for 15 hr. TLC showed the reaction was completed. After cooling with cold water bath, the precipitated pale yellow solid was collected by filtration and then recrystallized from anhydrous ethanol and dried to give 0.26 g of white crystals, yield: 36.6%, mp: 194-196° C.

$^1$HNMR δppm (DMSO-$d_6$): 1.09(d, 6H, J=6.6 Hz, 2×CH$CH_3$), 2.47-2.68(m, 6H, 3N$CH_2$), 3.24-3.46(t, 2H, CO$CH_2$), 3.95(q, 2H, J=6.6 Hz, 2×$CH$CH_3$), 6.61(d, 1H, J=16.2 Hz, =CHCO), 6.98(d, 1H, J=8.4 Hz, ArH), 7.14(d, 2H, J=8.4 Hz, ArH), 7.57(d, 1H, J=16.2 Hz, CH=).

MS (m/z): 319(M$^+$, 40), 204(M$^+$–115, 35), 190(M$^+$–115-14, 10).

Example 37

5-(2,6-Dimethylmorpholinyl)-1-(3-ethoxy-4-hydroxyphenyl)-1-penten-3-one hydrochloride Compound No. 37

0.5 g (3.3 mmol) of 2,6-dimethylmorpholine hydrochloride and 0.9 g (30 mmol) of paraformaldehyde were dissolved in anhydrous ethanol (15 ml). The pH value of the solution was adjusted to pH=1.5-2.0 with concentrated hydrochloric acid and the reaction mixture was refluxed and stirred for 1 hr. After the solid was dissolved, 0.619 g (3.0 mmol) of 4-(3-ethoxy-4-hydroxyphenyl)-3-buten-2-one (prepared as described in preparation 5) was added to the above reaction mixture. The solution was further refluxed and stirred for 9 hr. After cooling with cold water bath, the precipitated pale yellow solid was collected by filtration and then recrystallized from anhydrous ethanol-methanol and dried to give 0.281 g of white crystals, yield 25.3%, mp: 198-201° C.

$^1$HNMR δppm (DMSO-$d_6$): 1.10(d, 6H, J=6.6 Hz, 2×CH$CH_3$), 1.29-1.33(t, 3H, J=7.2 Hz, O$CH_2CH_3$), 2.47-2.61(m, 6H, 2N$CH_2$), 2.62-2.69(t, 2H, CO$CH_2$), 3.25-3.46(q, 2H, J=7.2 Hz, O$CH_2$CH$_3$), 3.87(q, 1H, OH, $D_2$O exchange), 3.95 (q, 2H, J=6.6 Hz, 2×$CH$CH$_3$), 6.73(d, 1H, J=16.2 Hz, =CHCO), 6.84(d, 1H, J=8.1 Hz, ArH), 7.15(q, 1H, J=8.1 Hz, J=1.5 Hz, ArH), 7.29(s, 1H, ArH), 7.59(d, 1H, J=16.2 Hz, CH=).

FAB-MS (m/z): 334.3(M$^+$+1).

Example 38

5-(2,6-Dimethylmorpholinyl)-1-(3,4-methylenedioxyphenyl)-1-penten-3-one hydrochloride Compound No. 38

0.30 g (2.0 mmol) of 2,6-dimethylmorpholine hydrochloride and 0.15 g (5 mmol) of paraformaldehyde were dissolved in anhydrous ethanol (10 ml). The pH value of the solution was adjusted to pH=1.5-2.0 with concentrated hydrochloric acid and the reaction mixture was refluxed and stirred for 2 hr. After the solid was dissolved, 0.38 g (2.0 mmol) of 4-(3,4-methylenedioxyphenyl)-3-buten-2-one (prepared as described in preparation 15) was added to the above reaction mixture. The solution was further refluxed and stirred for 11 hr. After cooling with cold water bath, the precipitated pale yellow solid was collected by filtration and then recrystallized from anhydrous ethanol-methanol and dried to give 0.46 g of white crystals, yield: 65.2%, mp: 178-181° C.

$^1$HNMR δppm (DMSO-$d_6$): 1.11(d, 6H, J=6.6 Hz, 2×CH$CH_3$), 2.47-2.68(m, 6H, 3N$CH_2$), 3.26-3.46(t, 2H, CO$CH_2$), 3.89(q, 2H, J=6.6 Hz, 2×$CH$CH$_3$), 6.08(s, 2H, O$CH_2$O), 6.77 (d, 1H, J=16.2 Hz, =CHCO), 6.98(d, 1H, J=8.4 Hz, ArH), 7.20(dd, 1H, J=8.4 Hz, J=1.5 Hz, ArH), 7.39(d, 1H, J=1.5 Hz, ArH), 7.61(d, 1H, J=16.2 Hz, CH=). MS (m/z): 317(M$^+$, 45), 302(M$^+$–15, 3), 272(M$^+$–45, 5), 202(M$^+$–115, 90).

Anal. Cald. for $C_{22}H_{31}N_2O_5Cl$: C, 61.10%; H, 6.78%; N, 3.96%. Found: C, 61.23%; H, 6.59%; N, 3.98%.

Example 39

5-(2,6-Dimethylmorpholinyl)-1-(3-methoxy-4-ethoxyphenyl)-1-penten-3-one hydrochloride Compound No. 39

0.303 g (2.0 mmol) of 2,6-dimethylmorpholine hydrochloride and 0.6 g (20 mmol) of paraformaldehyde were dissolved in anhydrous ethanol (5 ml ). The pH value of the solution was adjusted to pH=1.5-2.0 with concentrated hydrochloric acid and the reaction mixture was refluxed and stirred for 1 hr. After the solid was dissolved, 0.44 g (2.0 mmol) of 4-(3-methoxy-4-ethoxyphenyl)-3-buten-2-one (prepared as described in preparation 6) was added to the above reaction mixture. The solution was further refluxed and stirred for 11 hr. TLC showed the reaction was completed. After cooling with cold water bath, the precipitated pale yellow solid was collected by filtration and then recrystallized from anhydrous ethanol-methanol and dried to give 0.15 g of white crystals, yield: 19.5%, mp: 191-194° C.

$^1$HNMR δppm (DMSO-$d_6$): 1.06-1.12(d, 6H, J=6.6 Hz, 2×CH$CH_3$), 1.29-1.34(t, 3H, J=7.2 Hz, OCH$_2$$CH_3$), 2.02-3.20(m, 6H, 3NCH$_2$), 3.24-3.46(q, 2H, J=7.2 Hz, O$CH_2$CH$_3$), 3.79(s, 3H, OCH$_3$), 4.05(q, 2H, J=6.6 Hz, 2×$CH$CH$_3$), 6.61(d, 1H, J=16.2 Hz, =CHCO), 6.98(d, 1H, J=8.4 Hz, ArH), 7.25(d, 1H, J=8.4 Hz, ArH), 7.32(d, 1H, J=8.4 Hz, ArH), 7.64(d, 1H, J=16.2 Hz, CH=). MS (m/z): 347(M$^+$, 42), 232(M$^+$−115, 94), 190((M$^+$−115-14, 10).

Example 39a 5-(2,6-Dimethylmorpholinyl)-1-(4-methoxy-3-ethoxyphenyl)-1-penten-3-one hydrochloride Compound No. 39a The title compound was prepared according to the method described in Example 39, using 4-(4-methoxy-3-ethoxyphenyl)-3-buten-2-one (prepared as described in preparation 4) as the starting material. Mp: 176-178° C.

Example 39b 5-(2,6-Dimethylmorpholinyl)-1-(4-bromophenyl)-1-penten-3-one hydrochloride Compound No. 39b The title compound was prepared according to the method described in Example 39, using 4-(4-bromophenyl)-3-buten-2-one (prepared as described in preparation 12) as the starting material. mp: 172-174° C.

Example 39c 5-(2,6-Dimethylmorpholinyl)-1-(4-methoxyphenyl)-1-penten-3-one hydrochloride Compound No. 39c The title compound was prepared according to the method described in Example 39, using 4-(4-methoxyphenyl)-3-buten-2-one (prepared as described in preparation 13) as the starting material. mp: 209-211° C.

Example 39d 5-(2,6-Dimethylmorpholinyl)-1-(3-methoxy-4-ethoxyphenyl)-1-penten-4-methyl-3-one hydrochloride Compound No. 39d The title compound was prepared according to the method described in Example 39, using 4-(3-methoxy-4-ethoxyphenyl)-3-penten-2-one (prepared as described in preparation 28) as the starting material. Mp: 120-123° C.

$^1$HNMR δppm (DMSO-$d_6$): 1.08(d, 6H, J=6.9 Hz, 2×CH$CH_3$), 1.204(d, 3H, J=6.6 Hz, COCH$CH_3$), 1.29-1.34(t, 3H, J=7.2 Hz, OCH$_2$$CH_3$), 2.49(q, 1H, J=6.6 Hz, COCH$CH_3$), 2.47-2.68(m, 6H, 3NCH$_2$), 3.24-3.46(q, 2H, J=6.9 Hz, 2× CH$CH_3$), 4.08(q, 2H, J=7.2 Hz, O$CH_2$CH$_3$), 6.98(d, 1H, J=15.9 Hz, =CHCO), 7.00(d, 1H, J=8.4 Hz, ArH), 7.27(d, 1H, J=8.4 Hz, ArH), 7.37(d, 1H, J=8.4 Hz, ArH), 7.66(d, 1H, J=15.9 Hz, CH=).
MS (m/z): 361.3(M$^+$, 23), 346.3(M$^+$−15, 5), 128.2((100).

Example 39e 5-(2,6-Dimethylmorpholinyl)-1-(4-fluorophenyl)-1-penten-3-one hydrochloride Compound No. 39e The title compound was prepared according to the method described in Example 39, using 4-(4-fluorophenyl)-3-buten-2-one (prepared as described in preparation 18) as the starting material. Mp: 211-213° C.

Example 40

5-(2,6-Dimethylmorpholinyl)-1-(4-trifluoromethylphenyl)-1-penten-3-one hydrochloride Compound No. 40

0.165 g (1.1 mmol) of 2,6-dimethylmorpholine hydrochloride and 0.3 g (10 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 1 hr. After the solid was dissolved, 0.214 g (1.0 mmol) of 4-(4-trifluoromethylphenyl)-3-buten-2-one (prepared as described in preparation 16) was added to the above reaction mixture. The solution was further refluxed and stirred for 12 hr. After cooling with ice-water bath, the precipitated pale yellow solid was collected by filtration and then recrystallized from anhydrous ethanol and dried to give 0.125 g of white crystals, yield: 33.16%, mp: 203-205° C.

$^1$HNMR δppm (DMSO-$d_6$): 1.09(d, 6H, J=6.6 Hz, 2 $CH_3$—CH), 2.47-2.68(m, 6H, 3NCH$_2$), 3.33-3.43(m, 2H, $COCH_2$), 3.85(q, 2H, J=6.6 Hz, 2CH$_3$—CH), 7.04(d, 1H, J=16.2 Hz, =CHCO), 7.759(d, 1H, J=16.2 Hz, CH=), 7.819 (d, 2H, J=8.4 Hz, ArH$_{AA'}$), 7.955(d, 2H, J=8.4 Hz, ArH$_{BB'}$).
FAB-MS (m/z): 342.2(M$^+$+1), 274.2(M$^+$−F$_3$C+1), 128.4 (M$^+$−213).

Example 41

5-[(N$_4$-Benzyl)piperazyl]-1-(4-bromophenyl)-1-penten-3-one hydrochloride Compound No. 41

0.274 g (1.1 mmol) of N4-benzylpiperizine hydrochloride and 0.3 g (10 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 1 hr. After the solid was dissolved, 0.225 g (1.0 mmol) of 4-(4-bromophenyl)-3-buten-2-one (prepared as described in preparation 12) was added to the above reaction mixture. The solution was further refluxed and stirred for 8 hr. After cooling with cold water bath, the precipitated pale yellow solid was collected by filtration and then recrystallized from anhydrous ethanol and dried to give 0.132 g of white crystals, yield: 27.16%, mp: 202-203° C.

$^1$HNMR δppm (DMSO-d$_6$): 3.18-3.61(m, 10H, 5NCH$_2$), 3.55(s, 2H, NCH$_2$Ph), 4.25(brs, 2H, COCH$_2$), 7.09(d, 1H, J=16.2 Hz, =CHCO), 7.38(d, 2H, J=9.4 Hz, ArH$_{AA'}$), 7.45(d, 1H, J=16.2 Hz, CH=), 7.52(d, 2H, J=9.4 Hz, ArH$_{BB'}$), 7.62(s, 5H, ArH). MS (m/z): 414(M$^+$, 5), 323(M$^+$−91, 4), 238(M$^+$−176, 9).

Example 42

5-[(N$_4$-Benzyl)piperazyl]-1-(4-propoxyphenyl)-1-penten-3-one hydrochloride Compound No. 42

0.548 g (2.2 mmol) of N$_4$-benzylpiperizine hydrochloride and 0.6 g (20 mmol) of paraformaldehyde were dissolved in anhydrous ethanol (10 ml). The pH value of the solution was adjusted to pH=1.5-2.0 with concentrated hydrochloric acid and the reaction mixture was refluxed and stirred for 1 hr. After the solid was dissolved, 0.409 g (2.0 mmol) of 4-(4-propoxyphenyl)-3-buten-2-one (prepared as described in preparation 19) was added to the above reaction mixture. The solution was further refluxed and stirred for 18 hr. After cooling with cold water bath, the precipitated pale yellow solid was collected by filtration and then recrystallized from anhydrous ethanol and dried to give 0.305 g of white crystals, yield: 32.8%, mp: 216-218° C.
$^1$HNMR δppm (DMSO-d$_6$): 0.97(t, 3H, J=7.2 Hz, CH$_3$CH$_2$—), 1.4-1.81(m, 4H, (CH$_2$)$_2$), 2.87(m, 4H, 2NCH$_2$), 3.2-3.4(m, 6H, CO(CH$_2$)$_2$N, —NCH$_2$-Ph), 4.03((t, 2H, J=7.2 Hz, —CH2O), 6.73(d, 1H, J=16.2 Hz, =CHCO), 7.02(d, 2H, J=8.5 Hz, ArH$_{AA'}$), 7.21(m, 5H, ArH), 7.63(d, 2H, J=8.5 Hz, ArH$_{BB'}$), 7.68(d, 1H, J=16.2 Hz, CH=).
MS (m/z): 392(M$^+$, 2), 216(M$^+$−176, 3), 176(M$^+$−216, 30).

Example 43

5-[(N$_4$-Benzyl)piperazyl]-1-(3-methoxy-4-ethoxyphenyl)-1-penten-3-one hydrochloride Compound No. 43

0.822 g (3.3 mmol) of N$_4$-benzylpiperizine hydrochloride and 0.9 g (30 mmol) of paraformaldehyde were dissolved in anhydrous ethanol (15 ml). The pH value of the solution was adjusted to pH=2.0-3.0 with concentrated hydrochloric acid and the reaction mixture was refluxed and stirred for 1 hr. After the solid was dissolved, 0.466 g (2.2 mmol) of 4-(3-methoxy-4-ethoxyphenyl)-3-buten-2-one (prepared as described in preparation 6) was added to the above reaction mixture. The solution was further refluxed and stirred for 11 hr, after cooling with water bath, the precipitated pale yellow solid was collected by filtration and then recrystallized from ethanol-water and dried to give 0.69 g of white crystals, yield: 67.7%, mp: 246-248° C.
$^1$HNMR δppm (DMSO-d$_6$): 1.33(t, 3H, J=7.2 Hz, OCH$_2$CH$_3$), 3.26-3.66(brm, 12H, 5NCH$_2$+COCH$_2$), 3.81(s, 3H, OCH$_3$), 4.05(q, 2H, J=7.2 Hz, OCH$_2$CH$_3$), 4.31(s, 2H, —NCH$_2$Ph), 6.84(d, J=16.2 Hz, 1H, =CHCO), 6.99(d, 1H, J=7.2 Hz, ArH), 7.23(dd, 2H, J=7.2 Hz, J=1.8 Hz, ArH), 7.32(m, 5H, Ar(b)5H), 7.61(d, 1H, J=16.2 Hz, CH=). MS (m/z): 408(M$^+$, 9), 317(M$^+$−91, 2), 232(M$^+$−176, 38).

Example 44

5-[(N$_4$-Benzyl)piperazyl]-1-(4-chlorophenyl)-1-penten-3-one hydrochloride Compound No. 44

0.822 g (3.3 mmol) of N$_4$-benzylpiperizine hydrochloride and 0.9 g (30 mmol) of paraformaldehyde were dissolved in anhydrous ethanol (15 ml). The pH value of the solution was adjusted to pH=2.0-3.0 with concentrated hydrochloric acid and the reaction mixture was refluxed and stirred for 1 hr. After the solid was dissolved, 0.542 g (3 mmol) of 4-(4-chlorophenyl)-3-buten-2-one (prepared as described in preparation 1) was added to the above reaction mixture. The solution was further refluxed and stirred for 6 hr, after cooling with cold water bath, the precipitated pale yellow solid was collected by filtration and then recrystallized from ethanol-water and dried to give 0.56 g of white crystals, yield: 41.9%, mp: 242-244° C.
$^1$HNMR δppm (DMSO-d$_6$): 3.26-3.4(brm, 12H, 5NCH$_2$+COCH$_2$), 4.21(s, 2H, NCH$_2$Ph), 6.95(d, 1H, J=16.2 Hz, =CHCO), 7.43(brs, 5H, Ar(b)H), 7.51(d, 2H, J=8.1 Hz, ArH$_{AA'}$), 7.66(d, 1H, J=16.2 Hz, CH=), 7.77(d, 2H, J=8.1 Hz, ArH$_{BB'}$).
FAB-MS (m/z): 369.6(M$^+$+1).

Example 44a

5-[(N$_4$-Benzyl)piperazyl]-1-(4-fluorophenyl)-1-penten-3-one hydrochloride Compound No. 44a The title compound was prepared according to the method described in Example 44, using 4-(4-fluorophenyl)-3-buten-2-one (prepared as described in preparation 18) as the starting material. Mp: 204-207° C.

Example 44b

5-[(N$_4$-Benzyl)piperazyl]-1-(4-trifluoromethylphenyl)-1-penten-3-one hydrochloride Compound No. 44b The title compound was prepared according to the method described in Example 44, using 4-(4-trifluoromethylphenyl)-3-buten-2-one (prepared as described in preparation 16) as the starting material. Mp: 185-187° C.

Example 45

0.498 g (2.0 mmol) of N$_4$-benzylpiperizine hydrochloride and 0.6 g (20 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 0.5 hr. After the solid was dissolved, 0.36 g (2.0 mmol) of 4-(3-chlorophenyl)-3-buten-2-one (prepared as described in preparation 24) was added to the above reaction mixture. The solution was further refluxed and stirred for 7 hr. TLC showed the reaction was completed. After cooling with cold water bath, the precipitated pale yellow solid was collected by filtration and then recrystallized from ethanol-methanol and dried to give 0.66 g of white crystals, yield: 89.7%, mp: 201-203° C.
$^1$HNMR δppm (DMSO-d$_6$): 3.29-3.36(m, 10H, 5NCH$_2$), 3.39(s, 2H, NCH$_2$Ph), 3.66(brs, 2H, COCH$_2$), 7.02(d, 1H, J=16.5 Hz, C=CHCO), 7.47(s, 5H, ArH), 7.58(d, 2H, J=7.2 Hz, Ar(a)H), 7.65(d, 1H, J=16.5 Hz, CH=), 7.71(d, 2H, J=7.2 Hz, Ar(a)H), 7.85(s, 1H, ArH). MS (m/z): 368(M$^+$, 7), 277(M$^+$−91, 3), 192(M$^+$−176, 26), 176(M$^+$−192, 30).

Example 46

5-[(N$_4$-Benzyl)piperazyl]-1-(4-cyanophenyl)-1-penten-3-one hydrochloride Compound No. 46

0.274 g (1.1 mmol) of N$_4$-benzylpiperizine hydrochloride and 0.3 g (10 mmol) of paraformaldehyde were dissolved in anhydrous ethanol (5 ml). The pH value of the solution was adjusted to pH=1.5-2.0 with concentrated hydrochloric acid and the reaction mixture was refluxed and stirred for 0.5 hr. After the solid was dissolved, 0.171 g (1.0 mmol) of 4-(4-cyanophenyl)-3-buten-2-one (prepared as described in preparation 8) was added to the above reaction mixture. The solution was further refluxed and stirred for 2 hr. After cooling with cold water bath, the precipitated pale yellow solid was collected by filtration and then recrystallized from anhydrous ethanol-methanol and dried to give 0.235 g of white crystals, yield: 59.4%, mp: 219-221° C.

$^1$HNMR δppm (DMSO-$d_6$): 3.21-3.61(m, 10H, 5NCH$_2$), 3.55(s, 2H, NCH$_2$Ph), 4.39(brs, 2H, COCH$_2$), 7.08(d, 1H, J=16.2 Hz, =CHCO), 7.46(d, 2H, J=9.4 Hz, ArH$_{AA'}$), 7.61(d, 2H, J=9.4 Hz, ArH$_{BB'}$), 7.91(s, 5H, ArH), 8.13(d, 1H, J=16.2 Hz, CH=). MS (m/z): 359(M$^+$, 4), 268(M$^+$−91, 2), 183(M$^+$−176, 9).

Example 47

5-[(N$_4$-Benzyl)piperazyl]-1-(3-hydroxy-4-methoxyphenyl)-1-penten-3-one hydrochloride Compound No. 47

0.822 g (3.3 mmol) of N$_4$-benzylpiperizine hydrochloride and 0.9 g (30 mmol) of paraformaldehyde were dissolved in anhydrous ethanol (15 ml). The pH value of the solution was adjusted to pH=2.0-3.0 with concentrated hydrochloric acid and the reaction mixture was refluxed and stirred for 0.5 hr. After the solid was dissolved, 0.577 g (3.0 mmol) of 4-(3-hydroxy-4-methoxyphenyl)-3-buten-2-one (prepared as described in preparation 20) was added to the above reaction mixture. The solution was further refluxed and stirred for 7 hr. After cooling with cold water bath, the precipitated pale yellow solid was collected by filtration and then recrystallized from anhydrous ethanol-water and dried to give 0.74 g of white crystals, yield: 54.4%, mp: 228-230° C.

$^1$HNMR δppm (DMSO-$d_6$): 3.35-3.62(brm, 12H, 5NCH$_2$+COCH$_2$), 3.78(s, 3H, OCH$_3$), 4.30(s, 2H, —NCH$_2$Ph), 6.56(d, 1H, J=16.2 Hz, =CHCO), 6.91(d, 1H, J=7.2 Hz, ArH), 7.23(dd, 2H, J=7.2 Hz, J=1.8 Hz, ArH), 7.30-7.45(m, 6H, Ar(b)5H, Ar(a)1H), 7.41(d, 1H, J=16.2 Hz, CH=). MS (m/z): 394(M$^+$, 4.5), 218(M$^+$−176, 45), 204(M$^+$−176-14, 20).

Example 48

5-[(N$_4$-Benzyl)piperazyl]-1-(3,4-dimethoxyphenyl)-1-penten-3-one hydrochloride Compound No. 48

0.822 g (3.3 mmol) of N$_4$-benzylpiperizine hydrochloride and 0.9 g (30 mmol) of paraformaldehyde were dissolved in anhydrous ethanol (15 ml). The pH value of the solution was adjusted to pH=2.0-3.0 with concentrated hydrochloric acid and the reaction mixture was refluxed and stirred for 0.5 hr. After the solid was dissolved, 0.619 g (3.0 mmol) of 4-(3,4-dimethoxyphenyl)-3-buten-2-one (prepared as described in preparation 9) was added to the above reaction mixture. The solution was further refluxed and stirred for 6 hr. After cooling with water bath, the precipitated pale yellow solid was collected by filtration and then recrystallized from ethanol-water and dried to give 0.36 g of white crystals, yield: 25.4%, mp: 195-197° C.

$^1$HNMR δppm (DMSO-$d_6$): 3.35-3.62(brm, 12H, 5NCH$_2$+COCH$_2$), 3.79(s, 6H, 2×OCH$_3$), 4.30(s, 2H, —NCH$_2$Ph), 6.75(d, 1H, J=16.2 Hz, =CHCO), 6.91(d, 1H, J=7.2 Hz, ArH), 7.23(dd, 2H, J=7.2 Hz, J=1.8 Hz, ArH), 7.30-7.45(m, 5H, Ar(b)5H), 7.55(d, 1H, J=16.2 Hz, CH=). MS (m/z): 380(M$^+$, 2), 362(M$^+$−18, 1), 204(M$^+$−176, 35).

Example 49

5-[(N$_4$-Benzyl)piperazyl]-1-(4-methoxyphenyl)-1-penten-3-one hydrochloride Compound No. 49

0.548 g (2.2 mmol) of N4-benzylpiperizine hydrochloride and 0.6 g (20 mmol) of paraformaldehyde were dissolved in anhydrous ethanol (15 ml). The pH value of the solution was adjusted to pH=1.5-2.0 with concentrated hydrochloric acid and the reaction mixture was refluxed and stirred for 0.5 hr. After the solid was dissolved, 0.352 g (2.0 mmol) of 4-(4-methoxyphenyl)-3-buten-2-one (prepared as described in preparation 13) was added to the above reaction mixture. The solution was further refluxed and stirred for 16 hr. After cooling with water bath, the precipitated pale yellow solid was collected by filtration and then recrystallized from anhydrous ethanol and dried to give 0.142 g of white crystals, yield: 16.2%, mp: 219-222° C.

$^1$HNMR δppm (DMSO-$d_6$): 3.35-3.65(brm, 12H, 5NCH$_2$+COCH$_2$), 3.77(s, 3H, OCH$_3$), 4.32(s, 2H, —NCH$_2$Ph), 6.71(d, 1H, J=16.2 Hz, =CHCO), 6.95(d, 2H, J=7.2 Hz, ArH), 7.49(d, 1H, J=16.2 Hz, CH=), 7.59(m, 5H, Ar(b)H), 7.65(d, 2H, J=7.2 Hz, ArH). MS (m/z): 364(M$^+$, 6.5), 273(M$^+$−91, 2), 189(M$^+$−175, 30).

Example 50

5-[(N$_4$-Benzyl)piperazyl]-1-(3,4,5-trimethoxyphenyl)-1-penten-3-one hydrochloride Compound No. 50

0.548 g (2.2 mmol) of N$_4$-benzylpiperizine hydrochloride and 0.6 g (20 mmol) of paraformaldehyde were dissolved in anhydrous ethanol (15 ml). The pH value of the solution was adjusted to pH=1.5-2.0 with concentrated hydrochloric acid and the reaction mixture was refluxed and stirred for 0.5 hr. After the solid was dissolved, 0.352 g (2.0 mmol) of 4-(3,4,5-trimethoxyphenyl)-3-buten-2-one (prepared as described in preparation 7) was added to the above reaction mixture. The solution was further refluxed and stirred for 16 hr. After cooling with water bath, the precipitated pale yellow solid was collected by filtration and then recrystallized from anhydrous ethanol and dried to give 0.22 g of white crystals, yield: 22.2%, mp: 214-218° C.

$^1$HNMR δppm (DMSO-$d_6$): 3.31-3.61(m, 12H, 5NCH$_2$+CH$_2$Ph), 3.91(brs, 9H, 3×OCH$_3$), 4.21(br, 2H, COCH$_2$), 6.85 (d, 1H, J=16.2 Hz, =CHCO), 6.89(s, 1H, Ar(a)H), 7.29(s, 5H, 5Ar(b)H), 7.48(s, 1H, Ar(a)H), 7.61(d, 1H, J=16.2 Hz, CH=C); MS (m/z): 378(M$^+$, 7), 202(M$^+$−176, 50), 175(25).

Example 51

5-[(N$_4$-Benzyl)piperazyl]-1-(3,4-methylenedioxyphenyl)-1-penten-3-one hydrochloride Compound No. 51

2.48 g (10 mmol) of N$_4$-benzylpiperizine hydrochloride and 0.9 g (30 mmol) of paraformaldehyde were dissolved in anhydrous ethanol (50 ml). The pH value of the solution was adjusted to pH=1.5-2.0 with concentrated hydrochloric acid and the reaction mixture was refluxed and stirred for 1 hr. After the solid was dissolved, 1.9 g (10.0 mmol) of 4-(3,4-methylenedioxyphenyl)-3-buten-2-one (prepared as described in preparation 15) was added to the above reaction mixture. The solution was further refluxed and stirred for 15 hr. After cooling with cold water bath, the precipitated pale yellow solid was collected by filtration and then recrystallized from anhydrous ethanol and dried to give 2.5 g of white crystals, yield: 54.1%, mp: 180-184° C.

$^1$HNMR δppm (DMSO-d$_6$): 3.00-3.60(m, 10H, 4NCH$_2$+ CH$_2$N), 3.92(s, 2H, CH$_2$Ph), 6.05(s, 2H, OCH$_2$O), 6.75(d, 1H, J=16.2 Hz, C=CHCO), 6.94(d, 1H, J=7.2 Hz, Ar(a)H), 7.20(dd, 1H, J=7.2 Hz, J=1.8 Hz, Ar(a)H), 7.28-7.42(m, 6H, 5Ar(b)H+Ar(a)H), 7.61(d, 1H, J=16.2 Hz, CH=C). MS (m/z): 378(M$^+$, 7), 202(M$^+$-176, 50), 175(25).

Example 52

5-[(N$_4$-Methyl)piperazyl]-1-(3,4-methylenedioxyphenyl)-1-penten-3-one hydrochloride Compound No. 52

0.2 g (1.5 mmol) of N$_4$-benzylpiperizine hydrochloride and 0.45 g (15 mmol) of paraformaldehyde were dissolved in anhydrous ethanol (30 ml). The pH value of the solution was adjusted to pH=8 with triethylamine and the reaction mixture was refluxed and stirred for 1 hr. After the solid was dissolved, 0.29 g (1.5 mol) of 4-(3,4-methylenedioxy-phenyl)-3-buten-2-one (prepared as described in preparation 15) was added to the above reaction mixture. The solution was further refluxed and stirred for 24 hr. TLC showed the reaction was completed. After cooling with water bath, the reaction mixture was filtered to remove triethylamine hydrochloride, filtrate was evaporated to give the precipitated yellow solid, filtered, dried and then recrystallized from acetone-anhydrous ethanol and dried to give 0.16 g of pale yellow crystals, yield: 31.5%, mp: 171-174° C.

$^1$HNMR δppm (DMSO-d$_6$): 2.30(s, 3H, NCH$_3$), 2.80-3.40 (m, 10H, 5NCH$_2$), 3.55(m, 2H, COCH$_2$), 6.04(s, 2H, OCH$_2$O), 6.62(d, 1H, J=16.2 Hz, =CHCO), 6.90(d, 1H, J=7.2 Hz, ArH), 7.16(dd, 1H, J=7.2 Hz, J=1.8 Hz, ArH), 7.29(d, 1H, J=1.8 Hz, ArH), 7.49(d, 1H, J=16.2 Hz, CH=); MS (m/z): 302(M$^+$, 18), 272(2), 259(7), 46(12).

Example 52a

5-[(N$_4$-Methyl)piperazyl]-1-(4-methoxyphenyl)-1-penten-3-one hydrochloride Compound No. 52a The title compound was prepared according to the method described in Example 52, using 4-(4-methoxyphenyl)-3-buten-2-one (prepared as described in preparation 13) as the starting material. mp: 165-167° C.

$^1$HNMR δppm (DMSO-d$_6$): 2.30(s, 3H, NCH$_3$), 2.80-3.40 (m, 10H, 5NCH$_2$), 3.55(m, 2H, COCH$_2$), 3.80(s, 3H, 2×OCH$_3$), 7.04(d, 1H, J=16.5 Hz, =CHCO), 7.74(d, 1H, J=9 Hz, ArH), 7.81(d, 1H, J=16.5 Hz, CH=); 7.84(s, 1H, ArH), 7.99(d, 1H, J=9.0 Hz, ArH). MS (m/z): 328(M$^+$, 18), 229.2 (M$^+$-99, 14).

Example 52b

5-[(N$_4$-Methyl)piperazyl]-1-(4-hydroxy-3-ethoxyphenyl)-1-penten-3-one hydrochloride Compound No. 52b The title compound was prepared according to the method described in Example 52, using 4-(4-hydroxy-3-ethoxyphenyl)-3-buten-2-one (prepared as described in preparation 5) as the starting material. mp: 168-171° C.

$^1$HNMR δppm (DMSO-d$_6$): 1.30(t, 3H, J=7.2 Hz, OCH$_2$CH$_3$), 2.30(s, 2H, COCH$_2$), 2.49(s, 3H, NCH$_3$), 2.80-3.40(m, 10H, 5NCH$_2$), 4.09(q, 2H, J=7.2 Hz, OCH$_2$CH$_3$), 6.74(d, 1H, J=15.9 Hz, =CHCO), 6.84(d, J=8.4 Hz, 1H, ArH), 7.13(d, 1H, J=8.4 Hz, ArH), 7.29(s, 1H, ArH), 7.60(d, 1H, J=15.9 Hz, CH=). MS (m/z): 317.2(M$^+$, 30), 218.2(M$^+$-99, 100), 189.1(M$^+$-99-29, 45).

Example 52c

5-[(N$_4$-Methyl)piperazyl]-1-(2,4-dichlorophenyl)-1-penten-3-one hydrochloride Compound No. 52c The title compound was prepared according to the method described in Example 52, using 4-(2,4-dichlorophenyl)-3-buten-2-one (prepared as described in preparation 11) as the starting material. mp: 151-155° C.

$^1$HNMR δppm (DMSO-d$_6$): 2.30(s, 2H, COCH$_2$), 2.49(s, 3H, NCH$_3$), 2.80-3.40(m, 10H, 5NCH$_2$), 6.84(d, 1H, J=16.5 Hz, =CHCO), 7.02(d, 1H, J=8.4 Hz, ArH), 7.29(d, 1H, J=8.4 Hz, ArH), 7.34(s, 1H, ArH), 7.65(d, 1H, J=16.5 Hz, CH=). MS (m/z): 318.4(M$^+$, 6), 218.2(M$^+$-99, 100), 187.2(M$^+$-99-31, 49).

Example 52d

5-[(N$_4$-Methyl)piperazyl]-1-(3,4-dimethoxyphenyl)-1-penten-3-one hydrochloride Compound No. 52d The title compound was prepared according to the method described in Example 52, using 4-(3,4-dimethoxyphenyl)-3-buten-2-one (prepared as described in preparation 15) as the starting material. mp: 190-193° C.

Example 52e

5-[(N$_4$-Methyl)piperazyl]-1-(4-ethoxy-3-methoxyphenyl)-1-penten-3-one hydrochloride Compound No. 52e The title compound was prepared according to the method described in Example 52, using 4-(4-ethoxy-3-methoxyphenyl)-3-buten-2-one (prepared as described in preparation 6) as the starting material. Mp: 158-161° C.

Example 53

5-[N$_4$-(3,4-Methylenedioxy(benzyl)piperazyl)]-1-(4-chlorophenyl)-1-penten-4-methyl-3-one hydrochloride Compound No. 53

0.146 g (0.5 mmol) of N$_4$-(3,4-methylenedioxy(benzyl) piperizine hydrochloride and 36% formaldehyde aqueous solution (1 ml) were dissolved in anhydrous ethanol (5 ml). The pH value of the solution was adjusted to pH=2-3.0 with concentrated hydrochloric acid and the reaction mixture was refluxed and stirred for 1.0 hr. After the solid was dissolved, 0.097 g (0.5mol) of 4-(4-chlorophenyl)-3-penten-2-one (prepared as described in preparation 17) was added to the above reaction mixture. The solution was further refluxed and stirred for 6 hr. After cooling with cold water bath, the precipitated solid was collected by filtration, and then recrystallized from acetone-anhydrous ethanol and dried to give 0.14 g of white crystals, yield: 28.1%, mp: 220-223° C.

$^1$HNMR δppm (DMSO-d$_6$): 1.16(brs, 3H, COCHCH$_3$), 2.49(brm, 13H, 5NCH$_2$+NCH$_2$Ph+COCHCH$_3$), 6.05($\overline{s, 2H}$, OCH$_2$O), 6.99(d, 2H, J=8.1 Hz, ArH), 7.1$\overline{0}$(d, 1H, J=16.2 Hz, =CHCO), 7.15(brs, 1H, ArH), 7.52(d, 2H, J=8.1 Hz, ArHAA'), 7.66(d, 1H, J=16.2 Hz, CH=), 7.79(d, 2H, J=8.1 Hz, ArHBB'). FAB-MS (m/z): 427.2($M^++1$, 100), 233.3($M^+-$193).

Example 54

5-[$N_4$-(3,4-Methylenedioxy(benzyl)piperazyl)]-1-(3,4,5-trimethoxy-phenyl)-1-penten-3-one hydrochloride Compound No. 54

0.146 g (0.5 mmol) of $N_4$-(3,4-methylenedioxy(benzyl) piperizine hydrochloride and 36% formaldehyde aqueous solution (1 ml) were dissolved in anhydrous ethanol (5 ml). The pH value of the solution was adjusted to pH=2-3.0 with concentrated hydrochloric acid and the reaction mixture was refluxed and stirred for 1 hr. After the solid was dissolved, 0.125 g (0.5 mol) of 4-(3,4,5-trimethoxyphenyl)-3-buten-2-one (prepared as described in preparation 7) was added to the above reaction mixture. The solution was further refluxed and stirred for 18 hr. After cooling with water bath, the precipitated white solid was collected by filtration and then recrystallized from anhydrous ethanol and dried to give 0.16 g of white acerate crystals, yield: 57.8%, mp: 150-152° C.
$^1$HNMR δppm (DMSO-$d_6$): 2.47-2.49(brm, 12H, 5$NCH_2$+$NCH_2$Ph), 3.68(s, 3H, $OCH_3$), 3.81(s, 6H, 2×$OCH_3$), 6.04(s, 2H, $OCH_2$O), 6.95(d, 2H, J=1.8 Hz, ArH), 7.01(d, 1H, J=15.6 Hz, =CHCO), 7.03-7.19(m, 3H, ArH), 7.61(d, 1H, J=15.6 Hz, CH=). MS (m/z): 482($M^+$, 18), 262 ($M^+-220$, 28), 221 ($M^++H$, 11), 135 (100).

Example 55

5-[$N_4$-(3,4-Methylenedioxy(benzyl)piperazyl)]-1-(3-ethoxy-4-methoxy-phenyl)-1-penten-3-one hydrochloride Compound No. 55

0.293 g (1.0 mmol) of $N_4$-(3,4-methylenedioxy(benzyl) piperizine hydrochloride and paraformaldehyde (0.3 g, 10 mmol) were dissolved in anhydrous ethanol (10 ml). The pH value was adjusted to pH=2-3.0 with concentrated hydrochloric acid and the reaction mixture was refluxed and stirred for 1 hr. After the solid was dissolved, 0.22 g (1.0mol) of 4-(3-ethoxy-4-methoxyphenyl)-3-buten-2-one (prepared as described in preparation 4) was added to the above reaction mixture. The solution was further refluxed and stirred for 6 hr. After cooling with water bath, the precipitated solid was collected by filtration and then recrystallized from anhydrous ethanol-acetone and dried to give 0.183 g of pale yallow needle crystals, yield: 53.8%, mp: 238-241° C.
$^1$HNMR δppm (DMSO-$d_6$): 1.33(t, 3H, J=7.2 Hz, $OCH_2CH_3$), 2.49(brm, 10H, 5$NCH_2$), 3.26-3.39(brm, 2H, $COCH_2$), 3.79(s, 3H, $OCH_3$), 4.05 (q, 2H, J=7.2 Hz, $OCH_2CH_3$), 4.31 (s, 2H, —$CH_2$Ph), 6.05(s, 2H, $OCH_2$O), 6.83(d, 1H, J=16.2 Hz, =CHCO), 6.99(d, 2H, J=7.2 Hz, ArH), 7.06(m, 1H, ArH), 7.23(dd, 2H, J=8.1 Hz, ArH), 7.32(m, 1H, ArH), 7.61 (d, 1H, J=16.2 Hz, CH=). FAB-MS (m/z): 453.4($M^++1$, 100).

Example 56

5-[$N_4$-(3,4-Methylenedioxy(benzyl)piperazyl)]-1-(4-chlorophenyl)-1-penten-3-one hydrochloride Compound No. 56

0.293 g (1.0 mmol) of $N_4$-(3,4-methylenedioxy(benzyl) piperizine hydrochloride and paraformaldehyde (0.3 g, 10 mmol) were dissolved in anhydrous ethanol (10 ml). The pH value was adjusted to pH=2-3.0 with concentrated hydrochloric acid and the reaction mixture was refluxed and stirred for 1 hr. After the solid was dissolved, 0.194 g (1.0 mol) of 4-(4-chlorophenyl)-3-buten-2-one (prepared as described in preparation 1) was added to the above reaction mixture. The solution was further refluxed and stirred for 6 hr. After cooling with water bath, the precipitated solid was collected by filtration and then recrystallized from anhydrous ethanol-acetone and dried to give 0.29 g of white needle crystals, yield: 59.8%, mp: 250-252° C.
$^1$HNMR δppm (DMSO-$d_6$): 2.49(brm, 10H, 5$NCH_2$), 4.31 (s, 2H, —$NCH_2$Ph), 6.05(s, 2H, $OCH_2$O), 6.95(d, 1H, J=16.2 Hz, =CHCO), 7.04(d, 2H, J=9 Hz, ArH), 7.18(s, 1H, ArH), 7.52(d, 2H, J=8.1 Hz, ArH$_{AA'}$), 7.67(d, 1H, J=16.2 Hz, CH=), 7.76(d, 2H, J=8.1 Hz, ArH$_{BB'}$). FAB-MS (m/z): 413.3 ($M^++1$, 100), 233.3($M^+-179$).

Example 57

5-[($N_4$-2-Methoxyphenyl)piperazyl)]-1-(3-chlorophenyl)-1-penten-3-one hydrochloride Compound No. 57

0.265 g (1.0 mmol) of $N_4$-(2-methoxyphenylpiperizine hydrochloride and paraformaldehyde (0.3 g, 10 mmol) were dissolved in anhydrous ethanol (9 ml). The pH value was adjusted to pH=2-3.0 with concentrated hydrochloric acid and the reaction mixture was refluxed and stirred for 1 hr. After the solid was dissolved, 0.18 g (1.0 mol) of 4-(3-chlorophenyl)-3-buten-2-one (prepared as described in preparation 24) was added to the above reaction mixture. The solution was further refluxed and stirred for 15 h. TLC showed the reaction was completed. After cooling with water bath, the precipitated pale yellow solid was collected by filtration dried and then recrystallized from anhydrous ethanol and dried to give 0.26 g of white crystals, yield: 67.7%, mp: 176-178° C.
$^1$HNMR δppm (DMSO-$d_6$): 3.78(s, 3H, $OCH_3$), 3.0 (m, 10H, 5$NCH_2$), 6.87-6.99(m, 4H, ArH), 7.03(d, 1H, J=16.2 Hz, =CHCO), 7.46(d, 3H, Ar—H), 7.72(d, 1H, J=16.2 Hz, CH=), 7.85(s, 1H, Ar—H). MS (m/z): 384($M^+$, 18), 339 ($M^+-15$, 5), 192($M^+-192$, 60).

Example 58

5-[($N_4$-2-Methoxyphenyl)piperazyl)]-1-(4-chlorophenyl)-1-penten-3-one hydrochloride Compound No. 58

0.265 g (1.0 mmol) of $N_4$-(2-methoxyphenylpiperizine hydrochloride and paraformaldehyde (0.3 g, 10 mmol) were dissolved in anhydrous ethanol(9 ml). then the pH value was adjusted to pH=2-3.0 with concentrated hydrochloric acid and the reaction mixture was refluxed and stirred for 1 h. After the solid was dissolved, 0.18 g (1.0 mol) of 4-(4-chlorophenyl)-3-buten-2-one (prepared as described in preparation 1) was added to the above reaction mixture. The solution was further refluxed and stirred for 15 hr. After cooling with water bath, the precipitated pale yellow solid was collected by filtration and then recrystallized from anhydrous ethanol and dried to give 0.201 g of white crystals, yield: 52.3%, mp: 180-182° C.
$^1$HNMR δppm (DMSO-$d_6$): 3.78(s, 3H, $OCH_3$), 3.0 (m, 10H, 5$NCH_2$), 6.87-6.99(m, 4H, ArH), 7.05(d, 1H, J=16.2 Hz, =CHCO), 7.54(d, 2H, J=8.4 Hz, Ar—H), 7.76(d, 1H, J=16.2 Hz, CH=), 7.83(d, 2H, J=8.4 Hz, Ar—H). MS (m/z): 384(M+, 6), 339(M+−15, 3), 193(M+−191, 40).

Example 59

5-[(N₄-2-Methoxyphenyl)piperazyl)]-1-(4-chlorophenyl)-1-penten-4-methyl-3-one hydrochloride Compound No. 59

0.265 g (1.0 mmol) of N₄-(2-methoxyphenyl)piperizine hydrochloride and 36% formaldehyde aqueous solution (1 ml) were dissolved in anhydrous ethanol (5 ml). The pH value was adjusted to pH=2-3.0 with concentrated hydrochloric acid and the reaction mixture was refluxed and stirred for 1 hr. After the solid was dissolved, 0.19 g(1.0 mol) of 4-(4-chlorophenyl)-3-penten-2-one (prepared as described in preparation 17) was added to the above reaction mixture. The solution was further refluxed and stirred for 6 hr. After cooling with water bath, the precipitated pale yellow solid was collected by filtration and then recrystallized from anhydrous ethanol and dried to give 0.13 g of white crystals, yield: 27.6%, mp: 139-140° C.

¹HNMR δppm (DMSO-d₆): 1.23(d, 3H, J=6.6 Hz, COCHCH₃), 2.49(q, 1H, J=6.6 Hz, COCHCH₃), 3.77(s, 3H, OCH₃), 3.0(m, 10H, 5NCH₂), 6.91-6.99(m, 4H, ArH), 7.13(d, 1H, J=16.2 Hz, =CHCO), 7.52(d, 2H, J=8.4 Hz, ArH$_{AA'}$), 7.72(d, 1H, J=116.2 Hz, CH=), 7.80(d, J=8.4 Hz, 2H, ArH$_{BB'}$). MS (m/z): 398(M+, 16), 383(M+−15, 3), 205(M+−193, 100), 192 (M+−206, 40).

Example 60

1-(3,4-Methylenedioxyphenyl)-3-[(N₄-ethoxycarbonyl)piperazyl]-1-oxo-propane hydrochloride Compound No. 60

0.38 g (2.0 mmol) of N₄-ethoxycarbonylpiperizine hydrochloride and 0.3 g (10 mmol) of paraformaldehyde were dissolved in anhydrous ethanol (5 ml). The pH value was adjusted to pH=4.5-5.0 with concentrated hydrochloric acid. The solution was heated and stirring at reflux for 0.5 hr. After the solid was dissolved, 0.16 g (1 mmol) of 3,4-methylene-dioxy-acetophenone (prepared as described in preparation 25) was added to the above reaction mixture. The solution was stirred and heated at reflux for 13 hr. After cooling with water bath, the precipitated pale yellow solid was collected by filtration, dried and then recrystallized from anhydrous ethanol and dried to give 0.29 g of white crystals, yield: 75.9%, mp: 170-172° C.

¹HNMR δppm (DMSO-d₆): 1.24(t, J=7.2 Hz, 3H, COOCH₂CH₃), 3.00-3.60(m, 10H, 5NCH₂), 4.08(q, 4H, J=7.2 Hz, COOCH₂CH₃+COCH₂), 6.12(s, 2H, OCH₂O), 6.97(d, 1H, J=7.2 Hz, ArH), 7.44(d, 1H, J=1.8 Hz, ArH), 7.64(dd, 1H, J=7.2 Hz, J=1.8 Hz, ArH). MS (m/z): 334(M+, 12), 289(5), 232(10).

Example 61

5-[(N₄-Benzoyl)piperazyl]-1-(3,4-methylenedioxyphenyl)-1-penten-3-one hydrochloride Compound No. 61

0.19 g (1.0 mmol) of N₄-benzoylpiperizine hydrochloride and 0.3 g (10 mmol) of paraformaldehyde were dissolved in anhydrous ethanol (5 ml ). The pH value was adjusted to pH=1.0-1.5 with concentrated hydrochloric acid and the reaction mixture was refluxed and stirred for 1 hr. After the solid was dissolved, 0.19 g (1.0mol) of 4-(3,4-methylene-dioxyphenyl)-3-buten-2-one (prepared as described in preparation 15) was added to the above reaction mixture. The solution was further refluxed and stirred for 15 hr. After cooling with water bath, the precipitated pale yellow solid was collected by filtration, dried and then recrystallized from anhydrous ethanol and dried to give 0.16 g of white crystals, yield: 40.8%, mp: 178-181° C.

¹HNMR δppm (DMSO-d₆): 3.00-3.40(m, 12H, 5NCH₂+COCH₂), 6.06(s, 2H, OCH₂O), 6.74(d, 1H, J=16.2 Hz, =CHCO), 6.92(d, 1H, J=7.2 Hz, Ar(a)H), 7.17-7.20(m, 7H, Ar(b)5H+ Ar(a)2H), 7.60(d, 1H, J=16.2 Hz, CH=).
MS (m/z): 392(M+, 12), 287(2), 245(8), 202(87).

Example 62

5-[(4-Methyl)piperidyl]-1-(3,4-methylenedioxyphenyl)-1-penten-3-one hydrochloride Compound No. 62

0.43 g (3.0 mmol) of 4-methylpiperidine hydrochloride and 0.3 g (10 mmol) of paraformaldehyde were dissolved in anhydrous ethanol (30 ml). The pH value was adjusted to pH=2.0-2.5 with concentrated hydrochloric acid and the reaction mixture was refluxed and stirred for 1 hr. After the solid was dissolved, 0.57 g (3.0 mol) of 4-(3,4-methylene-dioxy) phenyl-3-buten-2-one (prepared as described in preparation 15) was added to the above reaction mixture. The solution was stirred and heated at reflux for 20 hr. After cooling with water bath, the precipitated yellow solid was collected by filtration dried and then recrystallized from anhydrous ethanol and dried to give 0.48 g of pale yellow crystals, yield: 47.5 %, mp: 163-166° C.

¹HNMR δppm (DMSO-d₆): 0.92(d, 3H, J=6.0 Hz, CHCH₃), 1.48(brs, 5H, 2CH₂+CHCH₃), 3.20-3.45(m, 6H, 3NCH₂), 4.18(s, 2H, COCH₂), 6.07(s, 2H, OCH₂O), 6.77(d, 1H, J=16.2 Hz, =CHCO), 6.95(d, 1H, J=8.1 Hz, ArH), 7.22 (dd, 1H, J=8.1 Hz, J=1.8 Hz, ArH), 7.37(d, 1H, J=1.8 Hz, ArH), 7.62(d, 1H, J=16.2 Hz, CH=). MS (m/z): 301(M+, 50), 202(15), 175(18), 112 (100).

Example 63

5-[N₄-(2,3,4-Trimethoxy(benzyl)piperazyl)]-1-(4-hydroxyphenyl)-1-penten-3-one hydrochloride Compound No. 63

1.69 g (5.0 mmol) of N₄-(2,3,4-trimethoxy(benzyl)piperidine hydro-chloride and 0.65 g (21.5 mmol) of paraformaldehyde were dissolved in anhydrous ethanol (20 ml). The pH value was adjusted to pH=2.0-3.0 with concentrated hydrochloric acid and the reaction mixture was refluxed and stirred for 1 hr. After the solid was dissolved, 1.57 g (9.5mol) of 4-(4-hydroxyphenyl)-3-buten-2-one (prepared as described in preparation 2) was added to the above reaction mixture. The solution was stirred and heated at reflux for 4 hr. After cooling with water bath, the precipitated yellow solid was collected by filtration, dried and then recrystallized from methanol-water and dried to give 1.42 g of white needle crystals, yield: 55.4%, mp: 191-193° C.

¹HNMR δppm (DMSO-d₆): 2.56-2.77(brm, 10H, 5NCH₂), 3.82(s, 6H, 2×OCH₃), 3.87(s, 3H, OCH₃), 4.31(s, 2H, —NCH₂Ph), 6.67(d, 1H, J=17 Hz, =CHCO), 6.85(d, 2H, J=9 Hz, ArH$_{AA'}$), 7.29(d, 2H, J=9 Hz, ArH$_{BB'}$), 7.55(m, 1H, ArH), 7.59(d, 1H, J=17 Hz, CH=), 7.81(m, 1H, ArH).

MS (m/z): 440(M+, 2), 266(M+−174, 11), 235(M+−205, 9), 181(M+−259, 100). IR cm$^{-1}$: 1655, 1620, 1595, 1260, 830.

Example 64

1-(3,4-Methylenedioxy-5-methoxyphenyl)-3-[(N$_4$-ethoxycarbonyl)piperazyl]-1-oxo-propane hydrochloride Compound No. 64

0.195 g (1.0 mmol) of N$_4$-ethoxycarbonylpiperizine hydrochloride and 0.3 g (10 mmol) of paraformaldehyde were dissolved in anhydrous ethanol (5 ml ). The pH value was adjusted to pH=2.0-3.0 with concentrated hydrochloric acid and the reaction mixture was refluxed and stirred for 1 hr. After the solid was dissolved, 0.19 g (1 mmol) of 3,4-methylenedioxy-5-methoxy-acetophenone (prepared as described in preparation 14) was added to the above reaction mixture. The solution was stirred and heated at reflux for 13 hr. After cooling with water bath, the precipitated white solid was collected by filtration, dried and then recrystallized from anhydrous ethanol and dried to give 0.25 g of white crystals, yield: 62.6%, mp: 193-195° C.

$^1$HNMR δppm (DMSO-d$_6$): 1.21(t, 3H, J=7.2 Hz, COOCH$_2$CH$_3$), 3.00-3.40(m, 10H, 5NCH$_2$), 3.89(s, 3H, OCH$_3$), 3.96-4.20(m, 4H, COOCH$_2$CH$_3$+COCH$_2$), 6.10(s, 2H, OCH$_2$O), 7.21(d, 1H, J=0.8 Hz, ArH), 7.29(d, 1H, J=0.8 Hz, ArH). MS (m/z): 364(M+, 13), 319(3), 262(9).

Anal. Cald. for C$_{18}$H$_{25}$N$_2$O$_6$Cl: C, 53.93%; H, 5.99%; N, 7.04%. Found: C, 53.82%; H, 5.98%; N, 6.99%.

Example 65

1-(4-Chlorophenyl)-3-[(N$_4$-ethoxycarbonyl)piperazyl]-1-oxo-propane hydrochloride Compound No. 65

0.195 g (1.0 mmol) of N$_4$-ethoxycarbonylpiperizine hydrochloride and 0.3 g (10 mmol) of paraformaldehyde were dissolved in anhydrous ethanol (5 ml). The pH value was adjusted to pH=1.0-2.5 with concentrated hydrochloric acid and the reaction mixture was refluxed and stirred for 1 hr. After the solid was dissolved, 0.15 g (1 mmol) of 4-(4-chloro) acetophenone (prepared as described in preparation 26) was added to the above reaction mixture. The solution was stirred and heated at reflux for 13 hr, after cooling with water bath, the precipitated white solid was collected by filtration, dried and then recrystallized from anhydrous ethanol and dried to give 0.25 g of white crystals, yield: 69.4%, mp: 162-166° C.

$^1$HNMR δppm (DMSO-d$_6$): 1.24(t, 3H, J=7.2 Hz, COOCH$_2$CH$_3$), 3.00-3.60(m, 10H, 5NCH$_2$), 3.88-4.16(m, 4H, COOCH$_2$CH$_3$+COCH$_2$), 7.62(d, 2H, J=8.1 Hz, ArH$_{AA'}$), 8.00(d, J=8.1 Hz, 2H, ArH$_{BB'}$). MS (m/z): 324(M+, 5), 279(4), 251(3), 185(5).

Example 66

Phenyl-1,3-heptene-7-[4-(ethoxycarbonyl)piperidyl]-5-one hydrochloride Compound No. 66

0.195 g (1.0 mmol) of 4-ethoxycarbonylpiperidine hydrochloride and 0.6 g (20 mmol) of paraformaldehyde were dissolved in anhydrous ethanol (10 ml ). The pH value was adjusted to pH=2.0-3.0 with concentrated hydrochloric acid and the reaction mixture was refluxed and stirred for 0.5 hr. After the solid was dissolved, 0.344 g (2 mmol) of phenyl-1,3-hexadiene-5-one (commercially available) was added to the above reaction mixture. The solution was stirred and heated at reflux for 10 hr. The reaction solution was evaporated to remove ethanol. After cooling with water bath, the precipitated solid was collected by filtration, dried and then recrystallized from 95% ethanol and dried to give 0.15 g of white crystals, yield: 19.8%, mp: 160-161° C.

$^1$HNMR δppm (DMSO-d6): 1.18(t, 3H, J=7.2 Hz, COOCH$_2$CH$_3$), 1.79-2.26(m, 5H, (CH$_2$)$_2$CHCO), 3.2-3.61 (m, 6H, 3NCH$_2$), 4.09(q, 2H, OCH$_2$CH$_3$), 6.35(d, 1H, J=15.6 Hz, =CHCO), 7.16(m, 2H, ArH, CH=), 7.32-7.52(m, 4H, ArH), 7.59(d, 2H, J=7.2 Hz, CH=).

FAB-MS (m/z): 342.6(M++1).

Example 67

5-[(4-Carboxylic acid)piperidyl]-1-(4-chlorophenyl)-1-penten-3-one hydrochloride Compound No. 67

A mixture of 10 g (26 mmol) of 5-[(4-ethoxycarbonyl) piperidyl]-1-(4-chlorophenyl)-1-penten-3-one hydrochloride and 1N hydrochloride aqueous solution (600 ml) was heated and stirring at 90° C. for 2 hr. After the solid was dissolved, the reaction solution was concentrated under reduced pressure, the precipitated solid was collected by filtration, washed with water and acetone successively, dried and then recrystallized from anhydrous ethanol and dried to give 4.85 g of white crystals, yield: 52.3%, mp 174-176° C.

$^1$HNMR δppm (500 MHz, DMSO-d6): 1.816-3.50(m, 13H, —CH$_2$CH$_2$—N(CH$_2$CH$_2$)$_2$CHCO), 6.91(d, 1H, J=16.5 Hz, =CHCO), 7.51(d, 2H, J=8.5 Hz, ArH$_{AA'}$), 7.70(d, 1H, J=16.5 Hz, CH=), 7.76(d, 2H, J=8.1 Hz, ArH$_{BB'}$), 10.57(s, 1H, COOH, D$_2$O exchange).

MS (m/z): 321.0(M+, 20), 191.9(55), 164.9(80), 157.0(100).

Example 68

5-[4-(Ethoxycarbonyl)piperidyl]-1-(4-chlorophenyl)-pentan-3-one hydrochloride Compound No. 68

A solution of 6.16 g (16 mmol) 5-[(4-ethoxycarbonyl) piperidyl]-1-(4-chlorophenyl)-1-penten-3-one hydrochloride in 500 ml anhydrous ethanol was hydrogenated at atmospheric pressure in the presence of 0.448 g of 10% Pd/C. Until hydrogen can not be absorbed any more, the catalyst was filtered off, and the filtrate was concentrated under reduced pressure. The solid was collected by filtration, dried and then recrystallized from anhydrous ethanol and dried to give 2 g of white crystals, yield: 32.2%, mp: 125-127□.

$^1$HNMR: δppm (300 MHz, DMSO-d$_6$), 1.18(t, 3H, J=7.2 Hz, COOCH$_2$—CH$_3$), 1.74-3.45(m, 17H, —CH$_2$CH$_2$CO CH$_2$CH$_2$N(CH$_2$CH$_2$)$_2$CHCOO—), 4.07(q, 2H, J=7.2 Hz, COOCH$_2$CH$_3$), 7.23(d, 2H, J=8.5 Hz, ArH$_{AA'}$), 7.32(d, 2H, J=8.5 Hz, ArH$_{BB'}$). MS (m/z): 352.7(M++H, 100), 318.5(15.6), 170.4(7.5).

Example 69

5-[4-(Carboxylic acid)piperidyl]-1-(4-chlorophenyl)-pentan-3-one hydrochloride Compound No. 69

A solution of 2.0 g (5.6 mmol) 5-[(4-carboxylicacid)piperidyl]-1-(4 -chlorophenyl)-1-penten-3-one hydrochloride in anhydrous ethanol (200 ml) was hydrogenated at atmospheric pressure in the presence of 0.15 g of 10% Pd/C. Until hydrogen can not be absorbed any more, the catalyst was filtered off, and the filtrate was concentrated under reduced pressure.

The solid was collected by filtration, washed with ether and petroleum ether, dried to give 1.2 g of white solids, yield: 59.7%, mp 126-128° C.

$^1$HNMR: δ ppm (300 MHz, DMSO-d$_6$): 1.82-3.32 (m, 17H, —CH$_2$CH$_2$COCH$_2$CH$_2$N(CH$_2$)$_4$CHCOO—), 7.23 (d, 2H, J=8.5 Hz, ArH$_{AA'}$), 7.32 (d, 2H, J=8.5 Hz, ArH$_{BB'}$), 12.55 (s, 1H, COOH, D$_2$O exchange).

MS (m/z): 323 (M$^+$, 4), 198 (6), 194 (75), 159 (30), 142 (86), 139 (43), 129 (27), 125 (73).

Example 70

5-[(4-Ethoxycarbonyl)piperidyl]-1-(4-chlorophenyl)-1-penten-3-ol Hydrochloride Compound No. 70

A mixture of 5-[(4-ethoxycarbonyl)piperidyl]-1-(4-chlorophenyl)-1-penten-3-one hydrochloride (4 g, 10.4 mmol) and ethyl acetate (300 ml) was neutralized with 300 ml of saturated NaHCO$_3$ solution under cooling with ice water bath, and the free base was extracted from the aqueous mixture with ethyl acetate. Then the ethyl acetate layer was separated, washed with brine, dried with sodium sulfate and the ethyl acetate layer was concentrated under reduced pressure. The solid was collected by filtration, dried to give 3.78 g of the free base, yield: 96.6%, mp: 82-85° C.

5-[(4-Ethoxycarbonyl)piperidyl]-1-(4-chlorophenyl)-1-penten-3-one(3 g, 8.6 mmol) was dissolved in 40m1 of the CeCl$_3$.7H$_2$O (6 g) anhydrous methanol solution. Sodium borohydride (0.325 g) was slowly added with strring under cooling with ice water bath. The reaction solution was allowed to react at room temperature for 10-15 min, followed by hydrolysis with saturated NaHCO$_3$ aqueous solution and extracted with ethyl acetate, then the ethyl acetate layer was separated, washed with brine, dried over sodium sulfate and the ethyl acetate layer was concentrated under reduced pressure. The solid was produced by the addition of concentrated HCl. The precipitated was recrystallized from anhydrous ethanol and dried to give 1.87 g of white crystals, yield: 61.7%, mp: 72-73° C.

$^1$HNMR: δppm (400 MHz, DMSO-d$_6$): 1.16(t, 3H, J=7.2 Hz, COOCH$_2$ CH$_3$), 1.48-3.31(m, 13H, —CH$_2$CH$_2$N(CH$_2$CH$_2$)$_2$CHCOO—), 4.04(q, 2H, J=7.2 Hz, COOCH$_2$CH$_3$), 4.19(m, 1H, —CHOH—), 5.16(s, 1H, —OH, D$_2$O exchange), 6.32(q, 1H, J=16 Hz, =CH—), 6.50(d, 1H, J=16 Hz, —HC=), 7.35(d, 2H, J=8.8 Hz, ArH$_{AA'}$), 7.43(d, 2H, J=8.4 Hz, ArH$_{BB'}$).

MS (m/z): 351(M$^+$, 9), 212(15), 182(11), 170(100), 142 (21).

Example 71

5-[(4-Carboxylic acid)piperidyl]-1-(4-chlorophenyl)-1-penten-3-ol hydrochloride Compound No. 71

The title compound was prepared according to the method described in example 70, using 5-[(4-carboxylic acid)piperidyl]-1-(4-chlorophenyl)-1-penten-3-one (Compound No. 67) as the starting material.

$^1$HNMR: δppm (400 MHz, DMSO-d$_6$) 1.96-3.62(m, 13H, —CH$_2$CH$_2$N(CH$_2$CH$_2$)$_2$CHCOO—), 4.44(s, 1H, — CHOH—), 4.83(s, 1H, —OH, D$_2$O exchange), 5.55(s, 1H, —OH, D$_2$O exchange), 6.49(d, 1H, J=17.2 Hz, =CH—), 6.64(d, 1H, J=16 Hz, —HC=), 7.40(d, 2H, J=8 Hz, ArH$_{AA'}$), 7.52(d, 2H, J=8 Hz, ArH$_{BB'}$). MS (m/z): 323.1(M$^+$, 8), 184.1 (13), 142.1(100), 128.1(15).

PHARMACOLOGICAL EXPERIMENTS

Experimental Example 1

The Inhibition of the Compounds on the Release of β-Glucuronidase by Polymorphonuclear Leucocytes from Rat Pleural Cavity In Vitro 1% carrageenan was injected into the right pleural cavity of Wistar rat to induce polymorphonuclear leucocytes. The cells was suspended in Dulbecoo's buffer at the concentration of $2.5 \times 10^6$ cells·ml$^1$. The fluid containing the compound or solvent and 250 μl of cells suspension were added in test tube and incubated in 37° C. waterbath for 15 min. Then 2.5 μl of cytochalasin B ($1 \times 10^{-3}$ mol·L$^{-1}$) was added and the reaction was continued for 5 min. Then 2.5 μl of PAF ($1 \times 10^{-4}$ mol·L$^{-1}$) was added and for another 5 min. The test tubes were put into ice bath to stop the reaction. The supernatant was isolated and used as the β-glucuronidase release fluid. 25 μl of the enzyme fluid, 25 μl of phenolphthalein-glucuronic acid (2.5 mmol·L$^{-1}$) and 100 μl of acetic acid buffer (0.1 mol·L$^{-1}$) were added into each well of 96-well plate which was placed into incubater and kept at 37° C.3 for 18 hr. 150 μl of NaOH (0.3 mol·L$^{-1}$) was added in each well to cease the reaction and the optical density was read at 550 nm.

The results show that compounds have significant effect on the release of β-glucuronidase by polymorphonuclear leucocytes. It is suggested that the inhibition of compounds on the release of lysosomal enzyme maybe contribute to their anti-inflammatory action. Moreover, these compounds are perhaps the potential PAF receptor antagonists.

TABLE 1

The results of β-glucuronidase release assay

| Compounds | Dose (mol · L$^{-1}$) | Irritant (mol · L$^{-1}$) | Inhibition (%) |
|---|---|---|---|
| 28 | $1 \times 10^{-4}$ | $2 \times 10^{-7}$ | 21.8 |
| 32 | $1 \times 10^{-4}$ | " | 46.1 |
| 51 | $1 \times 10^{-4}$ | " | 55.1 |
| 52 | $1 \times 10^{-4}$ | " | 31.2 |
| 4 | $1 \times 10^{-5}$ | $1 \times 10^{-6}$ | 28.05 |
| 5 | $1 \times 10^{-5}$ | " | 45.34 |
| 6 | $1 \times 10^{-5}$ | " | 39.53 |
| 10 | $1 \times 10^{-5}$ | " | 51.07 |
| 13 | $1 \times 10^{-5}$ | " | 20.56 |
| 14 | $1 \times 10^{-5}$ | " | 36.65 |
| 17 | $1 \times 10^{-5}$ | " | 37.64 |
| 20 | $1 \times 10^{-5}$ | " | 104.03 |
| 22b | $1 \times 10^{-5}$ | " | 41.79 |
| 22a | $1 \times 10^{-5}$ | " | 73.17 |
| 22 | $1 \times 10^{-5}$ | " | 69.00 |
| 23 | $1 \times 10^{-5}$ | " | 32.27 |
| 29 | $1 \times 10^{-5}$ | " | 22.22 |
| 30 | $1 \times 10^{-5}$ | " | 23.54 |
| 33b | $1 \times 10^{-5}$ | " | 33.02 |
| 34d | $1 \times 10^{-5}$ | " | 62.64 |
| 39b | $1 \times 10^{-5}$ | " | 40.48 |
| 39c | $1 \times 10^{-5}$ | " | 28.66 |
| 48 | $1 \times 10^{-5}$ | " | 25.87 |
| 49 | $1 \times 10^{-5}$ | " | 43.19 |
| 53 | $1 \times 10^{-5}$ | " | 37.82 |
| 54 | $1 \times 10^{-5}$ | " | 65.88 |
| 55 | $1 \times 10^{-5}$ | " | 27.24 |
| 58 | $1 \times 10^{-5}$ | " | 21.31 |
| 2 | $2 \times 10^{-6}$ | $1 \times 10^{-7}$ | 126.36 |
| 3 | $2 \times 10^{-6}$ | " | 142.96 |
| 8 | $1 \times 10^{-5}$ | " | 158.42 |
| 12 | $1 \times 10^{-5}$ | " | 181.48 |
| 15 | $1 \times 10^{-5}$ | " | 141.17 |
| 16 | $2 \times 10^{-6}$ | " | 84.38 |
| 24 | $1 \times 10^{-5}$ | " | 120.85 |
| 34a | $2 \times 10^{-6}$ | " | 121.34 |
| 19 | $1 \times 10^{-5}$ | $2 \times 10^{-7}$ | 79.01 |

TABLE 1-continued

The results of β-glucuronidase release assay

| Compounds | Dose (mol · L$^{-1}$) | Irritant (mol · L$^{-1}$) | Inhibition (%) |
|---|---|---|---|
| 36 | 1 × 10$^{-5}$ | " | 129.72 |
| 37 | 1 × 10$^{-5}$ | " | 79.24 |
| 43a | 1 × 10$^{-5}$ | " | 38.04 |
| 44a | 1 × 10$^{-5}$ | " | 52.46 |
| 44b | 1 × 10$^{-5}$ | " | 57.93 |
| 45a | 1 × 10$^{-5}$ | " | 26.87 |
| 47a | 1 × 10$^{-5}$ | " | 44.58 |
| 1 | 1 × 10$^{-5}$ | 5 × 10$^{-7}$ | 97.87 |

TABLE 2

IC$_{50}$ of part of effective compounds on release of β-glucuronidase

| Compounds | IC$_{50}$ (mol · L$^{-1}$) |
|---|---|
| 3 | 2.26 × 10$^{-10}$ |
| 16 | 2.24 × 10$^{-8}$ |
| 20 | 3.08 × 10$^{-7}$ |
| 22a | 5.62 × 10$^{-7}$ |
| 36 | 5.55 × 10$^{-10}$ |
| 37 | 1.23 × 10$^{-9}$ |

Experimental Example 2

The Competitive Effect of Compound on the Binding Between [$^3$H]and its Receptors of Rat Polymorphonuclear Leucocytes In Vitro The suspension of rat polymorphonuclear leucocytes was prepared. 240 μl of cells suspension (2×10$^6$cells·ml$^{-1}$), 5 μl of [$^3$H](5 μmol·L$^1$) were added into each well. 5 μl of unlabeled PAF (5 μl mol·L$^{-1}$)was added into the well for the nonspecific binding. The series concentrations of compound were added into the well for the competitive binding and the corresponding volume of solvent was added into the wells for the total binding or the nonspecific binding. The reaction was kept in water bath at 37° C. for 30 min and stopped by ice bath. Reaction fluid was filtrated using the filter membrane which was rinsed by cold buffer to separate the free labeled ligand. The filter membrane was dried at 80° C. and placed into a vial for scintillation in which 5 ml of scintillation agent was poured. The radioactivity strength was measured by scintillation counter.

The result shows that the compound has significant competitive effect on the binding between [$^3$H]and its receptor of rat polymorphonuclear leucocytes. It is suggested that the compound was characterized as a PAF receptor antagonist. For this reason, it maybe has the anti-inflammatory action.

The competitive effect of the compound on the binding between [$^3$H]-PAF and its receptors of rat polymorphonuclear leucocytes in vitro

| compound | IC$_{50}$ (mol · L$^{-1}$) |
|---|---|
| 20 | 5.5 × 10$^{-5}$ |

Experimental Example 3

The Competitive Effect of the Compounds on the Binding Between [$^3$H]-PAF and its Receptors of Rabbit Platelet In Vitro The blood was collected from the central artery and anti-coagulated. The rich platelet layer of plasma was isolated and the suspension of platelet was prepared with concentration of 1×10$^8$ ml$^{-1}$. 240μl of platelet suspension, 5 μl [$^3$H](1.16 nmol·L$^1$) were added into each well. 5μl of unlabeled PAF (5 μmol·L$^1$) was added into the well for the nonspecific binding. The series concentrations of compound were added into the well for the competitive binding and the corresponding volume of solvent was added into the wells for the total binding or the nonspecific binding. Reaction was kept at 25° C. for 30 min and stopped by ice bath. Reaction fluid was filtrated by filter membrane which was rinsed and dried. The filter was placed into a vial for scintillation in which 5 ml of scintillation fluid was added. The radioactivity was counted by scintillation counter.

The result shows that the compounds have significant competitive effect on the binding between [$^3$H]-PAF and its receptors of rabbit platelet. It is suggested that the compounds were characterized as PAF receptor antagonists and perhaps have the antithrombosis action.

The competitive effect of the compounds on the binding between [$^3$H]-PAF and its receptors of rabbit platelet in vitro

| Compounds | IC$_{50}$ (mol · L$^{-1}$) |
|---|---|
| 20 | 5.48 × 10$^{-5}$ |
| 22a | 1.21 × 10$^{-5}$ |

Experimental Example 4

The Competitive Effect of the Compounds on the Binding Between [$^3$H]-PAF and its Receptors of Macrophages from Mouse Peritoneal Cavity In Vitro 4% of sodium mercaptoethanol was injected into C57BL/6 mouse peritoneal cavity to induce macrophages. The cells in peritoneal cavity were collected after injection for 3-4 days. 500 μl of suspension (5×10$^5$cells·ml$^{-1}$) was inoculated into 24-well culture plate which was placed into the incubator with 5% CO$_2$ at 37° C for 2.5 hr. The non-adherent cells and serum in media were discarded. 490 μl of Tyrode-Hepes solution and 5 μl of [$^3$H]-PAF (final concentration: 2.8 nmol·L$^{-1}$) were added into each well. 5 μl of unlabeled PAF (5 μmol·L$^1$) was added into the well for the nonspecific binding. The series concentrations of compound were added into the well for the competitive binding and the corresponding volume of solvent was added into the wells for the total binding or the nonspecific binding. The reaction fluid was incubated at 4° C for 150 min and rinsed to wipe off the free labeled ligand. 300 μl of NaOH (0.3 mol·L$^{-1}$) was added to lyse the cells. The lysate fluid was transferred into a vial in which 7 ml of scintillation solution was added. The radioactivity strength was measured by scintillation counter.

The result shows that the compounds have significant competitive effect on binding between [$^3$H]-PAF and its receptors of macrophages from mouse peritoneal cavity. It is suggested that the compounds were characterized as PAF receptor antagonists and perhaps have the anti-inflammatory action.

| The competitive effect of the compounds on the binding between [$^3$H]-PAF and its receptors of macrophages from mouse peritoneal cavity | |
| --- | --- |
| Compounds | Ki (mol · L$^{-1}$) |
| 3 | 4.40 × 10$^{-6}$ |
| 37 | 6.83 × 10$^{-5}$ |
| 36 | 4.81 × 10$^{-5}$ |

Experimental Example 5

The Inhibition of the Compounds on the Chemotaxis of Rat Neutrophils In Vitro

The blood was collected from rat common carotid artery and anticoagulated. The neutrophils was isolated by 5% glucose solution and lymphocyte separating medium. 27 μl of irritant was added into the well at low part of the chemotaxis plate. The filter membrane was covered on the wells and the top part of the plate was assembled on the filter. 50 μl of cells suspension with various concentrations of compound or solvent was added into the well at top part of the plate. The plate was incubated at 37° C. for 4 hr. The filter was taken out, stained by hematoxylin and dehydrated. The cells migrated into the other side of the filter was counted by microscope.

The result shows that the compounds have significant inhibition on the chemotaxis of rat neutrophils which maybe is one of the mechanisms underlying its anti-inflammatory action.

| The inhibition of the compounds on the chemotaxis of rat neutrophils in vitro | |
| --- | --- |
| Compounds | IC$_{50}$ (mol · L$^{-1}$) |
| 20 | 3.35 × 10$^{-7}$ |
| 22a | 4.05 × 10$^{-9}$ |

Experimental Example 6

The Inhibition of the Compounds on the Chemotaxis of Macrophages from Mouse Peritoneal Cavity In Vitro stained by hematoxylin and dehydrated. The cells migrated into the other side of the filter was counted by microscope. stained by hematoxylin and dehydrated. The cells migrated into the other side of the filter was counted by microscope.

4% of sodium mercaptoethanol was injected into C57BL/6 mouse peritoneal cavity to induce macrophages. The cells in peritoneal cavity were collected after injection for 3-4 days. 27 μl of irritant was added into the well at low part of the chemotaxis plate. The filter membrane was covered on the wells and the top part of the plate was assembled on the filter. 55 μl of cells suspension with various concentrations of the compounds or solvent was added into the well at top part of the plate. The plate was placed into incubater with 5% CO$_2$ at 37° C. for 2 hr. The filter was taken out, stained by hematoxylin and dehydrated. The cells migrated into the other side of the filter was counted by microscope.

The result shows that the compounds have significant inhibition on the chemotaxis of macrophages from mouse peritoneal cavity induced by PAF which maybe is one the of mechanisms underlying its anti-inflammatory action.

| The inhibition of the compounds on the chemotaxis of macrophages from mouse peritoneal cavity in vitro | |
| --- | --- |
| Compounds | IC$_{50}$ (mol · L$^{-1}$) |
| 36 | 4.48 × 10$^{-8}$ |
| 37 | 8.32 × 10$^{-8}$ |
| 3 | 4.77 × 10$^{-10}$ |

Experimental Example 7

The Inhibition of the Compound on the Increase of Intracellular Calcium Level of Rat Polymorphonuclear Leucocytes In Vitro 1% carrageenan was used to induce polymorphonuclear leucocytes from rat peritoneal cavity. The Fura-2/AM (final concentration: 3×10$^{-6}$ mol·L$^{-1}$) was added into cells suspension. 1 ml of cells suspension was added into the test tube with compound or solvent. The test tubes were placed in a shaking waterbath at 37° C. for 45 min. Then the test tubes were cooled at room temperature for 15 min. The cells were rinsed twice using HBSS to discarded Fura-2/AM remained in outside of the cells. The suspension of cells loaded with Fura-2/AM was added into the absorbent chamber of fluorospectrometer. The cells were kept to suspend at 37° C. and the fluorescence strength was measured at resting condition or after 20μl of PAF (1×10$^{-4}$ mol·L$^{-1}$), 20 μl of 10% Triton X-100 and 100 μl EGTA (500 mmol·L−1) was added, respectively. The changes of the intracellular level of calcium at the resting condition or after irritants were added was calculated by program for Ca$^{2+}$ measurement.

The result shows that the compound can significantly inhibit the increase of intracellular calcium level of polymorphonuclear leucocytes. It is suggested that the effects of the compound on the binding between PAF and its receptor and the following signal transduction maybe contribute to the mechanism of anti-inflammatory action.

| The inhibition of the compound on the increase of intracellular calcium level of rat polymorphonuclear leucocytes in vitro | |
| --- | --- |
| Compounds | IC$_{50}$ (mol · L$^{-1}$) |
| 20 | 5.16 × 10$^{-6}$ |

Experimental Example 8

The Inhibition of the Compounds on the Production of No in Macrophages from Mouse Peritoneal Cavity In Vitro 4% of sodium mercaptoethanol was injected into C57BL/6 mouse peritoneal cavity to induce macrophages. The cells in peritoneal cavity were collected after injection for 3-4 days. 500 μl of cells were inoculated in the well of 24 wells plate which was placed in the CO$_2$ incubator at 37° C. for 2.5 hr to make the cells adherent. The cells were rinsed by 1640 culture media. 495 μl of 1640 media containing irritant and 5 μl the compound or solvent were added into each well. The plate was incubated for 24 hr. The supernatant was taken out and mixed with the same volume of Griess agent. The reaction fluid was kept at room temperature for 10 min and the optical density was measured at 550 nm. The numbers read was transferred into the content of NO.

The results show that the compounds can significantly inhibit the production of NO in macrophages from mouse peritoneal cavity costimulated by LPS ($1\times10^{-9}$ mol·L$^{-1}$) and PAF ($1\times10^{-6}$ mol·L$^{-1}$). It is suggested that the inhibition of NO production maybe contribute to the mechanisms of their anti-inflammatory action.

| The inhibition of the compounds on the production of NO in macrophages from mouse peritoneal cavity in vitro | |
| --- | --- |
| Compounds | IC$_{50}$ (mol · L$^{-1}$) |
| 3 | $2.25 \times 10^{-7}$ |
| 37 | $3.69 \times 10^{-6}$ |
| 36 | $3.23 \times 10^{-6}$ |

Experimental Example 9

The Inhibition of the Compounds on the Production of TNF-α by Macrophages from Mouse Peritoneal Cavity In Vitro The macrophages from mouse peritoneal cavity were prepared as described before. 500 µl of cells were inoculated in 48-well plate which was incubated with 5% CO$_2$ at 37° C. for 2.5 hr. The compounds and LPS (final concentration: 10 µg·ml$^{-1}$) were added into each well of the plate. After incubating for 24 hr the supernatant was collected. The content of TNF-α was determined by following method. 100 µl of L929 cells ($2\times10^5$cells·ml$^{-1}$) with 100 µl of RPMI-1640 or supernatant collected above were inoculated into 96-well plate which incubated under 5% CO2 at 37° C. for 20 hr. The supernatant was discarded. 200 µl of 0.5% crystal violet was added into each well. 10 min later crystal violet outside of the cells was rinsed using normal saline. The cells were dried under room temperature. 100 µl of 10% SDS was added into each well. After the cells were lysed completely the optical density was measured at 570 nm. The well of 1640 media was as the control, The content of TNF-a was evaluated by the percentage of L929 cells survival.

The results show that the compounds can significantly inhibit the production of TNF-α by macrophages from mouse peritoneal cavity which maybe contribute to the mechanisms of their anti-inflammatory action.

| The inhibition of the compounds on the production of TNF-α by macrophages from mouse peritoneal cavity in vitro | |
| --- | --- |
| Compounds | IC$_{50}$ (mol · L$^{-1}$) |
| 3 | $3.4 \times 10^{-8}$ |
| 37 | $2.0 \times 10^{-9}$ |
| 36 | $4.58 \times 10^{-8}$ |

Experimental Example 10

The Inhibition of the Compounds on the Mouse Ear Edema Induced by Croton Oil

Kuming mice (male, 18-22 g) were randomly divided into two groups (treatment and control) with 10 animals for each group. The animals were orally administrated with compounds or solvent, respectively. 1 hr later, 50 µl of 2% croton oil was smeared on the two sides of mouse left ear. After 4 hr the mice were sacrificed by cervical vertebra displacement. The two ears were cut off and the central sections were excised using a punch with a diameter of 8 mm and weighed. Edema was quantified as the weight difference between the two sections.

The results show that the compounds orally administrated at dose of 50 mg·kg$^{-1}$ can significantly inhibit the mouse ear edema induced by croton oil.

| The inhibition of the compounds on the mouse ear edema induced by croton oil | |
| --- | --- |
| Compounds | Inhibition (%) |
| 20 | 27.66 |
| 22a | 31.22 |
| 3 | 33.52 |
| 16 | 29.05 |
| 37 | 33.20 |

Experimental Example 11

The Inhibition of the Compounds on the Mouse Paw Swelling Induced by Carrageenan Kunming mice (male, 18-22 g) were randomly divided into two groups (treatment and control) with 10 animals for each group. The animals were orally administrated with compounds or solvent, respectively. 1 hr later, 50 µl of 1% carrageenan was intracutaneously injected into the sole of right posterior foot. After 4 hr the animals were sacrificed by displacing cervical vertebra. The two paws were cut off at ankle joint and weighed. The swelling was evaluated by the difference of the weights of two paws.

The results show that the compounds orally administrated at dose of 50 mg·kg$^{-1}$ can inhibit the mouse paw swelling induced by carrageenan.

| The inhibition of the compounds on the mouse paw swelling induced by carrageenan | |
| --- | --- |
| Compounds | Inhibition (%) |
| 20 | 21.46 |
| 22a | 23.33 |
| 3 | 32.52 |
| 37 | 21.60 |
| 36 | 28.00 |

Experimental Example 12

The Inhibition of the Compounds on the Increase of Cutaneous Vascular Permeability in Mice Induced by PAF Kunming mice (male, 18-22 g) were randomly divided into two groups (treatment and control) with 10 animals for each group. The animals were orally administrated with the compounds or solvent, respectively. 1 hr later, 0.25 ml of 1% evans blue dye was injected into the tail vein. After 10 min, 0.1 ml of PAF ($1\times10^{-8}$ mol·L$^{-1}$) was intracutaneously injected into the dorsal skin shaved. 1 hr later, the animals were sacrificed by cervical vertebra displacement. The skin with blue spot was cut off. The evans blue dye was extracted by 0.8 ml of mixed solution of acetone and normal saline (7:3). The supernatant was transferred into the 96-well plate. The optical density was measured at 620 nm.

The results show that the compounds orally administrated at dose of 50 mg·kg$^{-1}$ can significantly inhibit the increase of cutaneous vascular permeability which maybe contribute to the mechanisms of their anti-inflammatory action.

The inhibition of the compounds on the increase of cutaneous vascular permeability in mice induced by PAF

| Compounds | Inhibition (%) |
|---|---|
| 20 | 55.78 |
| 22a | 51.14 |
| 3 | 53.23 |
| 16 | 48.09 |
| 37 | 38.70 |
| 36 | 33.50 |

Experimental Example 13

The Inhibition of the Compound on the Rat Paw Swelling Induced by Carrageenan

Wistar rats (male, 180±20 g) were randomly divided into two groups (treatment and control) with 10 animals for each group. The animals were orally administered with the compound or solvent, respectively. 1 hr later, 100 µl of 1% carrageenan was intracutaneously injected into the sole of right posterior foot. The perimeter of the ankle joint inflamed was measured at indicated time. The swelling level was evaluated by the difference of perimeters between the inflamed foot and non-inflamed foot.

The result shows that the compound orally administrated at dose of 100 mg·kg$^{-1}$ can significantly inhibit the rat paw swelling.

The inhibition of the compound on the rat paw swelling induced by carrageenan

| | Inhibition (%) | | | | |
|---|---|---|---|---|---|
| Compounds | 1 h | 2 h | 3 h | 4 h | 5 h |
| 3 | 49.7 | 55.5 | 44.2 | 29.0 | 19.4 |

Experimental Example 14

The Inhibition of the Compound on the Rat Granuloma Induced by Cotton Ball

Wistar rats (male, 165±15 g) were randomly divided into two groups (treatment and control) with 10 animals for each group. 10 mg of steriled cotton ball was planted into the two groins of the rat under the anaesthetized by ether. The animals were orally administrated with the compound for 7 days. At seventh day the cotton ball was taken out, dried by the oven and weighed. The hyperplasia of granuloma was evaluated by the increase of weight of dried cotton ball.

The result shows that the compound orally administrated at dose of 100 mg·kg$^{-1}$ can inhibit the hyperplasia of granuloma induced by cotton ball in rats. It is indicated that the compound can counterwork the chronic inflammation.

The inhibition of the compounds on the rat granuloma induced by cotton ball

| Compounds | Inhibition (%) |
|---|---|
| 3 | 37.93 |

Experimental Example 15

The Inhibition of the Compound on the Adjuvant Arthritis in Rat

SD rats (male, 190±10 g) were randomly divided into two groups (treatment and control) with 10 animals for each group. At 0 day 0.1 ml of Freund's complete adjuvant was intracutaneously injected into the right posterior foot. For therapeutic experiment the animals were orally administrated with the compound or solvent during 19-25th day. The perimeter of two ankle joint was measured and the inflammation of anterior foot, ear and tail were judged by scoring for every 3 days until 28 th day.

The result shows that the compound orally administrated at dose of 100 mg·kg$^{-1}$ can significantly inhibit the adjuvant arthritis in rats. It is indicated that the compound can inhibit the immune inflammation.

The inhibition of the compound on the adjuvant arthritis in rat (therapeutic effect)

| | Inhibition (%) | | | |
|---|---|---|---|---|
| Compound | 21th day | 23th day | 25th day | 27th day |
| 3 | 31.9 | 49.3 | 54.5 | 59.3 |

Experimental Example 16

The Inhibition of the Compound on the Angiogenesis of the Chronic Granulomatous Air Pouch in Mice 3 ml of air was injected into the dorsal subcutaneous tissue. 24 hr later, 0.5 ml of 0.1% croton oil in Freund's complete adjuvant was injected into the air pouch. Meanwhile the compound or solvent was orally administrated everyday. At sixth day the mice were anaesthetized and kept at 40° C. for 10 min. 1 ml of 1% carmine red containing 5% gelatin was injected into the tail vein. The animal was kept at 0-4° C. for 2-3 hr. The air-pouch tissue was detached, dried in oven at 56° C. for 48 hr, weighed and cut to small pieces. 2 ml of digesting fluid was added into the tissue. The carmine red was solved by NaOH (5 mol·L$^{-1}$). The supernatant was isolated and filtered. The absorbance was measured at 540 nm. The content of carmine red was calculated according to the correct curve.

The result shows that the compound can significantly decrease the content of carmine red. It is indicated that the compound can inhibit the angiogenesis in murine chronic granulomatous air pouch.

| The inhibition of the compound on the angiogenesis of the chronic granulomatous air pouch in mice | | |
|---|---|---|
| Compound | Dose (mg · kg$^{-1}$ × 5 d) | Inhibition (%) |
| 3 | 12.5 | 17.8 |
|  | 25 | 20.6 |
|  | 50 | 28.4 |

Experimental Example 17

The Inhibition of the Compound on the Arthritis Induced by Type ☐ Collagen in Rat 0.1 ml of type II H collagen (2 mg·ml$^{-1}$) was intracutaneously injected into the hind foot of Wistar rat (male, 100±10 g) (d0). Seven days later 0.1 ml of type II collagen was intracutaneously injected into the root of tail. At 19th day (d19) the animals inflamed were selected to supply the experiment and randomly divided into two groups. The compound or solvent was orally administrated from that day to 42th day. The perimeter of the ankle joint of two hind feet, weight of body was measured and the systemic inflammation (including the toes of front and hind feet, ears and tails) was judged by scoring every 3 days. At 41th day 40 μl of 0.2% type II collagen was intracutaneously injected into the right ear. Twenty-four hr later the edema level was evaluated by weighing the ponderance of ear piece (diameter: 8 mm). At 42th day the blood was collected by decapitating. The serum was separated by centrifugating. The contents of antibody for anti-type II collagen, cytokine TNF-α, IL-1β in serum were determined by ELISA kit.

The results show that the compound orally administrated at dose of 100 mg·kg$^{-1}$×13 d can significantly inhibit rat arthritis induced by type II collagen and reduce the production of antibody for anti-type II collagen, TNF-α and IL-1β in serum. It is indicated that the compound has the inhibitory effect on immune inflammation.

TABLE 1

| The inhibition of the compound on the rat arthritis induced by 7type II collagen | | | |
|---|---|---|---|
|  | Inhibition (%) | | |
| Compound | Swelling of right ankle joint | Swelling of left ankle joint | Score for systemic inflammation |
| 3 (100 mg · kg$^{-1}$ × 13 d) | 68.8 | 67.5 | 52.6 |

TABLE 2

| The inhibition of the compound on the delayed hypersensitivity in rats | | |
|---|---|---|
| Compound | Dose (mg · kg$^{-1}$ × 13 d) | Inhibition (%) |
| 3 | 100 | 21.2 |

TABLE 3

| The inhibition of the compound on the production of TNF-α in serum of rat with arthritis induced by type II collagen | | |
|---|---|---|
| Compound | dose (mg · kg$^{-1}$ × 13 d) | inhibition (%) |
| 3 | 100 | 49.3 |

TABLE 4

| The inhibition of the compound on the production of IL-1β in serum of rat with arthritis induced by type II collagen | | |
|---|---|---|
| Compound | Dose (mg · kg$^{-1}$ × 13 d) | Inhibition (%) |
| 3 | 100 | 45.7 |

TABLE 5

| The inhibition of the compound on the production of IgG in serum of rat with arthritis induced by type II collagen | | |
|---|---|---|
| Compound | Dose (mg · kg$^{-1}$ × 13 d) | Inhibition (%) |
| 3 | 100 | 38.4 |

The invention claimed is:

1. A compound represented by the following general formula (Iaa), and its stereoisomers:

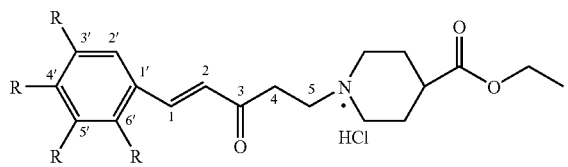

(Iaa)

Wherein R'$_3$, R'$_4$, R'$_5$ and R'$_6$ are independently selected from the group consisting of hydrogen, C$_{1-5}$ alkyl, methylenedioxy, C$_{1-6}$ alkoxy, halogen (F, CI, Br, I), hydroxy, NO$_2$, CF$_3$, CN, 3,4,5-tri-C$_{1-6}$ alkoxy, 3-methoxy-4-hydroxy, and 3,4-methylenedioxy-5-methoxy.

2. A compound represented by the following general formula (Iab), and its stereoisomers:

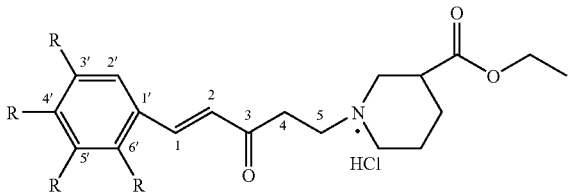

(Iab)

Wherein R'$_3$, R'$_4$, R'$_5$ and R'$_6$ are independently selected from the group consisting of hydrogen, C$_{1-6}$ alkyl, methylenedioxy, C$_{1-6}$ alkoxy, halogen (F, CI, Br, I), hydroxy, NO$_2$, CF$_3$, CN, 3,4,5-tri-C$_{1-6}$ alkoxy, 3-methoxy-4-hydroxy, and 3,4-methylenedioxy-5-methoxy.

3. A compound selected from the group consisting of

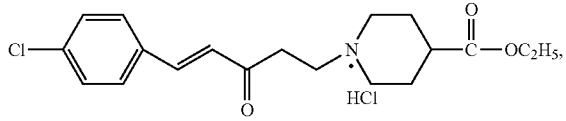

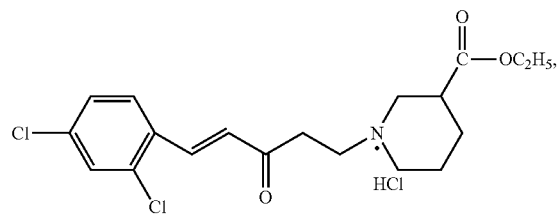

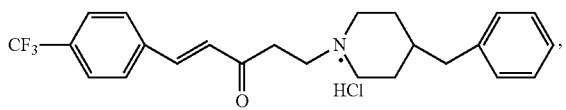

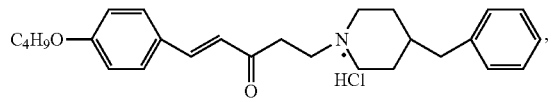

-continued

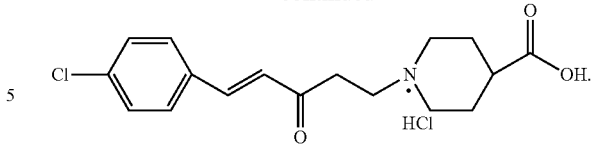

and stereoisomers thereof.

4. A pharmaceutical composition comprising a pharmaceutically effective dosage of the compound according to claim 1, and a pharmaceutically acceptable carrier.

5. The pharmaceutical composition according to claim 4, characterized in that the pharmaceutical composition is a tablet, capsule, pill, injection, sustained-release, controlled-release, or a fine particle delivery system.

6. A pharmaceutical composition comprising a pharmaceutically effective dosage of the compound according to claim 2, and a pharmaceutically acceptable carrier.

7. The pharmaceutical composition according to claim 6, characterized in that the pharmaceutical composition is a tablet, capsule, pill, injection, sustained-release, controlled-release, or a fine particle delivery system.

8. A pharmaceutical composition comprising a pharmaceutically effective dosage of the compound according to claim 3, and a pharmaceutically acceptable carrier.

9. The pharmaceutical composition according to claim 8, characterized in that the pharmaceutical composition is a tablet, capsule, pill, injection, sustained-release, controlled-release, or a fine particle delivery system.

* * * * *

UNITED STATES PATENT AND TRADEMARK OFFICE
CERTIFICATE OF CORRECTION

PATENT NO.        : 8,524,744 B2                               Page 1 of 1
APPLICATION NO.   : 11/659636
DATED             : September 3, 2013
INVENTOR(S)       : Zhu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1602 days.

Signed and Sealed this
Fifteenth Day of September, 2015

Michelle K. Lee
*Director of the United States Patent and Trademark Office*